(12) United States Patent
Markham et al.

(10) Patent No.: US 10,010,625 B2
(45) Date of Patent: Jul. 3, 2018

(54) ANTIMICROBIAL COMPOSITIONS COMPRISING SINGLE DOMAIN ANTIBODIES AND PSEUDOMONAS EXOTOXIN

(71) Applicant: THE JOHNS HOPKINS UNIVERSITY, Baltimore, MD (US)

(72) Inventors: Richard Markham, Columbia, MD (US); Eileen Geoghegan, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 7 days.

(21) Appl. No.: 15/108,380

(22) PCT Filed: Jan. 2, 2015

(86) PCT No.: PCT/US2015/010045
§ 371 (c)(1),
(2) Date: Jun. 27, 2016

(87) PCT Pub. No.: WO2015/103479
PCT Pub. Date: Jul. 9, 2015

(65) Prior Publication Data
US 2016/0339112 A1 Nov. 24, 2016

Related U.S. Application Data

(60) Provisional application No. 61/922,927, filed on Jan. 2, 2014.

(51) Int. Cl.
| | | |
|---|---|---|
| *C07K 16/08* | (2006.01) | |
| *C07K 14/21* | (2006.01) | |
| *A61K 39/00* | (2006.01) | |
| *A61K 47/48* | (2006.01) | |

(52) U.S. Cl.
CPC .. *A61K 47/48523* (2013.01); *A61K 47/48484* (2013.01); *C07K 14/21* (2013.01); *C07K 16/087* (2013.01); *A61K 2039/505* (2013.01); *A61K 2039/70* (2013.01); *C07K 2317/35* (2013.01); *C07K 2317/51* (2013.01); *C07K 2317/569* (2013.01); *C07K 2317/76* (2013.01); *C07K 2319/55* (2013.01)

(58) Field of Classification Search
CPC ............ C07K 2317/622; C07K 14/005; C07K 2317/92; C07K 2317/56; C07K 16/00; C07K 2317/52; C07K 2317/55; C07K 2317/51; C07K 2317/569; C07K 2319/55; C07K 16/087; C07K 2317/22; C07K 14/035; A61K 39/12; A61K 39/245; A61K 38/1774; A61K 2039/525; A61K 35/76; A61K 35/763; A61K 39/00; A61K 2039/6056
See application file for complete search history.

(56) References Cited

U.S. PATENT DOCUMENTS

| | | | |
|---|---|---|---|
| 2013/0164307 A1 | 6/2013 | Markham | |
| 2015/0158934 A1* | 6/2015 | McCoy | .............. C07K 16/1063 530/387.3 |

FOREIGN PATENT DOCUMENTS

WO 2012019058 A1 2/2012

OTHER PUBLICATIONS

Garaicoechea, L., et al., (2008) "Llama-derived single-chain antibody fragments directed to rotavirus VP6 protein possess broad neutralizing activity in vitro and confer protection against diarrhea in mice", Journal of Virology, vol. 82, No. 19, pp. 9753-9764.

Geoghegan, E., et al., (2015) "Antiviral activity of a single-domain antibody immunotoxin binding to glycoprotein D of herpes simplex virus 2", Antimicrobial Agents and Chemotherapy, vol. 59, No. 1, pp. 527-535.

Serruys, B., et al., (2009) "Llama-derived single-domain intrabodies inhibit secretion of hepatitis B virions in mice", Hepatology, vol. 49, No. 1, pp. 39-49.

Wesolowski, J., et al., (2009) "Single domain antibodies: promising experimental and therapeutic tools in infection and immunity", Medical Microbiology and Immunology, vol. 198, No. 3. pp. 157-174.

* cited by examiner

*Primary Examiner* — Rachel B Gill
(74) *Attorney, Agent, or Firm* — John Hopkins Technology Ventures

(57) ABSTRACT

The present invention provides heavy chain immunoglobulins of the VHH type or fragment thereof having affinity for a target antigen of interest, including glycoprotein D2 (gD2) of HSV-2 or antigen thereof, and for envelope proteins of HIV-1 or an antigen thereof linked to *Pseudomonas* exotoxin A or functional fragments thereof. Also included are multimeric forms of the immunoglobulins and their use in the prevention and/or treatment of HSV2 and/or HIV-1.

18 Claims, 24 Drawing Sheets

FIGURE 12

```
            MAEVQLQASGGGLVQAGGSLRLSCAASGRATGNYPMGWFRQAPGKEREFVAAISRDGDYT
                    10        20        30        40        50        60
No. 2 -1    MADVQLQASGGGLVQTGGSLRLSCAASGRATGNYPMGWFRQAPGKEREFVAAISRDGDST  60
No. 2 -15   MAEVQLQASGGGLVQAGGSLRLSCAASGRATGNYPMGWFRQAPGKEREFVAAISRDGDYT  60
No. 2 -17   MAEVQLQASGGGLVRAGGSLRLSCTASGRATGNYPMGWFRQAPGKEREFVAAISRDGDST  60
No. 2 -18   MAEVQLQASGGGLVQAGGSLRLSCAASGRATGNYPMGWFRQAPGKEREFVAAISRDGDYT  60
No. 2 -33   MAEVQLQASGGGLVQAGGSLRLSCAASGRATGNYPMGWFRQAPGKEREFVAAISRDGDST  60
No. 2 -39   MADVQLQASGGGLVQAGGSLRLSCAASGRATGNYPMGWFRQAPGKEREFVAAISRDGDST  60
No. 1 -1    MAEVQLQASGGGLVQPGGSLTLSCVVTGSPAEPNAVGWYRQASGKQREWVGRIIPSG--T  58
No. 1 -3    MAEVQLQASGGGLVQPGGSLTLSCVVTGSPAEPNAVGWYRQASGKQREWVGRIIPSG--T  58
No. 1 -4    MAEVQLQASGGGAVEVGGSLTLSCVVTGSPAEPNAVGWYRQASGKQREWVGRIIPSG--T  58
No. 1 -15   MAEVQLQASGGGLVQSGGSLRLSCVVTGSPAEPNAVGWYRQASGKQREWVGRIIPSG--T  58
No. 1 -10   MAEVQLQASGGGVVQPGGSLRLSCVSSGFRFNVYAIGWFRQAPGKEREAVGAISTTDGVT  60

YYADSVKGRFTISRDNAKNTYYLQMNSLKPEDTAVYYCAAD-RLTAYRYNPGQIDYWGQG
                    70        80        90       100       110       120
No. 2 -1    YYRDSVKGRFTISRDNAKNTVYLQMNSLKPEDTAVYYCAAD-RLTAYRYNPGQIDYWGQG  119
No. 2 -15   YYADSVKGRFTISKNNAKDTVYLQMNSLKPEDTAVYYCTAD-RLTAYRYNPGQIDYWGQG  119
No. 2 -17   YYRDSVKGRFTISRDNAKNTVYLQMNSLKPEDTAVYYCAAD-RLTAYRYNPGQIDYWGQG  119
No. 2 -18   YYTDSVKGRFTISKNNAKDTVYLQMNSLKPEDTAVYYCTAD-RLTAYRYNPGQIDYWGQG  119
No. 2 -33   YYRDSVKGRFTISRDNAKNTVYLQMNSLKPEDTAVYYCAAD-RLTAYRYNPGQIDYWGQG  119
No. 2 -39   YYRDSVKGRFTISRDNAKNTVYLQMNSLKPEDTAVYYCAAD-RLTAYRYNPGQIDYWGQG  119
No. 1 -1    RYADFVKGRFIISRDSAKSTVYLQMNSLKPEDTAVYYCSPLTGSGTYYRSTT----FGQG  114
No. 1 -3    RYADFVKGRFIISRDSAKSTVYLQMNSLKPEDTAAYYCSPLTGSGTYYRSTT----FGQG  114
No. 1 -4    RYADFVKGRFIISRDSAKSTVYLQMNSLKPEDTAVYYCSPLTGSGTYYRSTT----FGQG  114
No. 1 -15   RYADFVKGRFIISRDSAKSTVYLQMNSLKPEDTAVYYCSPLTGSGTYYRSTT----FGQG  114
No. 1 -10   TYADAVRYRFSITNDRAKNTVYLQMNNLKPEDTAIYYCAARGTWGLLSLDVSEYGYWGQG  128

TQVTVSS                                                       SEQ ID NO: 15
No. 2 -1    TQVTVSS                                                   126  SEQ ID NO: 16
No. 2 -15   TQVTVSS                                                   126  SEQ ID NO: 17
No. 2 -17   TQVTVSS                                                   126  SEQ ID NO: 18
No. 2 -18   TQVTVSS                                                   126  SEQ ID NO: 19
No. 2 -33   TQVTVSS                                                   126  SEQ ID NO: 20
No. 2 -39   TQVTVSS                                                   126  SEQ ID NO: 21
No. 1 -1    TQVTVSS                                                   121  SEQ ID NO: 22
No. 1 -3    TQVTVSS                                                   121  SEQ ID NO: 23
No. 1 -4    TQVTVSS                                                   121  SEQ ID NO: 24
No. 1 -15   TQVTVSS                                                   121  SEQ ID NO: 25
No. 1 -10   TQVTVSS                                                   127  SEQ ID NO: 26
```

R33ExoA
- VECTOR ENCODED OR LINKER REGION
- HIS TAG
- VHH
- EXOTOXIN A

ATGGCACATCACCACCACCATCACTCGCGGCTCTTGAAGTCCTCTTTCAGGGAC
CCGGGTACCAGGATCCGAATTCTATGGCGAGGTGCAGCTGCAGGCGTCTGGGG
GAGGATTGGTGCAGGCTGGGGCTCTCTGAGACTCTCCTGTGCAGCCTCTGGACG
CGCCACCGGTAACTATCCATGGGCTGGTTCCGCCAGGCTCCAGGGAAGGAGCG
TGAGTTTGTAGCCGCTATTAGCCGGGATGGAGATAGCACATACTACAGAGACTCC
GTGAAGGGCCGATTCACCATCTCCAGAGACAACGCCAAGAACACGGTGTATCTG
CAAATGAACAGCCTGAAACCTGAGGACACGGCCGTTTATTACTGTGCAGCAGAC
CGACTTACAGCCTATCGCTACAATCCAGGGCAGATTGACTACTGGGGCCAGGGG
ACCCAGGTCACCGTCTCCTCACTCGAGGCGGCCGCC (SEQ ID NO: 1)
CCCGAGGGCGGCAGCCTGGCCGCGCTGACCGCGCACCAGGCTTGCCACCTGCCG
CTGGAGACTTTCACCCGTCATCGCCAGCCGCGCGGCTGGGAACAACTGGAGCAG
TGCGGCTATCCGGTGCAGCGGCTGGTCGCCCTCTACCTGGCGGCGCGGCTGTCGT
GGAACCAGGTCGACCAGGTGATCCGCAACGCCCTGGCCAGCCCCGGCAGCGGCG
GCGACCTGGGCGAAGCGATCCGCGAGCAGCCGGAGCAGGCCCGTCTGGCCCTGA
CCCTGGCCGCCGCCGAGAGCGAGCGCTTCGTCCGGCAGGGCACCGGCAACGACG
AGGCCGGCGCGGCCAACGGCCCGGCGGACAGCGGCGACGCCCTGCTGGAGCGCA
ACTATCCCACTGGCGCGGAGTTCCTCGGCGACGGCGGCGACGTCAGCTTCAGCAC
CCGaGGCACGCAGAACTGGACGGTGGAGCGGCTGCTCCAGGCGCACgcCCAACTG
GAGGAGCGCGGCTATGTGTTCGTCGGCTACCACGGCACCTTCCTCGAAGCGGCGC
AAAGCATCGTCTTCGGCGGGGTGCGCGCGgcCAGCCAGGACCTCGcCGCGATCTG
GgcCGGTTTCTATATCGCCGGCGATCCGGCGCTGGCCTACGGCTACGCCCAGGAC
CAGGAACCCGACGCAgcCGGCCGaATCCGCAACGGTGCCCTGCTGCGGGTCTATG
TGCCGgcaTCGAGCCTGCCGGGCTTCTACCGCACCAGCCTGACCCTGGCCGCGCCG
GAGGCGGCGGGCGAGGTCGAACGGCTGATCGGCCATCCGCTGCCGCTGgcCCTGG
ACGCCATCACCGGCCCCGAGGAGGAAGGCGGGCGCCTGGAGACCATTCTCGGCT
GGCCGCTGGCCGAGCGCACCGTGGTGATTCCCTCGGCGATCCCCACCGACCCGCG
CAACGTCGGCGGCGACCTCGACCCGTCCAGCATCCCCGACAAGGAACAGGCG
CAGCGCCCTGCCGGACTACGCCAGCCAGCCCGGCAAACCGCCGCGAGGACCT
GAAGTAA (SEQ ID NO: 2)

FIG. 22A

MAHHHHHHSAALEVLFQGPGYQDPNSMAEVQLQASGGGLVQAGGSLRLSCAASGR
ATGNYPMGWFRQAPGKEREFVAAISRDGDSTYYRDSVKGRFTISRDNAKNTVYLQM
NSLKPEDTAVYYCAADRLTAYRYNPGQIDYWGQGTQVTVSSLEAAA
(SEQ ID NO: 3)
PEGGSLAALTAHQACHLPLETFTRHRQPRGWEQLEQCGYPVQRLVALYLAARLSWN
QVDQVIRNALASPGSGGDLGEAIREQPEQARLALTLAAAESERFVRQGTGNDEAGA
ANGPADSGDALLERNYPTGAEFLGDGGDVSFSTRGTQNWTVERLLQAHAQLEERGY
VFVGYHGTFLEAAQSIVFGGVRAASQDLAAIWAGFYIAGDPALAYGYAQDQEPDAA
GRIRNGALLRVYVPASSLPGFYRTSLTLAAPEAAGEVERLIGHPLPLALDAITGPEEEG
GRLETILGWPLAERTVVIPSAIPTDPRNVGGDLDPSSIPDKEQAISALPDYASQPGKPP
REDLK (SEQ ID NO: 4)

ANNOTATED SEQUENCE OF INSERT CONTAINING J3 VHH FUSED TO EXOTOXIN A

KEY
- CONTAINS RESTRICTION SITES
  - 5' END EcoRI
  - 3' END AvrII
- J3 VHH
- LINKER REGION
  - INCLUDES MULTIPLE CLONING SITE SEQUENCE
  - INCLUDES MYC TAG
- BOLD SEQUENCE IS THE P. AERUGINOSA EXOTOXIN A SUBUNIT
- STOP CODON

GAATTCCGAAGTGCAGCTGGTGGAAAGCGGCGGCGGCCTGGTGCAGGCGGGCGGCTTC
TGCGCCTGAGCTGCGAACTGCGCGGCAGCATTTTTAACCAGTATGCGATGGGCTGGTTTC
GCCAGGCGCCGGGCAAAGAACGCGAATTTGTGGCGGGCATGGGCGCGGTGCCGCATTAT
GGCGAATTTGTGAAAGGCCGCTTTACCATTAGCCGCGATAACGCGAAAAGCACCGTGTA (FIG. 23A CONT'D)
TTCTGCAGATGAGCAGCCTGAAACCGGAAGATACCGCGATTTATTTTTGCGCGCGCAGCA
AAAGCACCTATATTAGCTATAACAGCAACGGCTATGATTATTGGGGCCGCGGCACCCAG
GTGACCGTGAGCAGC *CTGCAGGACGTCACTAGTCCATGGCATATG*GAACAGAAACTGATCTC
AGAAGAGGATCTGCTCGAGGCGGCCGCCC
(SEQ ID NO: 5)
CGGAAGGTGGCAGCCTGGCAGCACTGACCGCTCATCAGGCATGCCCACCTGCCGCTG
GAAACCTTTACGCGTCATCGTCAGCCGCGTGGCTGGGAACAGCTGGAACAATGTGG
TTATCCGGTCCAGCGTCTGGTGGCCCTGTACCTGGCAGCTCGCCTGAGCTGGAACC
AGGTGGATCAAGTTATTCGTAATGCACTGGCAAGCCCGGGTTCTGGCGGTGACCTG
GGTGAAGCGATCCGTGAACAGCCGGAACAAGCACGTCTGGCACTGACCCTGGCAG
CAGCAGAAAGCGAACGTTTCGTGCGCCAGGGCACGGGTAACGATGAAGCCGGCGC
TGCGAATGGTCCGGCTGATTCTGGCGACGCGCTGCTGGAACGTAACTATCCGACCG
GCGCAGAATTTCTGGGTGATGGCGGTGACGTGTCATTCTCGACCCGTGGCACGCAG
AATTGGACGGTTGAACGCCTGCTGCAGGCTCATGCGCAACTGGAAGAACGTGGTTA
TGTCTTTGTGGCTACCACGGCACCTTCCTGGAAGCCGCACAGTCAATTGTTTTTGG
CGGTGTCCGCGCTGCGTCGCAAGATCTGGCCGCAATTTGGGCCGGCTTCTACATCG
CAGGTGACCCGGCCCTGGCATATGGCTACGCGCAGGATCAAGAACCGGACGCTGC
AGGTCGTATCCGTAACGGTGCTCTGCTGCGTGTTTATGTCCCGGCCAGCTCTCTGC
CGGGTTTTACCGTACCTCACTGACGCTGGCAGCACCGGAAGCTGCAGGCGAAGTC
GAACGTCTGATTGGTCACCCGCTGCCGCTGGCTCTGGATGCAATCACCGGTCCGGA
AGAAGAAGGCGGCCGTCTGGAAACGATTCTGGGTTGGCCGCTGGCAGAACGCACC
GTGGTTATTCCGTCCGCGATCCCGACCGACCCGCGCAATGTTGGCGGTGATCTGGA
CCCGAGTTCCATTCCGGATAAAGAACAGGCCATCAGTGCACTGCCGGACTATGCGT
CCCAACCGGGTAAACCGCCGCGTGAAGATCTGAAATAACCTAGG (SEQ ID NO:6)

FIG. 23B

PNSEVQLVESGGGLVQAGGFLRLSCELRGSIFNQYAMGWFRQAPGKEREFVAGMGAYPHYG
EFVKGRFTISRDNAKSTVYLQMSSLKPEDTAIYFCARSKSTYISYNSNGYDYWGRGTQVTVSS
*LQDVTSPWHMEQKLISEEDLLE*AAA
(SEQ ID NO:7)

(FIG. 23B CONT'D)
PEGGSLAALTAHQACHLPLETFTRHRQPRGWEQLEQCGYPVQRLVALYLAARLSWNQ
VDQVIRNALASPGSGGDLGEAIREQPEQARLALTLAAAESERFVRQGTGNDEAGAANGP
ADSGDALLERNYPTGAEFLGDGGDVSFSTRGTQNWTVERLLQAHAQLEERGYVFVGY
HGTFLEAASIVFGGVRAASQDLAAIWAGFYIAGDPALAYGYAQDQEPDAAGRIRNGAL
LRVYVPASSLPGFYRTSLTLAAPEAAGEVERLIGHPLPLALDAITGPEEEGGRLETILGW
PLAERTVVIPSAIPTDPRNVGGDLDPSSIPDKEQAISALPDYASQPGKPPREDLK*PR*
(SEQ ID NO:8)

FIG. 24

MAHHHHHHSAALEVLFQGPGYQD*PNS*EVQLVESGGGLVQAGGFLRLSCELRGSIFN
QYAMGWFRQAPGKEREFVAGMGAVPHYGEFVKGRFTISRDNAKSTVYLQMSSLKP
EDTAIYFCARSKSTYISYNSNGYDYWGRGTQVTVSS (SEQ ID NO:11)

MAHHHHHHSAALEVLFQGPGYQD*PNS*EVQLVESGGGLVQAGGFLRLSCELRGSIFN
QYAMGWFRQAPGKEREFVAGMGAVPHYGEFVKGRFTISRDNAKSTVYLQMSSLKP
EDTAIYFCARSKSTYISYNSNGYDYWGRGTQVTVSS*LQDVTSPWHMEQKLISEEDLLE*
*AAA*PEGGSLAALTAHQACHLPLETFTRHRQPRGWEQLEQCGYPVQRLVALYLA
ARLSWNQVDQVIRNALASPGSGGDLGEAIREQPEQARLALTLAAAESERFVRQG
TGNDEAGAANGPADSGDALLERNYPTGAEFLGDGGDVSFSTRGTQNWTVERLL
QAHAQLEERGYVFVGYHGTFLEAAQSIVFGGVRAASQDLAAIWAGFYIAGDPA
LAYGYAQDQEPDAAGRIRNGALLRVYVPASSLPGFYRTSLTLAAPEAAGEVERL
IGHPLPLALDAITGPEEEGGRLETILGWPLAERTVVIPSAIPTDPRNVGGDLDPSSI
PDKEQAISALPDYASQPGKPPREDLK*PR* (SEQ ID NO:12)

SEQUENCE LISTING

```
<160> NUMBER OF SEQ ID NOS: 26

<210> SEQ ID NO 1
<211> LENGTH: 471
<212> TYPE: DNA
<213> ORGANISM: Artificial Sequence
<220> FEATURE:
<223> OTHER INFORMATION: Synthetic Sequence

<400> SEQUENCE: 1
atggcacatc accaccacca tcactccgcg gctcttgaag tcctctttca gggacccggg     60
```

```
taccaggatc cgaattctat ggccgaggtg cagctgcagg cgtctggggg aggattggtg      120
caggctgggg gctctctgag actctcctgt gcagcctctg gacgcgccac cggtaactat      180
cccatgggct ggttccgcca ggctccaggg aaggagcgtg agtttgtagc cgctattagc      240
cgggatggag atagcacata ctacagagac tccgtgaagg gccgattcac catctccaga      300
gacaacgcca agaacacggt gtatctgcaa atgaacagcc tgaaacctga ggacacggcc      360
gtttattact gtgcagcaga ccgacttaca gcctatcgct acaatccagg cagattgac       420 tactggggcc aggggaccca ggtcaccgtc tcctcactcg aggcggccgc c                471

<210> SEQ ID NO 2
<211> LENGTH: 1513
<212> TYPE: DNA
<213> ORGANISM: Artificial Sequence
<220> FEATURE:
<223> OTHER INFORMATION: Synthetic sequence

<400> SEQUENCE: 2
atggcacatc accaccacca tcactccgcg gctcttgaag tcctctttca gggacccggg       60
taccaggatc cgaattctat ggccgaggtg cagctgcagg cgtctggggg aggattggtg      120
caggctgggg gctctctgag actctcctgt gcagcctctg gacgcgccac cggtaactat      180
cccatgggct ggttccgcca ggctccaggg aaggagcgtg agtttgtagc cgctattagc      240
cgggatggag atagcacata ctacagagac tccgtgaagg gccgattcac catctccaga      300
gacaacgcca agaacacggt gtatctgcaa atgaacagcc tgaaacctga ggacacggcc      360
gtttattact gtgcagcaga ccgacttaca gcctatcgct acaatccagg cagattgac       420 tactggggcc aggggaccca ggtcaccgtc tcctcactcg aggcggccgc ccccgagggc      480
ggcagcctgg ccgcgctgac cgcgcaccag gcttgccacc tgccgctgga cttttcacc     540 cgtcatcgcc agccgcgcgg ctgggaacaa ctggagcagt gcggctatcc ggtgcagcgg      600
ctggtcgccc tctacctggc ggcgcggctg tcgtggaacc aggtcgacca ggtgatccgc      660
aacgccctgg ccagccccgg cagcggcggc gacctgggcg aagcgatccg cgagcagccg      720
gagcaggccc gtctggcccct gaccctggcc gccgccgaga gcgagcgctt cgtccggcag      780
ggcaccggca acgacgaggc cggcgcggcc aacggcccgg cggacagcgg cgacgccctg      840
ctggagcgca actatcccac tggcgcggag ttcctcggcg acggcggcga cgtcagcttc      900
agcacccgag gcacgcagaa ctggacggtg agcggctgc tccaggcgca cgcccaactg      960
gaggagcgcg gctatgtgtt cgtcggctac acggcacct tcctcgaagc ggcgcaaagc     1020
atcgtcttcg gcggggtgcg cgcggccagc caggacctcg ccgcgatctg gccggtttc     1080 tatatcgccg gcgatccggc gctggcctac ggctacgccc aggaccagga acccgacgca     1140
gccggccgaa tccgcaacgg tgccctgctg cgggtctatg tgccggcatc gagcctgccg     1200
ggcttctacc gcaccagcct gaccctggcc gcgccggagg cggcgggcga ggtcgaacgg     1260
ctgatcggcc atccgctgcc gctggccctg gacgccatca ccggcccgga ggaggaaggc     1320
gggcgcctgg agaccattct cggctggccg ctggccgagc gcaccgtggt gattccctcg     1380
gcgatcccca ccgacccgcg caacgtcggc ggcgacctcg acccgtccag catccccgac     1440
aaggaacagg cgcagcgccc tgccggacta cgccagccag cccggcaaac cgccgcgcga     1500
ggacctgaag taa                                                         1513

<210> SEQ ID NO 3
<211> LENGTH: 157
```

```
<212> TYPE: PRT
<213> ORGANISM: Artificial Sequence
<220> FEATURE:
<223> OTHER INFORMATION: Synthetic sequence

<400> SEQUENCE: 3

Met Ala His His His His His Ser Ala Ala Leu Glu Val Leu Phe
1               5                   10                  15

Gln Gly Pro Gly Tyr Gln Asp Pro Asn Ser Met Ala Glu Val Gln Leu
            20                  25                  30

Gln Ala Ser Gly Gly Gly Leu Val Gln Ala Gly Gly Ser Leu Arg Leu
        35                  40                  45

Ser Cys Ala Ala Ser Gly Arg Ala Thr Gly Asn Tyr Pro Met Gly Trp
    50                  55                  60

Phe Arg Gln Ala Pro Gly Lys Glu Arg Glu Phe Val Ala Ala Ile Ser
65                  70                  75                  80

Arg Asp Gly Asp Ser Thr Tyr Tyr Arg Asp Ser Val Lys Gly Arg Phe
                85                  90                  95

Thr Ile Ser Arg Asp Asn Ala Lys Asn Thr Val Tyr Leu Gln Met Asn
            100                 105                 110

Ser Leu Lys Pro Glu Asp Thr Ala Val Tyr Tyr Cys Ala Ala Asp Arg
        115                 120                 125

Leu Thr Ala Tyr Arg Tyr Asn Pro Gly Gln Ile Asp Tyr Trp Gly Gln
    130                 135                 140

Gly Thr Gln Val Thr Val Ser Ser Leu Glu Ala Ala Ala
145                 150                 155

<210> SEQ ID NO 4
<211> LENGTH: 504
<212> TYPE: PRT
<213> ORGANISM: Artificial Sequence
<220> FEATURE:
<223> OTHER INFORMATION: synthetic sequence

<400> SEQUENCE: 4

Met Ala His His His His His Ser Ala Ala Leu Glu Val Leu Phe
1               5                   10                  15

Gln Gly Pro Gly Tyr Gln Asp Pro Asn Ser Met Ala Glu Val Gln Leu
            20                  25                  30

Gln Ala Ser Gly Gly Gly Leu Val Gln Ala Gly Gly Ser Leu Arg Leu
        35                  40                  45

Ser Cys Ala Ala Ser Gly Arg Ala Thr Gly Asn Tyr Pro Met Gly Trp
    50                  55                  60

Phe Arg Gln Ala Pro Gly Lys Glu Arg Glu Phe Val Ala Ala Ile Ser
65                  70                  75                  80

Arg Asp Gly Asp Ser Thr Tyr Tyr Arg Asp Ser Val Lys Gly Arg Phe
                85                  90                  95

Thr Ile Ser Arg Asp Asn Ala Lys Asn Thr Val Tyr Leu Gln Met Asn
            100                 105                 110

Ser Leu Lys Pro Glu Asp Thr Ala Val Tyr Tyr Cys Ala Ala Asp Arg
        115                 120                 125

Leu Thr Ala Tyr Arg Tyr Asn Pro Gly Gln Ile Asp Tyr Trp Gly Gln
    130                 135                 140

Gly Thr Gln Val Thr Val Ser Ser Leu Glu Ala Ala Ala Pro Glu Gly
145                 150                 155                 160

Gly Ser Leu Ala Ala Leu Thr Ala His Gln Ala Cys His Leu Pro Leu
            165                 170                 175
```

Glu Thr Phe Thr Arg His Arg Gln Pro Arg Gly Trp Glu Gln Leu Glu
            180                 185                 190

Gln Cys Gly Tyr Pro Val Gln Arg Leu Val Ala Leu Tyr Leu Ala Ala
            195                 200                 205

Arg Leu Ser Trp Asn Gln Val Asp Gln Val Ile Arg Asn Ala Leu Ala
            210                 215                 220

Ser Pro Gly Ser Gly Gly Asp Leu Gly Glu Ala Ile Arg Glu Gln Pro
225                 230                 235                 240

Glu Gln Ala Arg Leu Ala Leu Thr Leu Ala Ala Ala Glu Ser Glu Arg
            245                 250                 255

Phe Val Arg Gln Gly Thr Gly Asn Asp Glu Ala Gly Ala Ala Asn Gly
            260                 265                 270

Pro Ala Asp Ser Gly Asp Ala Leu Leu Glu Arg Asn Tyr Pro Thr Gly
            275                 280                 285

Ala Glu Phe Leu Gly Asp Gly Asp Val Ser Phe Ser Thr Arg Gly
            290                 295                 300

Thr Gln Asn Trp Thr Val Glu Arg Leu Leu Gln Ala His Ala Gln Leu
305                 310                 315                 320

Glu Glu Arg Gly Tyr Val Phe Val Gly Tyr His Gly Thr Phe Leu Glu
            325                 330                 335

Ala Ala Gln Ser Ile Val Phe Gly Gly Val Arg Ala Ala Ser Gln Asp
            340                 345                 350

Leu Ala Ala Ile Trp Ala Gly Phe Tyr Ile Ala Gly Asp Pro Ala Leu
            355                 360                 365

Ala Tyr Gly Tyr Ala Gln Asp Gln Glu Pro Asp Ala Ala Gly Arg Ile
            370                 375                 380

Arg Asn Gly Ala Leu Leu Arg Val Tyr Val Pro Ala Ser Ser Leu Pro
385                 390                 395                 400

Gly Phe Tyr Arg Thr Ser Leu Thr Leu Ala Ala Pro Glu Ala Ala Gly
            405                 410                 415

Glu Val Glu Arg Leu Ile Gly His Pro Leu Pro Leu Ala Leu Asp Ala
            420                 425                 430

Ile Thr Gly Pro Glu Glu Glu Gly Gly Arg Leu Glu Thr Ile Leu Gly
            435                 440                 445

Trp Pro Leu Ala Glu Arg Thr Val Val Ile Pro Ser Ala Ile Pro Thr
450                 455                 460

Asp Pro Arg Asn Val Gly Gly Asp Leu Asp Pro Ser Ser Ile Pro Asp
465                 470                 475                 480

Lys Glu Gln Ala Ile Ser Ala Leu Pro Asp Tyr Ala Ser Gln Pro Gly
            485                 490                 495

Lys Pro Pro Arg Glu Asp Leu Lys
            500

<210> SEQ ID NO 5
<211> LENGTH: 446
<212> TYPE: DNA
<213> ORGANISM: Artificial Sequence
<220> FEATURE:
<223> OTHER INFORMATION: synthetic sequence

<400> SEQUENCE: 5
gaattccgaa gtgcagctgg tggaaagcgg cggcggcctg gtgcaggcgg gcggctttct      60
gcgcctgagc tgcgaactgc gcggcagcat ttttaaccag tatgcgatgg gctggtttcg     120
ccaggcgccg ggcaaagaac gcgaatttgt ggcgggcatg ggcgcggtgc gcattatgg     180

```
cgaatttgtg aaaggccgct ttaccattag ccgcgataac gcgaaaagca ccgtgtatct      240
gcagatgagc agcctgaaac cggaagatac cgcgatttat ttttgcgcgc gcagcaaaag      300
cacctatatt agctataaca gcaacggcta tgattattgg ggccgcggca cccaggtgac      360
cgtgagcagc ctgcaggacg tcactagtcc atggcatatg aacagaaac tgatctcaga       420 agaggatctg ctcgaggcgg ccgccc                                           446
```

<210> SEQ ID NO 6
<211> LENGTH: 1495
<212> TYPE: DNA
<213> ORGANISM: Artificial Sequence
<220> FEATURE:
<223> OTHER INFORMATION: Synthetic sequence

<400> SEQUENCE: 6

```
gaattccgaa gtgcagctgg tggaaagcgg cggcggcctg gtgcaggcgg gcggctttct       60
gcgcctgagc tgcgaactgc gcggcagcat ttttaaccag tatgcgatgg gctggtttcg      120
ccaggcgccg ggcaaagaac gcgaatttgt ggcgggcatg ggcgcggtgc gcattatgg      180 cgaatttgtg aaaggccgct ttaccattag ccgcgataac gcgaaaagca ccgtgtatct      240
gcagatgagc agcctgaaac cggaagatac cgcgatttat ttttgcgcgc gcagcaaaag      300
cacctatatt agctataaca gcaacggcta tgattattgg ggccgcggca cccaggtgac      360
cgtgagcagc ctgcaggacg tcactagtcc atggcatatg aacagaaac tgatctcaga       420 agaggatctg ctcgaggcgg ccgccccgga aggtggcagc ctggcagcac tgaccgctca      480
tcaggcatgc cacctgccgc tggaaacctt tacgcgtcat cgtcagccgc gtggctggga      540
acagctggaa caatgtggtt atccggtcca gcgtctggtg gccctgtacc tggcagctcg      600
cctgagctgg aaccaggtgg atcaagttat tcgtaatgca ctggcaagcc cgggttctgg      660
cggtgacctg ggtgaagcga tccgtgaaca gccggaacaa gcacgtctgg cactgaccct      720
ggcagcagca gaaagcgaac gtttcgtgcg ccagggcacg ggtaacgatg aagccggcgc      780
tgcgaatggt ccggctgatt ctggcgacgc gctgctggaa cgtaactatc cgaccggcgc      840
agaatttctg ggtgatggcg tgacgtgtc attctcgacc cgtggcacgc agaattggac       900
ggttgaacgc ctgctgcagg ctcatgcgca actggaagaa cgtggttatg tctttgtggg      960
ctaccacggc accttcctgg aagccgcaca gtcaattgtt tttggcggtg tccgcgctgc     1020
gtcgcaagat ctggccgcaa tttgggccgg cttctacatc gcaggtgacc cggccctggc     1080
atatggctac gcgcaggatc aagaaccgga cgctgcaggt cgtatccgta acggtgctct     1140
gctgcgtgtt tatgtcccgg ccagctctct gccgggtttt taccgtacct cactgacgct     1200
ggcagcaccg gaagctgcag gcgaagtcga acgtctgatt ggtcacccgc tgccgctggc     1260
tctggatgca atcaccggtc cggaagaaga aggcggccgt ctggaaacga ttctgggttg     1320
gccgctggca gaacgcaccg tggttattcc gtccgcgatc ccgaccgacc cgcgcaatgt     1380
tggcggtgat ctggacccga gttccattcc ggataaagaa caggccatca gtgcactgcc     1440
ggactatgcg tcccaaccgg gtaaaccgcc gcgtgaagat ctgaaataac ctagg          1495
```

<210> SEQ ID NO 7
<211> LENGTH: 149
<212> TYPE: PRT
<213> ORGANISM: Artificial Sequence
<220> FEATURE:
<223> OTHER INFORMATION: synthetic sequence -continued

```
<400> SEQUENCE: 7

Pro Asn Ser Glu Val Gln Leu Val Glu Ser Gly Gly Leu Val Gln
1               5                   10                  15

Ala Gly Gly Phe Leu Arg Leu Ser Cys Glu Leu Arg Gly Ser Ile Phe
            20                  25                  30

Asn Gln Tyr Ala Met Gly Trp Phe Arg Gln Ala Pro Gly Lys Glu Arg
        35                  40                  45

Glu Phe Val Ala Gly Met Gly Ala Val Pro His Tyr Gly Glu Phe Val
    50                  55                  60

Lys Gly Arg Phe Thr Ile Ser Arg Asp Asn Ala Lys Ser Thr Val Tyr
65                  70                  75                  80

Leu Gln Met Ser Ser Leu Lys Pro Glu Asp Thr Ala Ile Tyr Phe Cys
                85                  90                  95

Ala Arg Ser Lys Ser Thr Tyr Ile Ser Tyr Asn Ser Asn Gly Tyr Asp
            100                 105                 110

Tyr Trp Gly Arg Gly Thr Gln Val Thr Val Ser Ser Leu Gln Asp Val
        115                 120                 125

Thr Ser Pro Trp His Met Glu Gln Lys Leu Ile Ser Glu Glu Asp Leu
    130                 135                 140

Leu Glu Ala Ala Ala
145

<210> SEQ ID NO 8
<211> LENGTH: 498
<212> TYPE: PRT
<213> ORGANISM: Artificial Sequence
<220> FEATURE:
<223> OTHER INFORMATION: synthetic sequence

<400> SEQUENCE: 8

Pro Asn Ser Glu Val Gln Leu Val Glu Ser Gly Gly Leu Val Gln
1               5                   10                  15

Ala Gly Gly Phe Leu Arg Leu Ser Cys Glu Leu Arg Gly Ser Ile Phe
            20                  25                  30

Asn Gln Tyr Ala Met Gly Trp Phe Arg Gln Ala Pro Gly Lys Glu Arg
        35                  40                  45

Glu Phe Val Ala Gly Met Gly Ala Val Pro His Tyr Gly Glu Phe Val
    50                  55                  60

Lys Gly Arg Phe Thr Ile Ser Arg Asp Asn Ala Lys Ser Thr Val Tyr
65                  70                  75                  80

Leu Gln Met Ser Ser Leu Lys Pro Glu Asp Thr Ala Ile Tyr Phe Cys
                85                  90                  95

Ala Arg Ser Lys Ser Thr Tyr Ile Ser Tyr Asn Ser Asn Gly Tyr Asp
            100                 105                 110

Tyr Trp Gly Arg Gly Thr Gln Val Thr Val Ser Ser Leu Gln Asp Val
        115                 120                 125

Thr Ser Pro Trp His Met Glu Gln Lys Leu Ile Ser Glu Glu Asp Leu
    130                 135                 140

Leu Glu Ala Ala Ala Pro Glu Gly Gly Ser Leu Ala Ala Leu Thr Ala
145                 150                 155                 160

His Gln Ala Cys His Leu Pro Leu Glu Thr Phe Thr Arg His Arg Gln
                165                 170                 175

Pro Arg Gly Trp Glu Gln Leu Glu Gln Cys Gly Tyr Pro Val Gln Arg
            180                 185                 190

Leu Val Ala Leu Tyr Leu Ala Ala Arg Leu Ser Trp Asn Gln Val Asp
```

Gln Val Ile Arg Asn Ala Leu Ala Ser Pro Gly Ser Gly Gly Asp Leu
    210                 215                 220

Gly Glu Ala Ile Arg Glu Gln Pro Glu Gln Ala Arg Leu Ala Leu Thr
225                 230                 235                 240

Leu Ala Ala Ala Glu Ser Glu Arg Phe Val Arg Gln Gly Thr Gly Asn
                245                 250                 255

Asp Glu Ala Gly Ala Ala Asn Gly Pro Ala Asp Ser Gly Asp Ala Leu
            260                 265                 270

Leu Glu Arg Asn Tyr Pro Thr Gly Ala Glu Phe Leu Gly Asp Gly Gly
        275                 280                 285

Asp Val Ser Phe Ser Thr Arg Gly Thr Gln Asn Trp Thr Val Glu Arg
    290                 295                 300

Leu Leu Gln Ala His Ala Gln Leu Glu Gly Arg Gly Tyr Val Phe Val
305                 310                 315                 320

Gly Tyr His Gly Thr Phe Leu Glu Ala Ala Gln Ser Ile Val Phe Gly
                325                 330                 335

Gly Val Arg Ala Ala Ser Gln Asp Leu Ala Ala Ile Trp Ala Gly Phe
            340                 345                 350

Tyr Ile Ala Gly Asp Pro Ala Leu Ala Tyr Gly Tyr Ala Gln Asp Gln
        355                 360                 365

Glu Pro Asp Ala Ala Gly Arg Ile Arg Asn Gly Ala Leu Leu Arg Val
    370                 375                 380

Tyr Val Pro Ala Ser Ser Leu Pro Gly Phe Tyr Arg Thr Ser Leu Thr
385                 390                 395                 400

Leu Ala Ala Pro Glu Ala Ala Gly Glu Val Glu Arg Leu Ile Gly His
                405                 410                 415

Pro Leu Pro Leu Ala Leu Asp Ala Ile Thr Gly Pro Glu Glu Glu Gly
            420                 425                 430

Gly Arg Leu Glu Thr Ile Leu Gly Trp Pro Leu Ala Glu Arg Thr Val
        435                 440                 445

Val Ile Pro Ser Ala Ile Pro Thr Asp Pro Arg Asn Val Gly Gly Asp
    450                 455                 460

Leu Asp Pro Ser Ser Ile Pro Asp Lys Glu Gln Ala Ile Ser Ala Leu
465                 470                 475                 480

Pro Asp Tyr Ala Ser Gln Pro Gly Lys Pro Arg Glu Asp Leu Lys
                485                 490                 495

Pro Arg

<210> SEQ ID NO 9
<211> LENGTH: 39
<212> TYPE: DNA
<213> ORGANISM: Artificial Sequence
<220> FEATURE:
<223> OTHER INFORMATION: synthetic sequence

<400> SEQUENCE: 9
cccgaattca ccatgaaata cgccttagca gacccctcg                    39

<210> SEQ ID NO 10
<211> LENGTH: 48
<212> TYPE: DNA
<213> ORGANISM: Artificial Sequence
<220> FEATURE:
<223> OTHER INFORMATION: synthetic sequence

<400> SEQUENCE: 10
attgcggccg cgttaatggt gatggtgatg gtgcgggttg ctgggggc 48

<210> SEQ ID NO 11
<211> LENGTH: 147
<212> TYPE: PRT
<213> ORGANISM: Artificial Sequence
<220> FEATURE:
<223> OTHER INFORMATION: Synthetic Sequence

<400> SEQUENCE: 11

Met Ala His His His His His Ser Ala Ala Leu Glu Val Leu Phe
1               5                   10                  15

Gln Gly Pro Gly Tyr Gln Asp Pro Asn Ser Glu Val Gln Leu Val Glu
            20                  25                  30

Ser Gly Gly Gly Leu Val Gln Ala Gly Gly Phe Leu Arg Leu Ser Cys
        35                  40                  45

Glu Leu Arg Gly Ser Ile Phe Asn Gln Tyr Ala Met Gly Trp Phe Arg
    50                  55                  60

Gln Ala Pro Gly Lys Glu Arg Glu Phe Val Ala Gly Met Gly Ala Val
65                  70                  75                  80

Pro His Tyr Gly Glu Phe Val Lys Gly Arg Phe Thr Ile Ser Arg Asp
                85                  90                  95

Asn Ala Lys Ser Thr Val Tyr Leu Gln Met Ser Ser Leu Lys Pro Glu
            100                 105                 110

Asp Thr Ala Ile Tyr Phe Cys Ala Arg Ser Lys Ser Thr Tyr Ile Ser
        115                 120                 125

Tyr Asn Ser Asn Gly Tyr Asp Tyr Trp Gly Arg Gly Thr Gln Val Thr
    130                 135                 140

Val Ser Ser
145

<210> SEQ ID NO 12
<211> LENGTH: 521
<212> TYPE: PRT
<213> ORGANISM: Artificial Sequence
<220> FEATURE:
<223> OTHER INFORMATION: Synthetic Sequence

<400> SEQUENCE: 12

Met Ala His His His His His Ser Ala Ala Leu Glu Val Leu Phe
1               5                   10                  15

Gln Gly Pro Gly Tyr Gln Asp Pro Asn Ser Glu Val Gln Leu Val Glu
            20                  25                  30

Ser Gly Gly Gly Leu Val Gln Ala Gly Gly Phe Leu Arg Leu Ser Cys
        35                  40                  45

Glu Leu Arg Gly Ser Ile Phe Asn Gln Tyr Ala Met Gly Trp Phe Arg
    50                  55                  60

Gln Ala Pro Gly Lys Glu Arg Glu Phe Val Ala Gly Met Gly Ala Val
65                  70                  75                  80

Pro His Tyr Gly Glu Phe Val Lys Gly Arg Phe Thr Ile Ser Arg Asp
                85                  90                  95

Asn Ala Lys Ser Thr Val Tyr Leu Gln Met Ser Ser Leu Lys Pro Glu
            100                 105                 110

Asp Thr Ala Ile Tyr Phe Cys Ala Arg Ser Lys Ser Thr Tyr Ile Ser
        115                 120                 125

Tyr Asn Ser Asn Gly Tyr Asp Tyr Trp Gly Arg Gly Thr Gln Val Thr
    130                 135                 140

```
Val Ser Ser Leu Gln Asp Val Thr Ser Pro Trp His Met Glu Gln Lys
145                 150                 155                 160

Leu Ile Ser Glu Glu Asp Leu Leu Glu Ala Ala Pro Glu Gly Gly
            165                 170                 175

Ser Leu Ala Ala Leu Thr Ala His Gln Ala Cys His Leu Pro Leu Glu
            180                 185                 190

Thr Phe Thr Arg His Arg Gln Pro Arg Gly Trp Glu Gln Leu Glu Gln
            195                 200                 205

Cys Gly Tyr Pro Val Gln Arg Leu Val Ala Leu Tyr Leu Ala Ala Arg
            210                 215                 220

Leu Ser Trp Asn Gln Val Asp Gln Val Ile Arg Asn Ala Leu Ala Ser
225                 230                 235                 240

Pro Gly Ser Gly Gly Asp Leu Gly Glu Ala Ile Arg Glu Gln Pro Glu
            245                 250                 255

Gln Ala Arg Leu Ala Leu Thr Leu Ala Ala Glu Ser Glu Arg Phe
            260                 265                 270

Val Arg Gln Gly Thr Gly Asn Asp Glu Ala Gly Ala Ala Asn Gly Pro
            275                 280                 285

Ala Asp Ser Gly Asp Ala Leu Leu Glu Arg Asn Tyr Pro Thr Gly Ala
290                 295                 300

Glu Phe Leu Gly Asp Gly Gly Asp Val Ser Phe Ser Thr Arg Gly Thr
305                 310                 315                 320

Gln Asn Trp Thr Val Glu Arg Leu Leu Gln Ala His Ala Gln Leu Glu
            325                 330                 335

Glu Arg Gly Tyr Val Phe Val Gly Tyr His Gly Thr Phe Leu Glu Ala
            340                 345                 350

Ala Gln Ser Ile Val Phe Gly Gly Val Arg Ala Ala Ser Gln Asp Leu
            355                 360                 365

Ala Ala Ile Trp Ala Gly Phe Tyr Ile Ala Gly Asp Pro Ala Leu Ala
            370                 375                 380

Tyr Gly Tyr Ala Gln Asp Gln Glu Pro Asp Ala Ala Gly Arg Ile Arg
385                 390                 395                 400

Asn Gly Ala Leu Leu Arg Val Tyr Val Pro Ala Ser Ser Leu Pro Gly
            405                 410                 415

Phe Tyr Arg Thr Ser Leu Thr Leu Ala Ala Pro Glu Ala Ala Gly Glu
            420                 425                 430

Val Glu Arg Leu Ile Gly His Pro Leu Pro Leu Ala Leu Asp Ala Ile
            435                 440                 445

Thr Gly Pro Glu Glu Glu Gly Gly Arg Leu Glu Thr Ile Leu Gly Trp
            450                 455                 460

Pro Leu Ala Glu Arg Thr Val Val Ile Pro Ser Ala Ile Pro Thr Asp
465                 470                 475                 480

Pro Arg Asn Val Gly Gly Asp Leu Asp Pro Ser Ser Ile Pro Asp Lys
            485                 490                 495

Glu Gln Ala Ile Ser Ala Leu Pro Asp Tyr Ala Ser Gln Pro Gly Lys
            500                 505                 510

Pro Pro Arg Glu Asp Leu Lys Pro Arg
            515                 520

<210> SEQ ID NO 13
<211> LENGTH: 4
<212> TYPE: PRT
<213> ORGANISM: Artificial Sequence
<220> FEATURE:
```

-continued

<223> OTHER INFORMATION: synthetic sequence

<400> SEQUENCE: 13

Gly Gly Gly Ser
1

<210> SEQ ID NO 14
<211> LENGTH: 19
<212> TYPE: PRT
<213> ORGANISM: Artificial Sequence
<220> FEATURE:
<223> OTHER INFORMATION: synthetic sequence

<400> SEQUENCE: 14

Arg Leu Met Glu Asp Ile Cys Leu Pro Arg Trp Gly Cys Leu Trp Glu
1               5                   10                  15

Asp Asp Phe

<210> SEQ ID NO 15
<211> LENGTH: 126
<212> TYPE: PRT
<213> ORGANISM: Artificial Sequence
<220> FEATURE:
<223> OTHER INFORMATION: synthetic sequence
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (59)..(59)
<223> OTHER INFORMATION: Xaa can be any naturally occurring amino acid

<400> SEQUENCE: 15

Met Ala Glu Val Gln Leu Gln Ala Ser Gly Gly Gly Leu Val Gln Ala
1               5                   10                  15

Gly Gly Ser Leu Arg Leu Ser Cys Xaa Ala Ser Gly Arg Ala Thr Gly
                20                  25                  30

Asn Tyr Pro Met Gly Trp Phe Arg Gln Ala Pro Gly Lys Glu Arg Glu
            35                  40                  45

Phe Val Ala Ala Ile Ser Arg Asp Gly Asp Xaa Thr Tyr Tyr Ala Asp
    50                  55                  60

Ser Val Lys Gly Arg Phe Thr Ile Ser Arg Asp Asn Ala Lys Asn Thr
65                  70                  75                  80

Val Tyr Leu Gln Met Asn Ser Leu Lys Pro Glu Asp Thr Ala Val Tyr
                85                  90                  95

Tyr Cys Ala Ala Asp Arg Leu Thr Ala Tyr Arg Tyr Asn Pro Gly Gln
            100                 105                 110

Ile Asp Tyr Trp Gly Gln Gly Thr Gln Val Thr Val Ser Ser
        115                 120                 125

<210> SEQ ID NO 16
<211> LENGTH: 126
<212> TYPE: PRT
<213> ORGANISM: Artificial Sequence
<220> FEATURE:
<223> OTHER INFORMATION: synthetic sequence

<400> SEQUENCE: 16

Met Ala Glu Val Gln Leu Gln Ala Ser Gly Gly Gly Leu Val Gln Ala
1               5                   10                  15

Gly Gly Ser Leu Arg Leu Ser Cys Ala Ala Ser Gly Arg Ala Thr Gly
                20                  25                  30

Asn Tyr Pro Met Gly Trp Phe Arg Gln Ala Pro Gly Lys Glu Arg Glu
            35                  40                  45

Phe Val Ala Ala Ile Ser Arg Asp Gly Asp Ser Thr Tyr Tyr Ala Asp
 50                  55                  60

Ser Val Lys Gly Arg Phe Thr Ile Ser Arg Asp Asn Ala Lys Asn Thr
 65                  70                  75                  80

Val Tyr Leu Gln Met Asn Ser Leu Lys Pro Glu Asp Thr Ala Val Tyr
                85                  90                  95

Tyr Cys Ala Ala Asp Arg Leu Thr Ala Tyr Arg Tyr Asn Pro Gly Gln
                100                 105                 110

Ile Asp Tyr Trp Gly Gln Gly Thr Gln Val Thr Val Ser Ser
                115                 120                 125

<210> SEQ ID NO 17
<211> LENGTH: 126
<212> TYPE: PRT
<213> ORGANISM: Artificial Sequence
<220> FEATURE:
<223> OTHER INFORMATION: synthetic sequence

<400> SEQUENCE: 17

Met Ala Glu Val Gln Leu Gln Ala Ser Gly Gly Gly Leu Val Gln Ala
 1               5                  10                  15

Gly Gly Ser Leu Arg Leu Ser Cys Ala Ala Ser Gly Arg Ala Thr Gly
                20                  25                  30

Asn Tyr Pro Met Gly Trp Phe Arg Gln Ala Pro Gly Lys Glu Arg Glu
            35                  40                  45

Phe Val Ala Ala Ile Ser Arg Asp Gly Asp Tyr Thr Tyr Tyr Ala Asp
 50                  55                  60

Ser Val Lys Gly Arg Phe Thr Ile Ser Lys Asn Ala Lys Asp Thr
 65                  70                  75                  80

Val Tyr Leu Gln Met Asn Ser Leu Lys Pro Glu Asp Thr Ala Val Tyr
                85                  90                  95

Tyr Cys Thr Ala Asp Arg Leu Thr Ala Tyr Arg Tyr Asn Pro Gly Gln
                100                 105                 110

Ile Asp Tyr Trp Gly Gln Gly Thr Gln Val Thr Val Ser Ser
                115                 120                 125

<210> SEQ ID NO 18
<211> LENGTH: 126
<212> TYPE: PRT
<213> ORGANISM: Artificial Sequence
<220> FEATURE:
<223> OTHER INFORMATION: synthetic sequence

<400> SEQUENCE: 18

Met Ala Glu Val Gln Leu Gln Ala Ser Gly Gly Gly Leu Val Gln Ala
 1               5                  10                  15

Gly Gly Ser Leu Arg Leu Ser Cys Thr Ala Ser Gly Arg Ala Thr Gly
                20                  25                  30

Asn Tyr Pro Met Gly Trp Phe Arg Gln Ala Pro Gly Lys Glu Arg Glu
            35                  40                  45

Phe Val Ala Ala Ile Ser Arg Asp Gly Asp Ser Thr Tyr Tyr Ala Asp
 50                  55                  60

Ser Val Lys Gly Arg Phe Thr Ile Ser Arg Asp Asn Ala Lys Asn Thr
 65                  70                  75                  80

Val Tyr Leu Gln Met Asn Ser Leu Lys Pro Glu Asp Thr Ala Val Tyr

```
                85                  90                  95
Tyr Cys Ala Ala Asp Arg Leu Thr Ala Tyr Arg Tyr Asn Pro Gly Gln
            100                 105                 110

Ile Asp Tyr Trp Gly Gln Gly Thr Gln Val Thr Val Ser Ser
            115                 120                 125

<210> SEQ ID NO 19
<211> LENGTH: 126
<212> TYPE: PRT
<213> ORGANISM: Artificial Sequence
<220> FEATURE:
<223> OTHER INFORMATION: synthetic sequence

<400> SEQUENCE: 19

Met Ala Glu Val Gln Leu Gln Ala Ser Gly Gly Gly Leu Val Gln Ala
1               5                   10                  15

Gly Gly Ser Leu Arg Leu Ser Cys Ala Ala Ser Gly Arg Ala Thr Gly
            20                  25                  30

Asn Tyr Pro Met Gly Trp Phe Arg Gln Ala Pro Gly Lys Glu Arg Glu
        35                  40                  45

Phe Val Ala Ala Ile Ser Arg Asp Gly Asp Tyr Thr Tyr Tyr Ala Asp
    50                  55                  60

Ser Val Lys Gly Arg Phe Thr Ile Ser Lys Asn Asn Ala Lys Asp Thr
65                  70                  75                  80

Val Tyr Leu Gln Met Asn Ser Leu Lys Pro Glu Asp Thr Ala Val Tyr
                85                  90                  95

Tyr Cys Thr Ala Asp Arg Leu Thr Ala Tyr Arg Tyr Asn Pro Gly Gln
            100                 105                 110

Ile Asp Tyr Trp Gly Gln Gly Thr Gln Val Thr Val Ser Ser
            115                 120                 125

<210> SEQ ID NO 20
<211> LENGTH: 126
<212> TYPE: PRT
<213> ORGANISM: Artificial Sequence
<220> FEATURE:
<223> OTHER INFORMATION: synthetic sequence

<400> SEQUENCE: 20

Met Ala Glu Val Gln Leu Gln Ala Ser Gly Gly Gly Leu Val Gln Ala
1               5                   10                  15

Gly Gly Ser Leu Arg Leu Ser Cys Ala Ala Ser Gly Arg Ala Thr Gly
            20                  25                  30

Asn Tyr Pro Met Gly Trp Phe Arg Gln Ala Pro Gly Lys Glu Arg Glu
        35                  40                  45

Phe Val Ala Ala Ile Ser Arg Asp Gly Asp Ser Thr Tyr Tyr Ala Asp
    50                  55                  60

Ser Val Lys Gly Arg Phe Thr Ile Ser Arg Asp Asn Ala Lys Asn Thr
65                  70                  75                  80

Val Tyr Leu Gln Met Asn Ser Leu Lys Pro Glu Asp Thr Ala Val Tyr
                85                  90                  95

Tyr Cys Ala Ala Asp Arg Leu Thr Ala Tyr Arg Tyr Asn Pro Gly Gln
            100                 105                 110

Ile Asp Tyr Trp Gly Gln Gly Thr Gln Val Thr Val Ser Ser
            115                 120                 125

<210> SEQ ID NO 21
<211> LENGTH: 126
```

<212> TYPE: PRT
<213> ORGANISM: Artificial Sequence
<220> FEATURE:
<223> OTHER INFORMATION: synthetic sequence

<400> SEQUENCE: 21

Met Ala Glu Val Gln Leu Gln Ala Ser Gly Gly Gly Leu Val Gln Ala
1               5                   10                  15

Gly Gly Ser Leu Arg Leu Ser Cys Ala Ala Ser Gly Arg Ala Thr Gly
            20                  25                  30

Asn Tyr Pro Met Gly Trp Phe Arg Gln Ala Pro Gly Lys Glu Arg Glu
        35                  40                  45

Phe Val Ala Ala Ile Ser Arg Asp Gly Asp Ser Thr Tyr Tyr Ala Asp
    50                  55                  60

Ser Val Lys Gly Arg Phe Thr Ile Ser Arg Asp Asn Ala Lys Asn Thr
65                  70                  75                  80

Val Tyr Leu Gln Met Asn Ser Leu Lys Pro Glu Asp Thr Ala Val Tyr
                85                  90                  95

Tyr Cys Ala Ala Asp Arg Leu Thr Ala Tyr Arg Tyr Asn Pro Gly Gln
            100                 105                 110

Ile Asp Tyr Trp Gly Gln Gly Thr Gln Val Thr Val Ser Ser
        115                 120                 125

<210> SEQ ID NO 22
<211> LENGTH: 121
<212> TYPE: PRT
<213> ORGANISM: Artificial Sequence
<220> FEATURE:
<223> OTHER INFORMATION: synthetic sequence

<400> SEQUENCE: 22

Met Ala Glu Val Gln Leu Gln Ala Ser Gly Gly Gly Leu Val Gln Pro
1               5                   10                  15

Gly Gly Ser Leu Thr Leu Ser Cys Val Val Thr Gly Ser Pro Ala Glu
            20                  25                  30

Pro Asn Ala Val Gly Trp Tyr Arg Gln Ala Pro Gly Lys Gln Arg Glu
        35                  40                  45

Trp Val Gly Arg Ile Ile Pro Ser Gly Thr Arg Tyr Ala Asp Phe Val
    50                  55                  60

Lys Gly Arg Phe Ile Ile Ser Arg Asp Ser Ala Lys Ser Thr Val Tyr
65                  70                  75                  80

Leu Gln Met Asn Ser Leu Lys Pro Glu Asp Thr Ala Val Tyr Tyr Cys
                85                  90                  95

Ser Pro Leu Thr Gly Ser Gly Thr Tyr Tyr Arg Ser Thr Thr Phe Gly
            100                 105                 110

Gln Gly Thr Gln Val Thr Val Ser Ser
        115                 120

<210> SEQ ID NO 23
<211> LENGTH: 121
<212> TYPE: PRT
<213> ORGANISM: Artificial Sequence
<220> FEATURE:
<223> OTHER INFORMATION: synthetic sequence

<400> SEQUENCE: 23

Met Ala Glu Val Gln Leu Gln Ala Ser Gly Gly Gly Leu Val Gln Pro
1               5                   10                  15

Gly Gly Ser Leu Thr Leu Ser Cys Val Val Thr Gly Ser Pro Ala Glu

-continued

```
                    20                  25                  30
Pro Asn Ala Val Gly Trp Tyr Arg Gln Ala Pro Gly Lys Gln Arg Glu
        35                  40                  45

Trp Val Gly Arg Ile Ile Pro Ser Gly Thr Arg Tyr Ala Asp Phe Val
 50                  55                  60

Lys Gly Arg Phe Ile Ile Ser Arg Asp Ser Ala Lys Ser Thr Val Tyr
 65                  70                  75                  80

Leu Gln Met Asn Ser Leu Lys Pro Glu Asp Thr Ala Ala Tyr Tyr Cys
                85                  90                  95

Ser Pro Leu Thr Gly Ser Gly Thr Tyr Tyr Arg Ser Thr Thr Phe Gly
            100                 105                 110

Gln Gly Thr Gln Val Thr Val Ser Ser
            115                 120

<210> SEQ ID NO 24
<211> LENGTH: 121
<212> TYPE: PRT
<213> ORGANISM: Artificial Sequence
<220> FEATURE:
<223> OTHER INFORMATION: synthetic sequence

<400> SEQUENCE: 24

Met Ala Glu Val Gln Leu Gln Ala Ser Gly Gly Gly Ala Val Glu Val
 1               5                  10                  15

Gly Gly Ser Leu Thr Leu Ser Cys Val Val Thr Gly Ser Pro Ala Glu
                20                  25                  30

Pro Asn Ala Val Gly Trp Tyr Arg Gln Ala Pro Gly Lys Gln Arg Glu
            35                  40                  45

Trp Val Gly Arg Ile Ile Pro Ser Gly Thr Arg Tyr Ala Asp Phe Val
 50                  55                  60

Lys Gly Arg Phe Ile Ile Ser Arg Asp Ser Ala Lys Ser Thr Val Tyr
 65                  70                  75                  80

Leu Gln Met Asn Ser Leu Lys Pro Glu Asp Thr Ala Val Tyr Tyr Cys
                85                  90                  95

Ser Pro Leu Thr Gly Ser Gly Thr Tyr Tyr Arg Ser Thr Thr Phe Gly
            100                 105                 110

Gln Gly Thr Gln Val Thr Val Ser Ser
            115                 120

<210> SEQ ID NO 25
<211> LENGTH: 121
<212> TYPE: PRT
<213> ORGANISM: Artificial Sequence
<220> FEATURE:
<223> OTHER INFORMATION: synthetic sequence

<400> SEQUENCE: 25

Met Ala Glu Val Gln Leu Gln Ala Ser Gly Gly Gly Leu Val Gln Ser
 1               5                  10                  15

Gly Gly Ser Leu Thr Leu Ser Cys Val Val Thr Gly Ser Pro Ala Glu
                20                  25                  30

Pro Asn Ala Val Gly Trp Tyr Arg Gln Ala Pro Gly Lys Gln Arg Glu
            35                  40                  45

Trp Val Gly Arg Ile Ile Pro Ser Gly Thr Arg Tyr Ala Asp Phe Val
 50                  55                  60

Lys Gly Arg Phe Ile Ile Ser Arg Asp Ser Ala Lys Ser Thr Val Tyr
 65                  70                  75                  80
```

```
Leu Gln Met Asn Ser Leu Lys Pro Glu Asp Thr Ala Val Tyr Tyr Cys
                85                  90                  95

Ser Pro Leu Thr Gly Ser Gly Thr Tyr Tyr Arg Ser Thr Phe Gly
            100                 105                 110

Gln Gly Thr Gln Val Thr Val Ser Ser
        115                 120

<210> SEQ ID NO 26
<211> LENGTH: 127
<212> TYPE: PRT
<213> ORGANISM: Artificial Sequence
<220> FEATURE:
<223> OTHER INFORMATION: synthetic sequence

<400> SEQUENCE: 26

Met Ala Glu Val Gln Leu Gln Ala Ser Gly Gly Gly Val Val Gln Pro
1               5                   10                  15

Gly Gly Ser Leu Thr Leu Ser Cys Val Ser Ser Gly Phe Arg Phe Asn
            20                  25                  30

Val Tyr Ala Ile Gly Trp Phe Arg Gln Ala Pro Gly Lys Glu Arg Glu
            35                  40                  45

Ala Val Gly Ala Ile Ser Thr Thr Asp Gly Val Thr Thr Tyr Ala Asp
        50                  55                  60

Ala Val Arg Tyr Arg Phe Ser Ile Thr Arg Asp Arg Ala Lys Asn Thr
65                  70                  75                  80

Val Tyr Leu Gln Met Asn Ser Leu Lys Pro Glu Asp Thr Ala Ile Tyr
                85                  90                  95

Tyr Cys Ala Ala Arg Gly Thr Trp Gly Leu Leu Ser Leu Asp Val Ser
            100                 105                 110

Glu Tyr Gly Tyr Trp Gly Gln Gly Thr Gln Val Thr Val Ser Ser
            115                 120                 125
```

ANTIMICROBIAL COMPOSITIONS COMPRISING SINGLE DOMAIN ANTIBODIES AND PSEUDOMONAS EXOTOXIN

CROSS-REFERENCE TO RELATED APPLICATIONS

This application is a 35 U.S.C. § 371 U.S. national entry of International Application PCT/US2015/010045, having an international filing date of Jan. 2, 2015, which claims the benefit of U.S. Provisional Application No. 61/922,927, filed Jan. 2, 2014, the content of each of the aforementioned applications is herein incorporated by reference in their entirety.

STATEMENT OF GOVERNMENTAL INTEREST

This invention was made with government support under grant no. R21AI079794 awarded by the NIH. The government has certain rights in the invention.

INCORPORATION-BY-REFERENCE OF MATERIAL SUBMITTED ELECTRONICALLY

The instant application contains a Sequence Listing which has been submitted in ASCII format via EFS-Web and is hereby incorporated by reference in its entirety. Said ASCII copy, created on Jan. 3, 2018, is named P12627-03_ST25.txt and is 38,582 bytes in size.

BACKGROUND OF THE INVENTION

The variable domain of heavy-chain only antibodies found in members of the camelid family represents the smallest naturally occurring functional domain of the antibody molecule. These variable domains, termed VHH, have the same antigen binding capability as full-length antibodies, yet are typically around 15 kDa in size. When cloned and purified as monomeric domains, VHH demonstrate remarkable stability under a wide range of denaturing, temperature, and pH conditions. VHHs exhibit increased solubility compared to full-length antibodies or other antibody fragments, and very high expression levels have been achieved in *E. coli*, yeast, and tobacco expression systems. Due to a high degree of sequence homology between camelid and other mammalian variable domains, VHH have been shown not to be immunogenic in mice. As a result of their small size, VHH have enhanced tissue penetration, and an extended CDR3 loop allows VHH access to cryptic epitopes in enzymatically active sites that are unavailable for binding by full length antibodies.

Given their unique combination of characteristics, VHH have been promoted as promising biomedical tools. A myriad of VHH have been successfully developed for diverse purposes including diagnostics, imaging, and biochemical and therapeutic applications. In terms of the diversity of pathogens that have been targeted thus far, VHH directed against viruses, bacteria, protozoa, and fungi have all been identified. VHH can act as a monomeric domain, or they can be expressed in a multivalent context to increase avidity and activity. Additionally, bispecific VHH can be assembled that bind different epitopes, which can in some cases dramatically increasing neutralization efficacy.

HSV-2 is one of the most prevalent sexually transmitted infections (STIs) in the world, and recent estimates indicate that roughly 16% of people ages 15-49 worldwide are infected. There has been great interest in the development of a prophylactic vaccine to prevent HSV-2 infection over the past several decades, but unfortunately, an effective one has yet to be developed.

Human immunodeficiency virus type I (HIV-1) is also a sexually transmitted infection, and has contributed to an estimated 40 million deaths since it was first recognized in 1981. Currently, over 30 million people worldwide are living with the virus. The development of effective HIV-1 vaccine immunogens that can elicit high titer, potent, and broadly neutralizing antibodies (bnAbs) remains a major challenge.

Entry of HIV-1 into target cells is mediated by binding of highly conserved epitopes on HIV envelope glycoproteins (Env) to a primary cell-surface receptor CD4. Binding of Env to CD4 initiates a series of conformational changes of the Env structure, leading to exposure and/or formation of coreceptor binding sites that are recognized by cell surface co-receptors (e.g. chemokine receptors CCR5 or CXCR4). Since HIV-1 was first discovered more than two decades ago, conventional vaccine strategies have failed to develop effective vaccine candidates that can elicit potent broadly cross-reactive HIV-1-neutralizing antibodies. There continues to be a pressing need for novel HIV vaccine strategies and compositions that can control the spread of HIV/AIDS pandemic.

A microbicide is a substance that can be applied to mucosal surfaces, including the vagina and rectum, to prevent infection with an STI. A significant public health goal has been to try develop a successful microbicide against HSV-2 and HIV-1, including vaginal delivery of antiviral drugs, antibody-based strategies, and small-interfering RNAs. It has been demonstrated that vaginally applied monoclonal antibodies and single chain antibody variable fragments (scFv) directed against gD2 protect against HSV-2 infection in animal models. The issue of how to vaginally deliver a neutralizing antibody against HSV2 or HIV-1 without the direct application of the antibody immediately prior to sexual intercourse has yet to be resolved, however. Furthermore, the current methods of production of monoclonal antibodies and scFvs can be cost-prohibitive to scale up, as antibodies are complex molecules with multiple protein chains that are not easily purified and assembled.

As a result, there still exists an unmet need for alternative strategies to prevent transmission, including the development of an effective microbicide using means other than scFvs.

SUMMARY OF THE INVENTION

The isolation of an antibody fragment that neutralizes HSV-2 or HIV-1, and is structurally simple enough to be produced by the native bacterial flora of the vagina would solve both the production and delivery challenges of the antibody-based microbicide strategy. Members of the Camelid family (camels, alpacas, and llamas), naturally produce antibodies that are devoid of light chains, so that the antigen binding region is solely contained in the variable region of the heavy chain, referred to as VHH (FIG. 1). These VHH domains retain the potent binding capacity of full-length antibodies, are stable under a wide range of temperature and pH conditions, and are not immunogenic. Another attractive characteristic of VHH antibodies is that they are small enough to be secreted by many types of commensal bacteria, including, for example, Lactobacilli, an ideal organism for delivery of VHH antibodies because they are a major component of the vaginal flora and because systems for expression of heterologous proteins have been developed for these bacteria.

Using a VHH antibody that bound to gD2 of HSV-2, in an embodiment, the inventors created a *P. aeruginosa* Exotoxin A (PE)-based immunotoxin that specifically targets HSV-2 infected cells. This immunotoxin specifically binds to cells expressing gD2 at the cell surface, causing internalization of the entire protein, allowing the exotoxin A portion to act by halting protein synthesis, ultimately resulting in cell death.

In accordance with an embodiment, the present invention provides a heavy chain immunoglobulin of the VHH type or fragment thereof having an amino acid sequence of at least 85% identity to SEQ ID NO: 3 (R33) and having affinity for glycoprotein D2 (gD2) of HSV-2 or antigen thereof.

In accordance with another embodiment, the present invention provides a heavy chain immunoglobulin of the VHH type or fragment thereof having an amino acid sequence of at least 85% identity to SEQ ID NO: 4 (R33) and having affinity for glycoprotein D2 (gD2) of HSV-2 or antigen thereof that is covalently linked to the *P. aeruginosa* Exotoxin A subunit or a functional portion or fragment thereof.

In accordance with a further embodiment, the present invention provides a multimeric molecule comprising a heavy chain immunoglobulin fragment of the VHH type as described herein, in which VHH sequences are fused to yield multimeric units of 2 or more VHH units optionally linked via a spacer molecule.

In accordance with still another embodiment, the present invention provides a multimeric molecule comprising two or more VHH sequences as described herein, which are fused to yield 2, 3, 4 or 5 or more VHH units optionally linked via a spacer molecule.

In accordance with an embodiment, the present invention provides a nucleic acid encoding a heavy chain immunoglobulin fragment of the VHH type as described herein.

In accordance with another embodiment, the present invention provides an expression vector comprising the gene encoding the heavy chain immunoglobulin fragment described herein.

In accordance with still another embodiment, the present invention provides a micro-organism transformed with the expression vector described herein.

In accordance with a further embodiment, the present invention provides a method for the therapy or prophylaxis of HSV2 infection, comprising administering to a patient a heavy chain immunoglobulin or fragment thereof described herein or the multimeric molecule described herein.

In accordance with another embodiment, the present invention provides a method for the therapy or prophylaxis of HSV2 infection, comprising administering to a patient a micro-organism described herein expressing the heavy chain immunoglobulin or fragment thereof described herein, or the multimeric molecule described herein. In some embodiments the multimeric molecule comprises the amino acid sequence of SEQ ID NO: 4.

In accordance with another embodiment, the present invention provides a heavy chain immunoglobulin of the VHH type or fragment thereof comprising an amino acid sequence of at least 85% identity to SEQ ID NOS. 7 or 11, and having affinity for envelope proteins of HIV-1.

In accordance with yet another embodiment, the present invention provides a heavy chain immunoglobulin of the VHH type or fragment thereof comprising an amino acid sequence of at least 85% identity to SEQ ID NOS. 8 or 12, and having affinity for envelope proteins of HIV-1 which is covalently linked to the *P. aeruginosa* Exotoxin A subunit or functional portion or fragment thereof.

In accordance with still another embodiment, the present invention provides a multimeric molecule comprising a heavy chain immunoglobulin fragment of the VHH type described herein, in which VHH sequences are fused to yield multimeric units of 2 or more VHH units optionally linked via a spacer molecule.

In accordance with a further embodiment, the present invention provides a multimeric molecule comprising two or more VHH sequences described herein, which are fused to yield 2, 3, 4 or 5 or more VHH units optionally linked via a spacer molecule.

In accordance with an embodiment, the present invention provides a nucleic acid encoding a heavy chain immunoglobulin fragment of the VHH type and having affinity for envelope proteins of HIV-1 which is covalently linked to the *P. aeruginosa* Exotoxin A subunit comprising the nucleic acid sequence of SEQ ID NO: 6.

In accordance with a further embodiment, the present invention provides an expression vector comprising the gene encoding the heavy chain immunoglobulin fragment and having affinity for envelope proteins of HIV-1 which is covalently linked to the *P. aeruginosa* Exotoxin A subunit or functional portion or fragment thereof.

In accordance with an embodiment, the present invention provides a method for the therapy or prophylaxis of HIV-1 infection, comprising administering to a patient a heavy chain immunoglobulin or fragment thereof having affinity for envelope proteins of HIV-1 which is covalently linked to the *P. aeruginosa* Exotoxin A subunit or functional portion or fragment thereof, or the multimeric molecule of described herein.

In accordance with another embodiment, the present invention provides a method for the therapy or prophylaxis of HIV-1 infection, comprising administering to a patient a micro-organism expressing the heavy chain immunoglobulin or fragment thereof and having affinity for envelope proteins of HIV-1 or an antigen thereof that is covalently linked to the *P. aeruginosa* Exotoxin A subunit or functional portion or fragment thereof, or the multimeric molecule described herein.

BRIEF DESCRIPTION OF THE DRAWINGS

FIG. 6 depicts amplification of VHH regions from llama DNA. After the final immunization, PBMCs were separated from whole blood and RNA was purified for synthesis of cDNA. Nested primer sets were used to amplify the variable region from heavy chain only antibodies (VHH) from the cDNA, and PCR products were separated by agarose gel electrophoresis. Labels indicate which llama and round of PCR the sample is derived from.

FIG. 12 illustrates a unique VHH amino acid sequence alignment. VHH inserts, originally amplified from variable region of heavy chain only antibodies, were sequenced from VHH-phage clones and aligned to determine unique VHH sequences identified from the gD2 biopanning process. The consensus sequence is listed in the Sequence Listing as SEQ ID NO: 15. Sequences No. 2-1 to No. 2-39 are listed as in the Sequence Listing as SEQ ID NOS: 16-21 respectively. Sequences No. 1-1 to No. 1-10 are listed as in the Sequence Listing as SEQ ID NOS: 22-26 respectively.

FIG. 22 depicts a nucleic acid sequence (22A) and an amino acid sequence (22B) for an embodiment of the VHHR33ExoA construct of the present invention.

FIG. 23 depicts a nucleic acid sequence (23A) and an amino acid sequence (23B) for an embodiment of the J3VHHExoA construct of the present invention.

FIG. 24 depicts the amino acid sequence of an embodiment of the present invention comprising fully expressed J3VHH construct (SEQ ID NO: 11) and the J3VHHExoA construct (SEQ ID NO: 12). The figures show the annotated protein sequence of insert containing J3 VHH fused to Exotoxin A Key: Gray highlight signifies the start codon; Purple Highlight is the His Tag; Highlighted yellow regions contain restriction sites; 5' end EcoR1; 3' end AvrII; Underlined sequence is the J3 VHH; Italicized sequence is the linker region; Includes yellow highlighted multiple cloning site sequence; Includes myc tag highlighted in blue; Bold sequence is the *P. aeruginosa* Exotoxin A subunit; Red highlight is the stop codon.

DETAILED DESCRIPTION OF THE INVENTION

Figure 1:
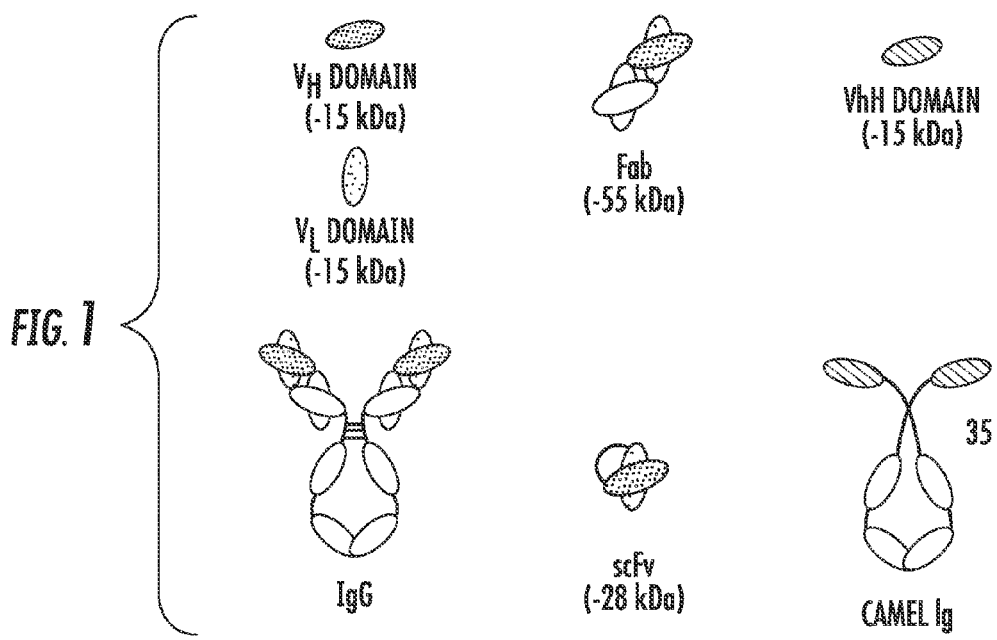
FIG. 1 illustrates the structural comparison of human and camelid antibodies and antibody fragments. Adapted from Holliger & Hudson 2005.

In accordance with an embodiment, the present invention provides a heavy chain immunoglobulin of the VHH type or fragment thereof having an amino acid sequence of at least 85% identity to SEQ ID NO. 3 (R33) and having affinity for glycoprotein D 2 (gD2) of HSV-2 or antigen thereof.

As used herein, the term "heavy chain immunoglobulin of the VHH type or fragment thereof" means the variable domain of heavy-chain only antibodies found in members of the camelid family, and which represents the smallest naturally occurring functional domain of the antibody molecule. These variable domains, termed VHH, have the same antigen binding capability as full-length antibodies, yet are typically around 15 kDa in size. As a result of their small size, VHH have enhanced tissue penetration, and an extended CDR3 loop allows VHH access to cryptic epitopes in enzymatically active sites that are unavailable for binding by full length antibodies.

VHH can act as a monomeric domain, or they can be expressed in a multivalent context to increase avidity and activity. Additionally, bispecific VHH can be assembled that bind different epitopes, which can in some cases dramatically increasing neutralization efficacy.

VHH can also serve as carriers for other molecules through conjugation or expression as a fusion protein with an effector domain to create an immunoconjugate.

As used herein, the term "immunoconjugate" is a conjugate of a binding molecule (e.g., an antibody) with an atom, molecule, or a higher-ordered structure (e.g., with a liposome), and an antigen, and/or therapeutic agent, and/or a diagnostic agent.

The term "antigen" or "antigenic epitope" as used herein refers to any molecule (e.g., protein, peptide, lipid, carbohydrate, etc.) solely or predominantly expressed or overexpressed by a target cell of interest, such that the antigen is associated with the target cell.

In accordance with another embodiment, the present invention provides a heavy chain immunoglobulin of the VHH type or fragment thereof having an amino acid sequence of at least 85% identity to SEQ ID NO. 4 (R33) and having affinity for glycoprotein D 2 (gD2) of HSV-2 or antigen thereof that is covalently linked to the *P. aeruginosa* Exotoxin A subunit.

The term "polypeptide" as used herein includes oligopeptides and refers to a single chain of amino acids connected by one or more peptide bonds.

The term "a peptide or polypeptide fragment thereof, capable of being cleaved by a specific protease" as used herein, means an amino acid sequence which is specifically recognized by a protease enzyme and specifically binds and hydrolytically cleaves that amino acid sequence. The peptide sequence can be any sequence of between about 3 to about 20 amino acids in length, which is known to be cleaved by a known protease. In one or more embodiments, the present invention provides an immunoconjugate where the peptide or polypeptide fragment thereof, capable of being cleaved by a specific protease is an amino acid sequence cleaved by a protease normally found on cancer cell membranes. Preferably, the protease is furin, which is found on many types of tumor cells.

The term "functional portion" when used in reference to a monoclonal antibody or antigenic epitope refers to any part or fragment, which part or fragment retains the biological activity of which it is a part (the parent molecule, antibody, or antigen). Functional portions encompass, for example, those parts that retain the ability to specifically bind to the antigen (e.g., in an MHC-independent manner), or detect, treat, or prevent the disease, to a similar extent, the same extent, or to a higher extent, as the parent molecule. In reference to the parent molecule, the functional portion can comprise, for instance, about 10%, 25%, 30%, 50%, 68%, 80%, 90%, 95%, or more, of the parent molecule.

The functional portion can comprise additional amino acids at the amino or carboxy terminus of the portion, or at both termini, which additional amino acids are not found in the amino acid sequence of the parent molecule. Desirably, the additional amino acids do not interfere with the biological function of the functional portion, e.g., specifically binding to a cancer antigen, having the ability to detect cancer, treat or prevent cancer, etc. More desirably, the additional amino acids enhance the biological activity, as compared to the biological activity of the parent molecule.

By "protein" is meant a molecule comprising one or more polypeptide chains.

In this regard, the invention also provides an immunoconjugate molecule comprising at least one of the polypeptides described herein along with at least one other polypeptide. The other polypeptide can exist as a separate polypeptide of the fusion protein, or can exist as a polypeptide, which is expressed in frame (in tandem) with one of the inventive polypeptides described herein. The other polypeptide can encode any peptidic or proteinaceous molecule, or a portion thereof. Suitable methods of making fusion proteins are known in the art, and include, for example, recombinant methods. See, for instance, Choi et al., *Mol. Biotechnol.* 31: 193-202 (2005).

As used herein, "recombinant antibody" refers to a recombinant (e.g., genetically engineered) protein comprising at least one of the polypeptides of the invention and a polypeptide chain of an antibody, or a portion thereof. The polypeptide of an antibody, or portion thereof, and is a heavy chain immunoglobulin of the VHH type or fragment thereof. The polypeptide chain of an antibody, or portion thereof, can exist as a separate polypeptide of the recombinant antibody. Alternatively, the polypeptide chain of an antibody, or portion thereof, can exist as a polypeptide, which is expressed in frame (in tandem) with the polypeptide of the invention. The polypeptide of an antibody, or portion thereof, can be a polypeptide of any antibody or any antibody fragment, including any of the antibodies and antibody fragments described herein.

In accordance with an embodiment, the VHH portion of the immunoconjugate can be directed to other well-known proteins highly expressed on other target cells when compared to normal cells in the body. Examples of such proteins include, without limitation, envelope proteins of HIV-1 and others known in the art.

In accordance with another embodiment, the present invention provides a heavy chain immunoglobulin of the VHH type or fragment thereof comprising an amino acid sequence of at least 85% identity to SEQ ID NOS. 7 or 11, and having affinity for envelope proteins of HIV-1.

In accordance with yet another embodiment, the present invention provides a heavy chain immunoglobulin of the VHH type or fragment thereof comprising an amino acid sequence of at least 85% identity to SEQ ID NOS. 8 or 12, and having affinity for envelope proteins of HIV-1 which is covalently linked to the *P. aeruginosa* Exotoxin A subunit or functional portion or fragment thereof.

Included in the scope of the invention are functional variants of the inventive immunoconjugate, and polypeptides, and proteins described herein. The term "functional variant" as used herein refers to an immunoconjugate, polypeptide, or protein having substantial or significant sequence identity or similarity to a parent immunoconjugate, polypeptide, or protein, which functional variant retains the biological activity of the immunoconjugate, polypeptide, or protein of which it is a variant. In reference to the parent immunoconjugate, polypeptide, or protein, the functional variant can, for instance, be at least about 30%, 50%, 75%, 80%, 90%, 98% or more identical in amino acid sequence to the parent immunoconjugate, polypeptide, or protein.

The functional variant can, for example, comprise the amino acid sequence of the parent immunoconjugate, polypeptide, or protein with at least one conservative amino acid substitution. Conservative amino acid substitutions are known in the art, and include amino acid substitutions in which one amino acid having certain physical and/or chemical properties is exchanged for another amino acid that has the same chemical or physical properties. For instance, the conservative amino acid substitution can be an acidic amino acid substituted for another acidic amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Val, etc.), a basic amino acid substituted for another basic amino acid (Lys, Arg, etc.), an amino acid with a polar side chain substituted for another amino acid with a polar side chain (Asn, Cys, Gln, Ser, Thr, Tyr, etc.), etc Alternatively or additionally, the functional variants can comprise the amino acid sequence of the parent immunoconjugate, polypeptide, or protein with at least one non-conservative amino acid substitution. In this case, it is preferable for the non-conservative amino acid substitution to not interfere with or inhibit the biological activity of the functional variant. Preferably, the non-conservative amino acid substitution enhances the biological activity of the functional variant, such that the biological activity of the functional variant is increased as compared to the parent immunoconjugate, polypeptide, or protein.

The immunoconjugate, polypeptide, and/or protein of the invention (including functional portions and functional variants thereof) can be obtained by methods known in the art. Suitable methods of de novo synthesizing polypeptides and proteins are described in references, such as Chan et al., Fmoc Solid Phase Peptide Synthesis, Oxford University Press, Oxford, United Kingdom, 2005; Peptide and Protein Drug Analysis, ed. Reid, R., Marcel Dekker, Inc., 2000; Epitope Mapping, ed. Westwoood et al., Oxford University Press, Oxford, United Kingdom, 2000; and U.S. Pat. No. 5,449,752. Also, polypeptides and proteins can be recombinantly produced using the nucleic acids described herein using standard recombinant methods. See, for instance, Sambrook et al., Molecular Cloning: A Laboratory Manual, 3rd ed., Cold Spring Harbor Press, Cold Spring Harbor, N.Y. 2001; and Ausubel et al., Current Protocols in Molecular Biology, Greene Publishing Associates and John Wiley & Sons, N Y, 1994. Further, some of the immunoconjugates, polypeptides, and proteins of the invention (including functional portions and functional variants thereof) can be isolated and/or purified from a source, such as a plant, a bacterium, an insect, a mammal, e.g., a rat, a human, etc. Methods of isolation and purification are well-known in the art. Alternatively, the immunoconjugates, polypeptides, and/or proteins described herein (including functional portions and functional variants thereof) can be commercially synthesized by companies, such as Synpep (Dublin, Calif.), Peptide Technologies Corp. (Gaithersburg, Md.), and Multiple Peptide Systems (San Diego, Calif.). In this respect, the inventive immunoconjugates, polypeptides, and proteins can be synthetic, recombinant, isolated, and/or purified.

In accordance with yet another embodiment, the present invention provides a nucleic acid molecule which encodes the immunoconjugates described above.

For example, the present invention includes nucleic acid molecules comprising SEQ ID NOS: 1, 2, 5 and 6.

Further provided by the invention is a nucleic acid comprising a nucleotide sequence encoding any of the immunoconjugates, polypeptides, or proteins described herein (including functional portions and functional variants thereof).

By "nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. It is generally preferred that the nucleic acid does not comprise any insertions, deletions, inversions, and/or substitutions. However, it may be suitable in some instances, as discussed herein, for the nucleic acid to comprise one or more insertions, deletions, inversions, and/or substitutions.

Preferably, the nucleic acids of the invention are recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

The nucleic acids can be constructed based on chemical synthesis and/or enzymatic ligation reactions using procedures known in the art. See, for example, Sambrook et al., supra, and Ausubel et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Macromolecular Resources (Fort Collins, Colo.) and Synthegen (Houston, Tex.).

In some embodiments, the substituted nucleic acid sequence may be optimized. Without being bound to a particular theory, it is believed that optimization of the nucleic acid sequence increases the translation efficiency of the mRNA transcripts. Optimization of the nucleic acid sequence may involve substituting a native codon for another codon that encodes the same amino acid, but can be translated by tRNA that is more readily available within a cell, thus increasing translation efficiency. Optimization of the nucleic acid sequence may also reduce secondary mRNA structures that would interfere with translation, thus increasing translation efficiency.

The invention also provides an isolated or purified nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

In accordance with still a further embodiment, the present invention provides a plasmid which comprises a nucleic acid molecule which encodes the immunoconjugates described herein. In accordance with some embodiments, the plasmid constructs of the present invention The nucleic acids of the invention can be incorporated into a recombinant expression vector. In this regard, the invention provides recombinant expression vectors comprising any of the nucleic acids of the invention. For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the invention are not naturally-occurring as a whole. However, parts of the vectors can be naturally-occurring. The inventive recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring, non-naturally-occurring internucleotide linkages, or both types of linkages. Preferably, the non-naturally occurring or altered nucleotides or internucleotide linkages do not hinder the transcription or replication of the vector.

The recombinant expression vector of the invention can be any suitable recombinant expression vector, and can be used to transform or transfect any suitable host. Suitable vectors include those designed for propagation and expansion or for expression or both, such as plasmids and viruses. The vector can be selected from the group consisting of the pUC series (Fermentas Life Sciences), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGT10, λGT11, λZapII (Stratagene), λEMBL4, and λNM1149, also can be used. Examples of plant expression vectors include pBI01, pBI101.2, pBI101.3, pBI121 and pBIN19 (Clontech). Examples of animal expression vectors include pEUK-C1, pMAM and pMAMneo (Clontech). Preferably, the recombinant expression vector is a viral vector, e.g., a retroviral vector.

The recombinant expression vectors of the invention can be prepared using standard recombinant DNA techniques described in, for example, Sambrook et al., supra, and Ausubel et al., supra. Constructs of expression vectors, which are circular or linear, can be prepared to contain a replication system functional in a prokaryotic or eukaryotic host cell. Replication systems can be derived, e.g., from ColE1, 2μ plasmid, λ, SV40, bovine papilloma virus, and the like.

Desirably, the recombinant expression vector comprises regulatory sequences, such as transcription and translation initiation and termination codons, which are specific to the type of host (e.g., bacterium, fungus, plant, or animal) into which the vector is to be introduced, as appropriate and taking into consideration whether the vector is DNA- or RNA-based.

The recombinant expression vector can include one or more marker genes, which allow for selection of transformed or transfected hosts. Marker genes include biocide resistance, e.g., resistance to antibiotics, heavy metals, etc., complementation in an auxotrophic host to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

It will be understood by those of ordinary skill in the art that the recombinant vectors which can be used to express the immunoconjugates of the present invention can be used to transfect any species of bacteria that are capable of colonizing the vagina or other orifices of the body of a subject. A common example of such a species of bacteria is *Lactobacillus*, including, for example, *L. jensenii, L. reuteri, L. gasseri, L. crispatus*, and *L. iners*, or other *lactobacillus* or *lactococcus* species that may colonize the human vagina.

The recombinant expression vector can comprise a native or nonnative promoter operably linked to the nucleotide sequence encoding the immunoconjugate, polypeptide, or protein (including functional portions and functional variants thereof), or to the nucleotide sequence which is complementary to or which hybridizes to the nucleotide sequence encoding the immunoconjugate, polypeptide, or protein. The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter, and a promoter found in the long-terminal repeat of the murine stem cell virus.

The antibody can be in monomeric or polymeric form. Also, the antibody or fragments thereof, can have any level of affinity or avidity for the target cell or population of cell antigen(s). Desirably, the antibody is specific for the functional portion of the target cell or population of cells, such that there is minimal cross-reaction with other cells or populations of cells.

Methods for generating humanized antibodies are well known in the art and are described in detail in, for example, Janeway et al., supra, U.S. Pat. Nos. 5,225,539, 5,585,089 and 5,693,761, European Patent No. 0239400 B1, and United Kingdom Patent No. 2188638. Humanized antibodies can also be generated using the antibody resurfacing technology described in U.S. Pat. No. 5,639,641 and Pedersen et al., J. Mol. Biol., 235, 959-973 (1994).

The invention also provides antigen binding portions of any of the antibodies described herein.

Also, the antibody, or antigen binding portion thereof, can be modified to comprise a detectable label, such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

It will be understood by those of ordinary skill in the art that the embodiments of VHH linked immunotoxin can be used in multiple ways. If applied vaginally, an anti-gD2 immunoconjugate could prevent HSV-2 infection by killing infected epithelial cells prior to establishment of latency. Thus, the immunotoxins of the present invention have the potential to not only act as a microbicides to prevent initial infection, but can also act to reduce viral shedding in infected individuals by eliminating gD2-expressing cells during reactivation of the virus from latency.

In accordance with a further embodiment, the present invention provides a method for treating HSV2 in a subject, comprising administering to the subject, a therapeutically effective amount of the immunoconjugate described above and a pharmaceutically acceptable carrier.

In accordance with a further embodiment, the present invention provides a method for treating HIV-1 in a subject, comprising administering to the subject, a therapeutically effective amount of the immunoconjugate described above and a pharmaceutically acceptable carrier.

It will be understood by those of skill in the art that one of the mechanisms by which HIV-1 and HIV-2 escape elimination by the host immune system is by the HIV-1 genome residing within resting or inactive immune cells without expressing viral proteins that can be recognized by the immune system. One embodiment for curing HIV-1 infection would be to activate those resting cells so that the virus then expresses proteins that will appear on the surface of the infected cells either as peptides in association with MHC molecules or as native proteins which accumulate on the cell surface as part of the virus assembly process. Once expressed on the cell surface these proteins can serve as targets for immunotoxins so that the infected cells can be eliminated. As such, an example of compounds that might be used for activating resting cells and activating latent virus would be histone deacetylation (HDAC) inhibitors. To be most effective against a broad range of HIV-1 variants, a VHH exotoxin A fusion protein of the present invention should target a highly conserved region of the viral envelope, which is typically expressed on the surface of activated, HIV-1 expressing cells. A VHH with such broad specificity has been identified (J Exp Med 209:1091-1103 (2012). In an embodiment, a method of treatment of HIV would include administration of HDAC inhibitors to HIV-1 infected people who are concurrently receiving antiretroviral therapy, and who would then be administered the VHH exotoxin A of the present invention by the intravenous route using a dose of the preparation that would avoid non-specific toxicity but would kill HIV infected cells expressing the conserved region of the envelope protein. The lack of non-specific toxicity is attained by linking the toxin covalently to the VHH that only targets the toxin to infected cells.

In some embodiments, the binding affinity of the VHH will be enhanced by converting it from a monovalent to a bivalent VHH (bvJ3). This will be done, by using appropriate primer sets to amplify a second J3 sequence and incorporate a GS linker between the two J3 sequences. DNA encoding the 38 kd fragment of ExoA will then be cloned in frame to the C terminus of the VHH. Using dilution series, we will then test the relative killing activity of the bvJ3-ExoA and J3-ExoA using the Env+ and Env-CHO cell lines. The expectation is that the bvJ3-ExoA will be active at lower concentrations. A similar construct will be developed using the active fragment of diphtheria toxin.

In some other embodiments, due to the short in vivo half-life of circulating VHH, we can further modify these constructs by fusing them via a linker sequence (such as GGGS) to DNA encoding the albumin binding peptide RLMEDICLPRWGCLWEDDF (ABP) (SEQ ID NO: 14). Previous studies with this peptide have fused it to the C terminal end of scFv with resulting a 5-6 fold increase in the half-life of the associated protein. We will produce constructs in which the peptide is placed with or without linker sequences before or after the ExoA component of the VHH-ExoA construct. Efficacy will again be studied using the Env+ and Env- CHO cell lines. If bioactivity of the albumin-binding construct is confirmed, its albumin binding will be evaluated by ELISA, testing the binding of the ABP-VHH-ExoA construct in wells coated with albumin vs. control wells, as described, using antibodies targeting the His-tag incorporated into the VHH construct for ELISA development.

In accordance with some other embodiments, the exotoxin can be administered subcutaneously by being incorporated into sustained delivery particles. For example, the Medusa® drug delivery platform consists of proprietary depot hydrogels for the formulation and/or the extended release of a broad range of biologics (including proteins, antibodies, peptides and vaccines) and of small molecules (injectable drugs). These hydrogels have been proven to be safe and biodegradable. Medusa enables the controlled delivery from 1 day up to 14 days of non-denatured or non-modified drugs that maintain full bioactivity. The in vivo efficacy of the embodiments can be confirmed by Western blotting of serum obtained from mice at different time points post administration of either the "native" J3-ExoA or J3-ExoA administered in an extended release format.

The immunoconjugates of the present invention can be formulated into a composition, such as a pharmaceutical composition. In this regard, the invention provides a pharmaceutical composition comprising any of the immunoconjugates, polypeptides, proteins, functional portions, functional variants, nucleic acids, expression vectors, and a pharmaceutically acceptable carrier. The inventive pharmaceutical compositions containing any of the inventive immunoconjugates can comprise more than one immunoconjugate.

Preferably, the carrier is a pharmaceutically acceptable carrier. With respect to pharmaceutical compositions, the carrier can be any of those conventionally used and is limited only by chemico-physical considerations, such as solubility and lack of reactivity with the active compound(s), and by the route of administration. The pharmaceutically acceptable carriers described herein, for example, vehicles, adjuvants, excipients, and diluents, are well-known to those skilled in the art and are readily available to the public. It is preferred that the pharmaceutically acceptable carrier be one which is chemically inert to the active agent(s) and one which has no detrimental side effects or toxicity under the conditions of use.

The choice of carrier will be determined in part by the particular immunoconjugate, as well as by the particular method used to administer the immunoconjugate. Accordingly, there are a variety of suitable formulations of the pharmaceutical composition of the invention. The following formulations for aerosol, parenteral, subcutaneous, interperitoneal, vaginal and rectal, administration are exemplary and are in no way limiting. More than one route can be used to administer the immunoconjugate, and in certain instances, a particular route can provide a more immediate and more effective response than another route. For treatment of HSV2, the preferred route is vaginal.

It will be appreciated by one of skill in the art that, in addition to the above-described pharmaceutical compositions, the immunoconjugate of the invention can be formulated as inclusion complexes, such as cyclodextrin inclusion complexes, or liposomes.

For purposes of the invention, the amount or dose of the immunoconjugate administered should be sufficient to effect, e.g., a therapeutic or prophylactic response, in the subject or animal over a reasonable time frame. For example, the dose of the immunoconjugate should be sufficient to bind to a target antigen, or detect, treat or prevent an infection in a period of from about 2 hours or longer, e.g., 12 to 24 or more hours, from the time of administration. In certain embodiments, the time period could be even longer. The dose will be determined by the efficacy of the particular immunoconjugate and the condition of the animal (e.g., human), as well as the body weight of the animal (e.g., human) to be treated. In some embodiments, multiple administrations of the immunoconjugate can be required to effect elimination of the viral burden in the subject. For example, there may be an initial dose followed by a period of time where the viral or tumor burden is monitored and then subsequent dosages of the immunoconjugate are given in an iterative fashion.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of cancer in a mammal. Furthermore, the treatment or prevention provided by the inventive method can include treatment or prevention of one or more conditions or symptoms of the disease, e.g., cancer, being treated or prevented. Also, for purposes herein, "prevention" can encompass delaying the onset of the disease, or a symptom or condition thereof.

As used herein, the term "subject" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

EXAMPLES

Expression and Purification of Recombinant his-gD2 from *Pichia pastoris*

Using genomic DNA from HSV-2 186 as a template, amino acids 1-314 of gD2 (ectodomain) were amplified from the viral genome using primers (forward)

```
                                           (SEQ ID NO: 9)
   CCCGAATTCACCATGAAATACGCCTTAGCAGACCCCTCG
``` and (reverse)

```
                                          (SEQ ID NO: 10)
ATTGCGGCCGCGTTAatggtgatggtgatggtgCGGGTTGCTGGGGGC,
``` which also added a His tag to the C-terminus. The gD2 sequence was cloned into the expression vector pPIC9 and transformed into *Pichia pastoris* by electroporation. A midscale culture (~30 mL) of Buffered Glycerol-complex Media (BMGY) was inoculated with 500 µL of a gD2/*P. pastoris* glycerol stock and grown at 30° C. shaking at 225 rpm for ~48 hours, until the cultures reaches an $OD_{600}$ of 2-6. The culture was then diluted in 700 mL of BMGY media and grown in a 2 L-baffled flask at 30° C. with shaking at 225 rpm until the $OD_{600}$ reached 50. Cells were harvested in sterile centrifuge bottles at 2500 g for 20 minutes at room temperature (RT). To induce expression, the cell pellet was resuspended in 200 mL of Buffered Methanol-complex Media (BMMY) and grown for 48 hours at 30° C. with shaking at 225 rpm. Cells were harvested by centrifugation at 1500-3000 g and supernatant was collected; 2 mL Ni- NTA Superflow Resin (QIAGEN, Valencia, Calif.) equilibrated in PBS was added per 45 mL supernatant and rocked overnight at 4° C. Resin was collected by centrifugation and washed three times with 50 mL PBS. gD2 was then eluted from the resin by adding 4×1 mL elution buffer (250 mM imidazole in PBS). Eluted gD2 was filtered through a 0.22-micron filter and dialyzed overnight against PBS. Protein concentration was measured using a Bradford Assay (BioRad, Hercules, Calif.).

Detection of gD2 Purified from *Pichia pastoris*.

NUNC Maxisorp ELISA plates (Thermo Fisher Scientific Inc., Waltham, Mass.) were coated with 0.5 µg purified protein per well overnight at 4° C. Plate was blocked with 2% BSA in PBS for 30 minutes at RT. Primary antibodies, including R45 (rabbit polyclonal, gift from R. Eisenberg and G. Cohen, University of Pennsylvania, Philadelphia), HSV8 (human monoclonal, gift from L. Zeitlin, Mapp BioPharmaceuticals, San Diego, Calif.), DL6 (mouse monoclonal, (Santa Cruz Biotechnology, Dallas, Tex.), and anti-His (mouse monoclonal, Sigma-Aldrich, St. Louis, Mo.), were diluted in PBS-T and added to appropriate wells in duplicate for 1 hour at RT. Wells were washed 5× with 200 µL PBS-Tween 0.2% (PBS-T) per well and appropriate HRP-conjugated secondary antibody (Jackson ImmunoResearch, West Grove, Pa.) was diluted in PBS-T and added to wells for 1 hour at RT. Wells were washed 5× with 200 µL PBS-T per well and developed using ABTS® ELISA HRP Substrate (KPL, Gaithersburg, Md.). The plate was read at 405 nm using a BioTek Synergy HT Plate Reader (Winooski, Vt.).

Llama Immunizations.

The immunization of two llamas, Llama No: 1 and Llama No: 2, was performed by Triple J Farms in Bellingham, Wash. (Protocol #110, approved by Triple J Farms IACUC, USDA registered #91-R-0054). The immunizations occurred on days 0, 21, 42, 63, and 280. Each llama was immunized with 0.5 mg of gD2 per injection, mixed with Complete Freund's Adjuvant for the first injection and incomplete Freund's Adjuvant for subsequent injections. Prior to the first immunization and following each immunization, ~20 mL of serum was collected to monitor for the presence of anti-gD2 antibody. After the fourth and fifth immunizations, 500 mL of blood was taken from each animal and peripheral blood mononuclear cells (PBMCs) were purified using a Ficoll-Paque Plus gradient (GE Healthcare Life Sciences, Piscataway, N.J.). PBMCs were aliquoted and frozen at −80° C. until further use.

Llama Serum ELISA.

NUNC Maxisorp ELISA plates (Thermo Fisher Scientific Inc., Waltham, Mass.) were coated with 100 µl of gD2 at 10 µg/mL and incubated ON at 4° C. The plate was blocked with 2% BSA in PBS for 30 minutes at RT. Freshly thawed serum samples were diluted 1:10,000 in PBS and added in duplicate to wells for 1 hour at RT. Wells were washed 5×200 µl PBS-T per well and HRP-conjugated anti-llama secondary antibody (Bethyl Laboratories, Inc) was diluted 1:10,000 in PBS-T and added to wells for 1 hour at RT. Wells were washed 5× with 200 µl PBS-T per well and developed using ABTS® ELISA HRP Substrate (KPL, Gaithersburg, Md.). The plate was read at 405 nm using a BioTek Synergy HT Plate Reader (Winooski, Vt.).

Llama Serum Neutralization Assay.

Vero cells were plated in Falcon 12-well trays (Thermo Fisher Scientific Inc., Waltham, Mass.) at 4×10$^6$ cells per tray and incubated ON at 37° C. Llama serum samples were heat inactivated at 56° C. for 60 minutes and serial two-fold dilutions were made in DMEM/2% FBS. Approximately 5000 pfu/mL of HSV-2 G was added to each dilution and all dilutions were incubated at 37° C. for 1 hour. Media was removed from the Vero cells and the serum dilutions with virus were added in duplicate to cells for 1 hour at 37° C., with gentle shaking every ten minutes to distribute volume over cells. The inoculum was then removed from cells and cells were overlaid with 2 mL 2% methylcellulose overlay/ 5% FBS in DMEM (Cellgro, Manassas, Va.). Trays were incubated for 3 days at 37° C., stained with crystal violet, and plaques were counted.

Amplification of VHH Regions and Construction of T7 Phage Display Library.

Using PBMCs that were isolated following the fourth (Llama No: 2) or fifth immunization, RNA was extracted using an RNeasy Mini Kit (QIAGEN, Valencia, Calif.) and reverse transcribed into DNA (SuperScript II Reverse Transcriptase, Invitrogen, Carlsbad, Calif.). Nested PCR was performed to amplify the VHH regions from the genomic DNA using primers that bind to the conserved regions flanking the VHH genes. The first round of PCR was performed with primers as previously published, while the second round of primers introduced the appropriate restriction sites for ligation into the phage genome. The VHH band of ~450 base pairs was gel extracted and ligated into pre-digested T7 phage vector arms as described in the manufacturer's handbook (Novagen Inc., Madison, Wis.). The ligation reaction was packaged into the phage according to the manufacturer's protocol and titered to determine the diversity of the packaged library prior to amplification. After amplification, the library was aliquoted and stored at −80° C. until further use. VHH expressed on the phage surface are referred to as VHH-phage.

Biopanning of VHH/T7 Library Against gD2.

For the first round of biopanning, 10$^9$ pfu from the phage library was added to a well coated with 0.5 µg gD2 and incubated at room temperature for 1 hour. Wells were then washed 10 times with shaking for 1 minute with tris-buffered saline (TBS) with 0.05% Tween (TBS-T) and 10 times with TBS. Bound phage were eluted using 200 µl of 1% SDS in TBS incubated on wells for 1 hour at room temperature. A sample of the eluted phage was used to titer the amount of phage present, and the remaining eluted phage were added to 50 mL of BLT5403 grown in LB/Amp at $OD_{600}$ 0.5 and shaken at 37° C. until lysis occurred. This phage lysate was titered and used as the input for the next round of biopanning, which was carried out using the same procedure. Additional rounds of biopanning were performed against gD2 and individual plaques from the phage elution after the second (Llama No: 1) or sixth (Llama No: 2) round of biopanning were picked, amplified, and sequenced.

Antibody Capture Biopanning.

Antibody capture biopanning was performed based on a previously published protocol (*Proc Natl Acad Sci USA* 92, 6439-6443 (1995)). It was carried out as described above, except that the ELISA wells were first coated with the non-neutralizing gD2 capture antibody, DL6 (Santa Cruz Biotechnology, Dallas, Tex.). After this coating step, gD2 was added and then the biopanning protocol proceeded as described in the previous section.

VHH-Phage ELISA.

An ELISA was performed to determine if individual VHH-phage clones could bind to gD2. NUNC Maxisorp ELISA plates (Thermo Fisher Scientific Inc., Waltham, Mass.) were coated with 0.5 µg gD2 per well and incubated ON at 4° C. The plate was blocked for 1 hour with 2% BSA in PBS, and then 10$^9$ pfu of each phage clone was added in duplicate and incubated at RT for 1 hour. After removing phage, the plate was washed 5×200 µL PBS-T per well.

Anti-T7 tail fiber monoclonal antibody (GE Healthcare Life Sciences, Piscataway, N.J.) was diluted to 1:1000 and added to each well for 1 hour at RT. After washing the plate 5×200 μL PBS-T per well, HRP-conjugated anti-mouse IgG secondary antibody (Jackson ImmunoResearch, West Grove, Pa.) was added at 1:3000 and incubated at RT for 1 hour. After a final wash of 5×200 μL PBS-T per well, 200 μL of ABTS® ELISA HRP Substrate (KPL, Gaithersburg, Md.) was added. The plate was read at 405 nm using a BioTek Synergy HT Plate Reader (Winooski, Vt.).

Cloning and Expression of VHH in *E. coli*.

VHH sequences were amplified from phage by PCR amplification using the primers that introduced EcoRI and XhoI restriction sites for cloning in to pET-47b (Novagen Inc., Madison, Wis.). Additional primer sets were used to amplify VHH and insert a second VHH sequence with a GS linker between them to make a bivalent VHH construct. The monovalent and bivalent VHH constructs were transformed in to BL21 DE3 competent cells (New England Biolabs, Ipswich, Mass.). Two methods of expression and purification were utilized depending on the solubility of the VHH protein.

1) Osmotic shock:

For the VHH that were soluble (all VHH derived from Llama No: 2, indicated by R##), an osmotic shock protocol was utilized to purify protein from the periplasmic space, as described by Graef et al. (BMC Biotechnol 11, 86 (2011)). Briefly, an ON 30 mL mid-scale culture was diluted in 450 mL Terrific Broth and grown at 25° C. for 3 hours. Cells were induced at 1 mM IPTG (Lab Scientific, Inc, Highlands, N.J.) and grown for an additional 3 hours at 25° C. After centrifugation, the cell pellet was lysed in Tris-sucrose buffer with lysozyme. Contents of periplasmic space were separated from cellular debris by centrifugation and Ni-NTA Agarose (QIAGEN, Valencia, Calif.) was added to the supernatant ON with rocking at 4° C. Agarose was collected by centrifugation and washed, and protein was eluted by addition of 3 mL elution buffer.

2) Insoluble Protein Purification:

For those VHH that were insoluble (all VHH derived from Llama No: 1, indicated by P##), an ON 10 mL culture was diluted into 750 mL of LB/Kan and grown until $OD_{600}$ 0.6-0.8. After induction with IPTG at 1 mM for 3 hours at 37° C., cells were harvested by centrifugation at 3500 g for 30 minutes, resuspended in 10 mL lysis buffer (6 M Guanidine hydochloride, 0.1 M $NaH_2PO_4$, 0.01 M Tris base, 0.01 M imidazole, pH 8) and frozen at −80° C. for at least 30 minutes. Upon thawing, the volume of the lysate was brought to 30 mL with lysis buffer, incubated with rocking at RT for at least 30 minutes, and then centrifuged at 14000 rpm for 30 minutes. After the pellet was discarded, Ni-NTA Agarose (QIAGEN, Valencia, Calif.) was added to lysate and rocked at RT for 1 hour or ON at 4° C. Beads were washed twice with 7 mL Wash Buffer 1 (8 M urea, 0.1 M $NaH_2PO_4$, 0.15 M NaCl, 0.02 M imidazole, pH 8) and then washed with ~50 mL (7×7 mL) Wash Buffer 2 (0.05 M $NaH_2PO_4$, 0.5 M NaCl, 0.02 M imidazole, pH 8). To elute VHH from beads, 4×1 mL Elution Buffer (0.05 M $NaH_2PO_4$, 0.5 M NaCl, 0.25 M imidazole, pH 8) was added for 1 hour at RT.

For both protein purification methods, eluted VHH were dialyzed against PBS with 1 mM DTT with at least 4 buffer changes. VHH were concentrated with Amicon Ultra-15 Centrifugal Filter Unit (EMD Millipore, Billerica, Mass.), centrifuged at 16,000×g for 10 minutes to remove precipitated protein, and protein concentration was measured by Bradford assay (BioRad, Hercules, Calif.).

Cloning and Expression of Pentavalent VHH.

To create a pentavalent VHH, the pVT2 plasmid was obtained from C. Roger Mackenzie (National Research Council Canada, Ottawa, Ontario, Canada). This plasmid allows for cloning of VHH as a N-terminal fusion protein with the verotoxin B subunit, resulting in self-assembly in to a pentamer (*J Immunol Methods* 318, 88-94 (2007)). R33 expressed as a pentamer will be referred to as NR33. The pentavalent R33/pVT2 construct was transformed into competent BL21 DE3 cells (New England Biolabs, Ipswich, Mass.) and expressed and purified as previously described (*J Mol Biol* 335, 49-56 (2004)). Purified NR33 was run through a Superdex200 column to verify self-assembly.

Coomassie and Western Blot of Purified gD2 and VHH.

To verify the size of purified protein, approximately 800 ng of gD2 or each VHH sample was run on a SDS-PAGE gel for Commassie staining and approximately 200 ng of each sample was run for a Western blot. For Western blotting, samples were transferred to polyvinyl difluoride (PVDF) membrane by a semi-dry transfer system (Biorad Trans-Blot SD Semi-Dry Transfer Cell, Hercules, Calif.) and detection was performed using standard techniques. Briefly, PVDF membrane with transferred protein was blocked with 5% milk for 1 hour at RT or ON at 4° C. Primary antibody was diluted in PBS-T and incubated on blot for 1 hour at RT with rocking. Blot was washed 4×10 minutes with PBS-T, and alkaline-phosphatase-conjugated secondary antibody (Jackson ImmunoResearch Inc., West Grove, Pa.) was diluted in PBS-T and added to blot. After a final wash of 4×10 minutes in PBS-T, NBT (nitro-blue tetrazolium chloride) and BCIP (5-bromo-4-chloro-3'-indolyphosphate p-toluidine salt) detection reagents were added until bands were visualized.

ELISA to Validate VHH Binding to gD2.

An ELISA was performed to determine if purified VHH bind to gD2. Wells of NUNC Maxisorp ELISA plates (Thermo Fisher Scientific Inc., Waltham, Mass.) were coated with various dilutions of VHH made in PBS and incubated ON at 4° C. Purified gD2 diluted in PBS-T was added to wells for 1 hour at RT. Wells were washed 4×200 μL PBS-T and the anti-gD antibody DL6 (Santa Cruz Biotechnology, Dallas, Tex.) diluted in PBS-T was added to detect gD2 binding by VHH. After a 1 hour incubation at RT, wells were washed again 5×200 μL PBS-T and an anti-mouse secondary antibody conjugated to HRP (Jackson ImmunoResearch, West Grove, Pa.) was added. After a final wash with PBS-T 4×200 nL, 200 μL ABTS® ELISA HRP Substrate (KPL, Gaithersburg, Md.) was added. The plate was read at 405 nm using a BioTek Synergy HT Plate Reader (Winooski, Vt.).

Flow Cytometry to Validate VHH Binding to Surface Expressed-gD2.

Z4/6 cells (gift from D. Johnson, Oregon Health and Science University) are a derivative of L cells that stably express gD2 at the cell surface. Nearly confluent cells were trypsinized, washed once with PBS, and resuspended at $0.5 \times 10^6$ cells/mL. 500 μL of cells were aliquoted, centrifuged at 500 g for 5 minutes, and resuspended with 1 mL 1% BSA/PBS and incubated at 37° C. for 30 minutes for blocking. Samples were centrifuged at 500 g for 5 minutes, resuspended in VHH or DL6 antibody (Santa Cruz Biotechnology, Dallas, Tex.) diluted in 1% BSA/PBS, and incubated for 1 hour at 4° C. Cells were washed twice with 2 mL PBS and resuspended in appropriate FITC-conjugated secondary antibody (Jackson ImmunoResearch, West Grove, Pa.) diluted in 1% BSA/PBS for 30 minutes at 4° C., followed by a final wash with 2 mL PBS. Samples were run on a Becton-Dickinson FACSCalibur Cytometer and data was analyzed using FloJo (Tree Star Inc., Ashland, Oreg.).

VHH sequences were amplified using primers to introduce the appropriate restriction sites for cloning into the pLEX plasmid, as well as to introduce an N-terminal His tag and C-terminal myc tag.

HSV-2 Neutralization Assay with VHH

Vero cells were plated in Falcon 12-well trays (Thermo Fisher Scientific Inc., Waltham, Mass.) at $4 \times 10^6$ cells per tray and incubated overnight at 37° C. VHH samples (monovalent, bivalent, and pentavalent) were serially diluted in DMEM/2% FBS with HSV-2 G (ATCC, Manassas, Va.) at $5 \times 10^3$ pfu/mL and all dilutions were incubated at 37° C. for 1 hour. Media was removed from the Vero cells and 100 µL of VHH dilutions with virus were added in duplicate to cells for 1 hour at 37° C., with gentle shaking every ten minutes to distribute volume over cells. Cells were overlaid with 2 mL of 2% methylcellulose overlay/5% FBS in DMEM (Cellgro, Manassas, Va.). Trays were incubated for 3 days at 37° C., stained with crystal violet, and plaques were counted.

Testing VHH Vaginal HSV-2 Animal Challenge Model.

Six to eight week old female CF-1 were purchased from Harlan (Indianapolis, Ind.) and housed under reversed photoperiod conditions. As reported previously (BMC Infect Dis 6, 1471-2334 (2006)), mice are injected subcutaneously in the hindquarters with 2.5 mg of Depo Provera (UpJohn Co. 400 mg/mL) seven days before the planned viral challenge. On day seven, the VHH candidate and the viral inoculum of 10 $ID_{50}$ are mixed in a total volume of 20 µL and promptly delivered to the vagina with a fire-polished Wiretrol pipet (Drummond Co., Broomall, Pa.). Three days later (Day 10) the vagina is lavaged using 20 µL of Bartel's Tissue Culture Refeeding Media; the fluid is delivered vaginally and withdrawn 10 to 20 times to collect HSV shed into the vagina. The lavage fluid is centrifuged at 6500 rpm for 5 minutes to remove mucus and cells, and then placed on human newborn foreskin cells to assay for presence of virus. Cells are observed by microscope 48 hours later and scored yes/no for infection. Mice used in these studies were maintained in accordance with the National Institutes of Health guidelines for the humane use of laboratory animals. All experimental procedures involving mice were approved by the Institutional Animal Care and Use Committee of the Johns Hopkins University (Protocol Number MO12H147).

Expression, Purification, Refolding of VHHExoA.

A VHH that binds to gD2 of HSV-2 (called R33) was identified through the methods described above. P10, a VHH that does not bind to gD2 was also identified. VHH sequences were amplified using primers that introduced EcoRI and XhoI restriction sites for cloning in to pET-47b (Novagen Inc., Madison, Wis.). The previously published exotoxin A sequence (*Proc Natl Acad Sci USA* 109, 11782-11787 (2012)) was synthesized (GenScript, Inc, Piscataway, N.J.) and cloned in frame to the C-terminus of the VHH (R33 and P10) already present in the pET-47b vector (SEQ ID NO:). Expression, purification, and refolding of VHHExoA proteins were performed based on a previously published protocol (*Anal Biochem* 205, 263-270 (1992)). Briefly, large-scale cultures (800 mL) of transformed BL21 DE3 cells (New England Biolabs, Ipswich, Mass.) were grown to $OD_{600}$ 0.6 and induced at 1 mM with IPTG (Lab Scientific, Inc, Highlands, N.J.) for 3 hours at 37° C. After cells were harvested and lysed under denaturing conditions (6 M GuHCl), Ni-NTA Agarose (QIAGEN, Valencia, Calif.) was added to the clarified lysate to purify the His-tagged VHHExoA protein. After washing, VHHExoA protein was eluted (8 M urea, 250 mM imidazole, 50 mM $NaH_2PO_4$, 500 mM NaCl, 300 mM DTT) diluted 1:100 in refolding buffer (100 mM Tris, 500 mM L-arginine, 8 mM oxidized glutathione, 2 mM EDTA), and incubated at 10° C. overnight. After completion of the refolding reaction, the refolded VHHExoA was concentrated with an Amicon Ultra-15 Centrifugal Filter Unit (EMD Millipore, Billerica, Mass.) and buffer exchange was performed by repeatedly bringing up the volume of the concentrated protein with PBS. The final volume of the protein was brought to ~1 mL, aliquoted, and frozen at −80° C. until use. Protein concentration was determined using a Bradford assay (BioRad, Hercules, Calif.).

Toxicity Assay (MTS Assay). The CellTiter 96® AQueous One Solution Cell Proliferation Assay was used to determine toxicity of VHHExoA on cell lines, and the assay was carried out using the protocol recommended by the manufacturer (Promega, Madison, Wis.). Z4/6 cells, expressing gD2 at the cell surface, and the parental L cell line were plated in 96-well trays at $3 \times 10^5$ cells/well overnight. The following day, dilutions of the VHHExoA proteins were added to wells and incubated overnight. About 16 hours after the addition of protein, 20 µL of the CellTiter 96® AQueous One Solution reagent was added to each well and incubated 4 hours at 37° C. Higher OD values indicate greater cell viability, and therefore, less toxicity. The plate was read at 490 nm with a BioTek Synergy HT Plate Reader (Winooski, Vt.).

ELISA: Binding of VHHExoA to gD2. An ELISA was performed to determine if the purified VHHExoA was capable of binding to gD2. NUNC ELISA plates were coated with dilutions of VHHExoA (0.25 µg/well), and after a blocking step, dilutions of purified gD2 were added to wells in duplicate. After a washing step of 5×200 µL PBS-0.05% Tween (PBS-T) wash buffer, the anti-gD antibody DL6 (Santa Cruz Biotechnology, Dallas, Tex.) was added at 1:1000 for 1 hour. Wells were washed again and HRP-conjugated anti-mouse (Sigma-Aldrich, St. Louis, Mo.) was added at 1:3000 for 1 hour. A final wash step was performed, and plate was developed by adding 100 µl/well ABTS® ELISA HRP Substrate (KPL, Gaithersburg, Md.). The plate was read at 405 nm using a BioTek Synergy HT Plate Reader (Winooski, Vt.).

In Vitro Infectious Center Assay (ICA)

Vero cells were plated in 12-well trays at $4 \times 10^6$ cells/tray and after 24 hours were infected with HSV-2 G (ATCC, Manassas, Va.) at 500 pfu/well. Following the 1 hour adsorption time, dilutions of the VHHExoA proteins were added to wells in duplicate and complete media (DMEM, CellGro, Manassas, Va.) was added to bring volume up to 700 µL per well. About 16 hours later, supernatant was removed and cells were trypsinized briefly with 250 µL trypsin/EDTA (CellGro, Manassas, Va.) before adding an equal volume of complete media. Cells were centrifuged at 500 g for 5 minutes to pellet cells, and then resuspended in 200 µL of complete media. Dilutions of the infected Vero cells were made in uninfected Vero cells harvested the same day, and plated in 12-well trays so that total cell number was roughly $3 \times 10^5$ cells/well. Cells were overlaid with 0.5% methylcellulose/5% FBS to bring volume to 1 ml. After 2 days, cells were stained with crystal violet and plaques were counted.

Animal Experiments. Six to eight week old female CF-1 were purchased from Harlan (Indianapolis, Ind.) and housed under reversed photoperiod conditions. On Day 0 mice are injected subcutaneously in the highquarters with 2.5 mg of Depo Provera (UpJohn Co. 400 mg/ml) one week before the planned viral challenge. On Day 7, 10 μL of the virus inoculum (10 ID$_{50}$) is combined with 10 μL of the VHHExoA (20 μM, therefore final concentration is 10 μM) and 20 μL is promptly delivered to the vagina with a fire-polished Wiretrol pipet (Drummond Co., Broomall, Pa.). Six, 24, and 48 hours post challenge and, mice are vaginally treated with a 10 μL of 20 μM dose of VHHExoA. On Day 10 the vagina is lavaged using 20 μl of Bartel's Tissue Culture Refeeding Media; the fluid is delivered vaginally and withdrawn 10 to 20 times to collect HSV shed into the vagina. The lavage fluid is centrifuged at 6500 rpm for 5 minutes to remove mucus and cells, and then placed on human newborn foreskin cells to assay for presence of virus. Cells are observed by microscope 48 hours later (Day 13) and scored yes/no for infection. All experimental procedures involving mice were approved by the Institutional Animal Care and Use Committee of the Johns Hopkins University (Protocol Number MO12H147).

Statistical Analysis. For the viral neutralization assays, the significance of the difference in plaque numbers was calculated using an ANOVA test, with a Bonferroni correction (STATA Corp, College Station, Tex.). For analysis of the results from animal HSV-2 challenge experiments, a Fisher exact test (two-tailed) was used to compare the number of animals infected between experimental and the control groups.

Example 1

Expression and Purification of Recombinant gD2 in *Pichia pastoris*

Figure 2A:
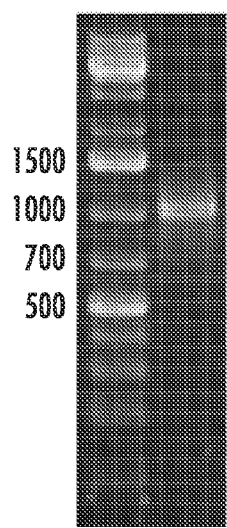
FIG. 2 depicts purification of gD2 From *Pichia pastoris*. A) Amino acids 1-314 of gD2 were amplified by PCR from the HSV-2 strain 186 genome. B and C) Purified gD2 from *Pichia pastoris* was separated by SDS-PAGE and stained with Coomassie (B) or transferred to PVDF membrane and detected with a polyclonal anti-gD2 antibody (R45) by Western blotting (C).
Figure 2B:
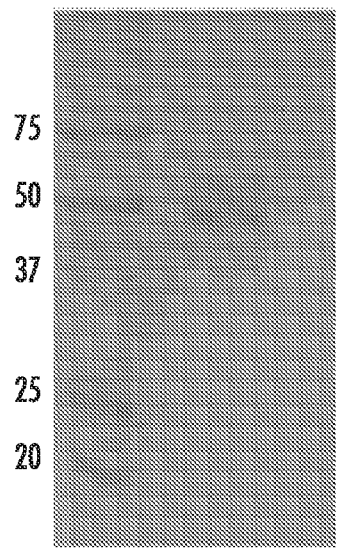
Figure 2C:
Figure 3:
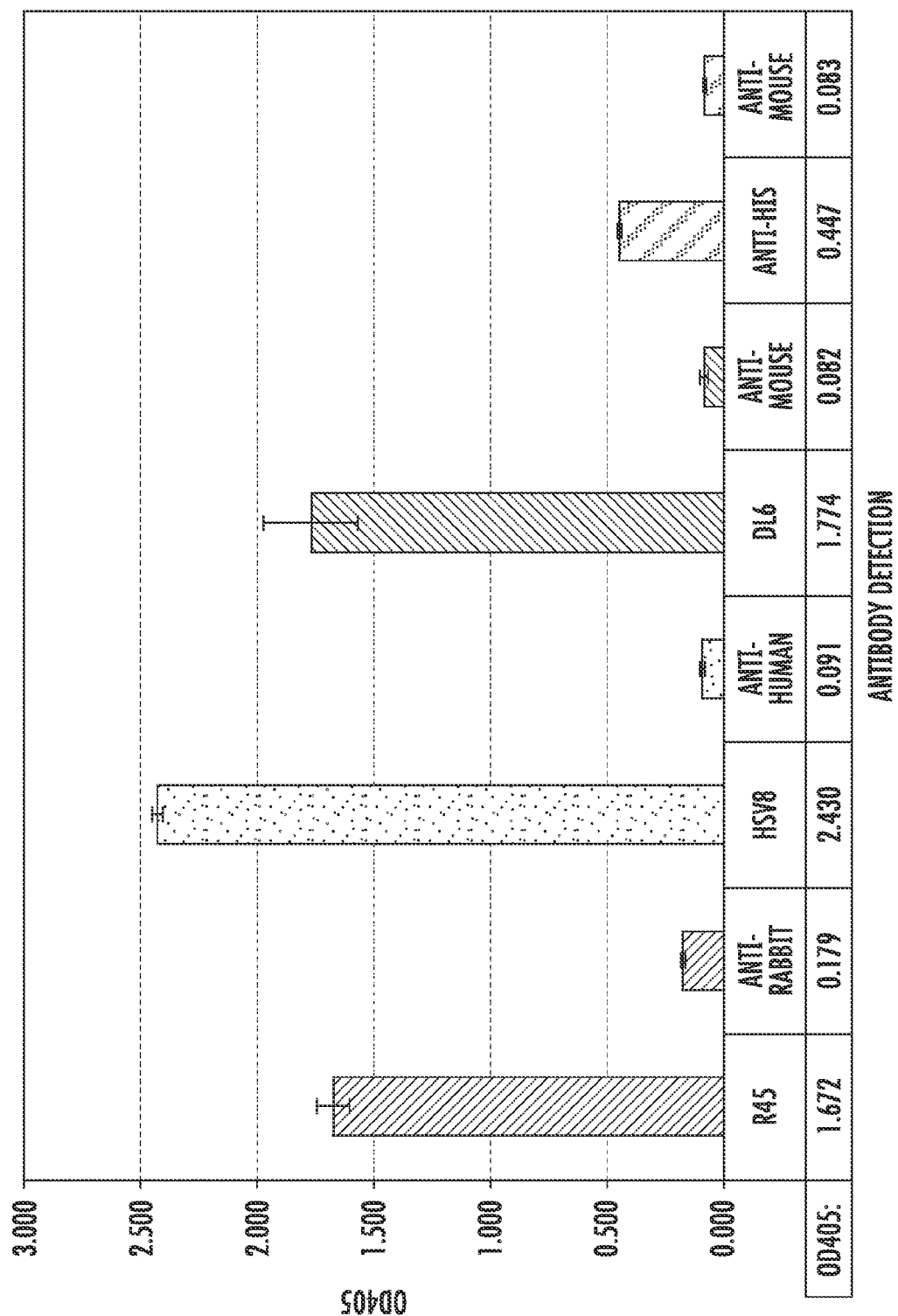
FIG. 3 shows antibody reactivity to purified gD2 (ELISA). ELISA wells were coated with gD2 and detected with a panel of anti-gD2 antibodies: R45 (rabbit, polyclonal), HSV8 (human, monoclonal), DL6 (mouse, monoclonal), anti-His (mouse, monoclonal). Additionally wells coated with gD2 where only HRP-conjugated secondary antibody (anti-rabbit, anti-human, and anti-mouse) was added were run as controls.
Figure 4:
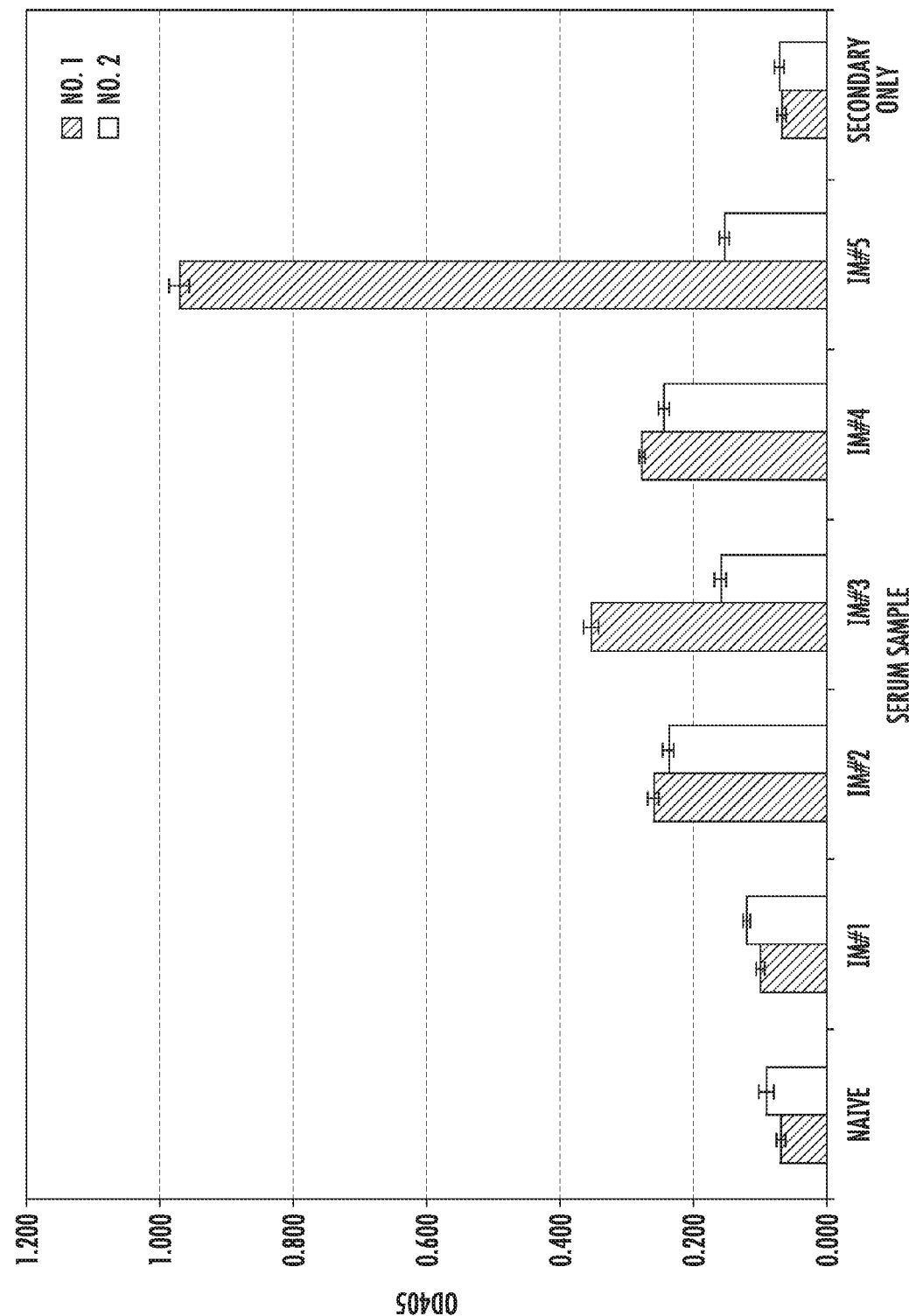
FIG. 4 depicts llama serum ELISA. Llama serum collected before the initiation of immunization (naïve) and after each immunization (Im#1-5) was diluted 1:10,000 and used to coat ELISA wells. gD2 was added and binding was detected to determine if the llamas mounted an immune response against the gD2 immunizations.
Figure 5:
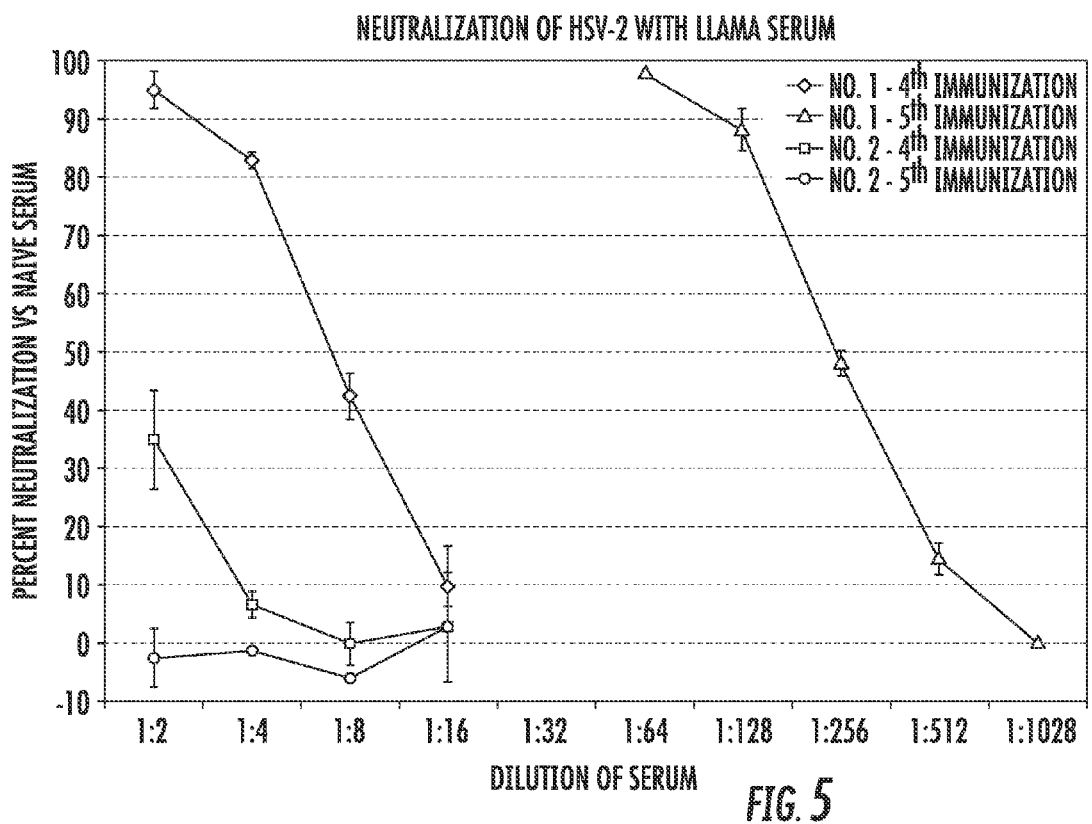
FIG. 5 shows a llama serum neutralization assay. Naïve llama serum and llama serum following the 4$^{th}$ and 5$^{th}$ immunizations was serially diluted and incubated with HSV-2 for 1 hour at 37° C. before adsorption on Vero cells for 1 hour. After overlay with methylcellulose and incubation for 2 days, cells were stained and plaques counted. Each dilution was assayed in duplicate and error bars represent maximum and minimum percent values. Results were expressed as percent neutralization compared to naïve serum.
Figure 6:
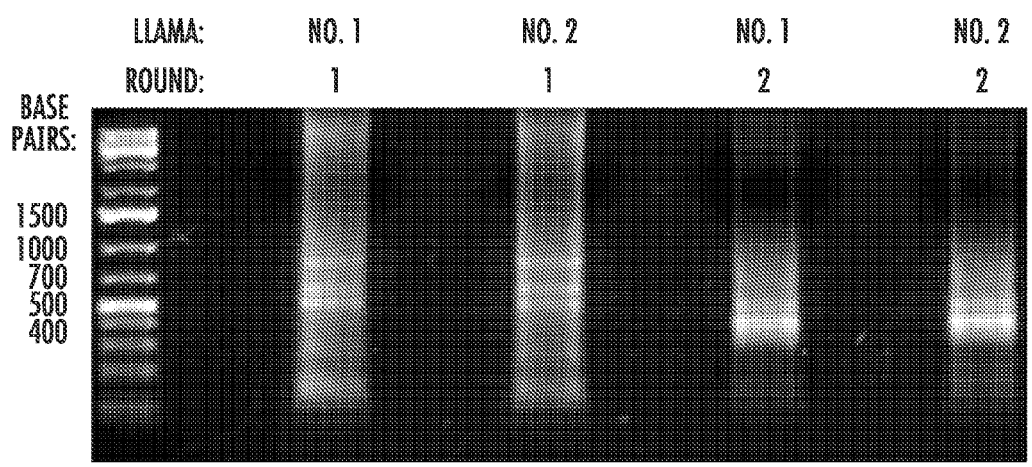
Figure 7:
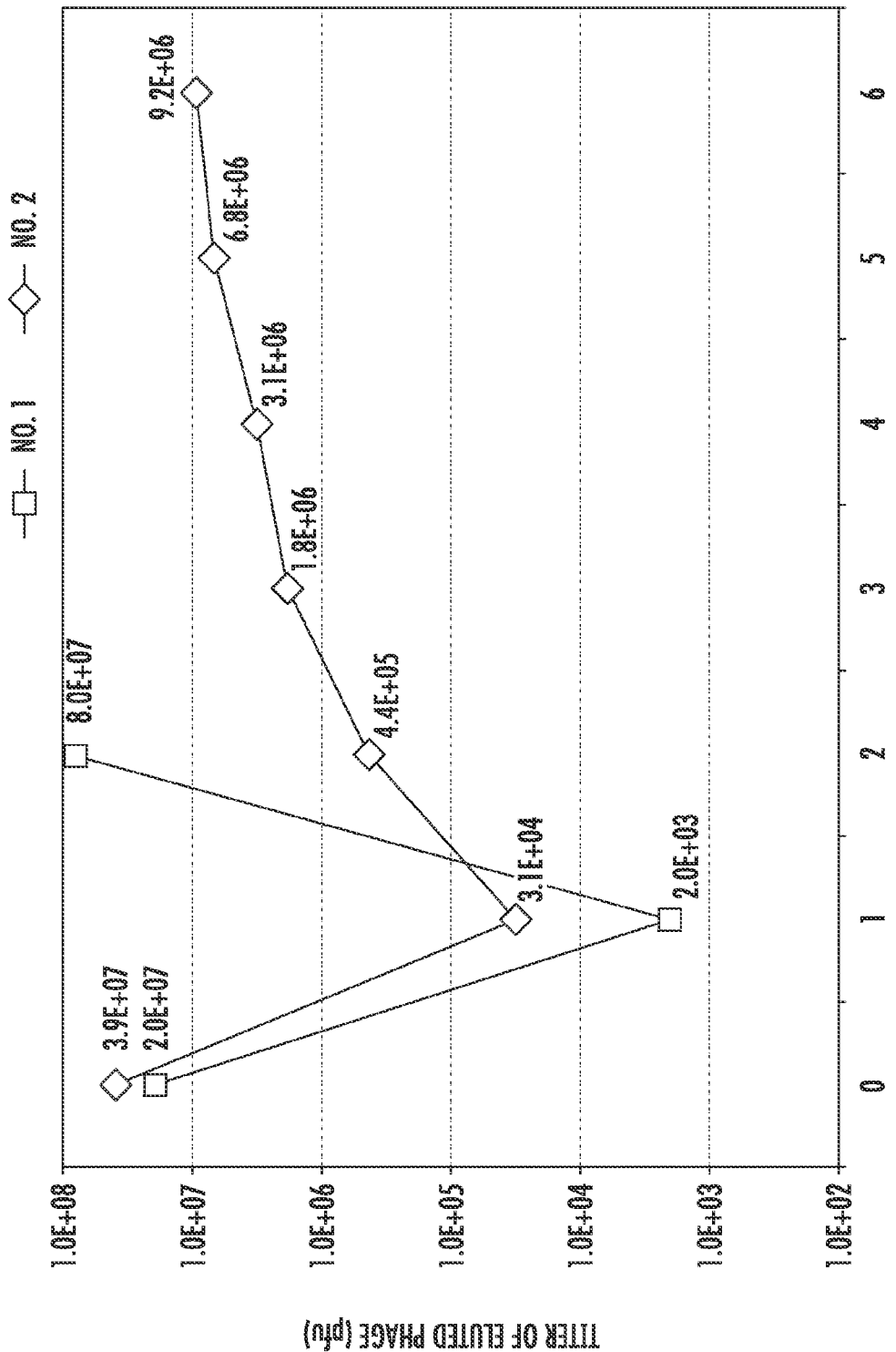
FIG. 7 shows biopanning of VHH-Phage Library on gD2. After each round of biopanning, the eluted phage were titered to monitor the concentration of phage during the biopanning process. The large drop in phage titer after the first round of biopanning was expected, as most of the VHH-phage in the library are not specific for gD2. Subsequent rounds of biopanning show increased phage concentration as enrichment for gD2 specific VHH-phage occurs.
Figure 8:
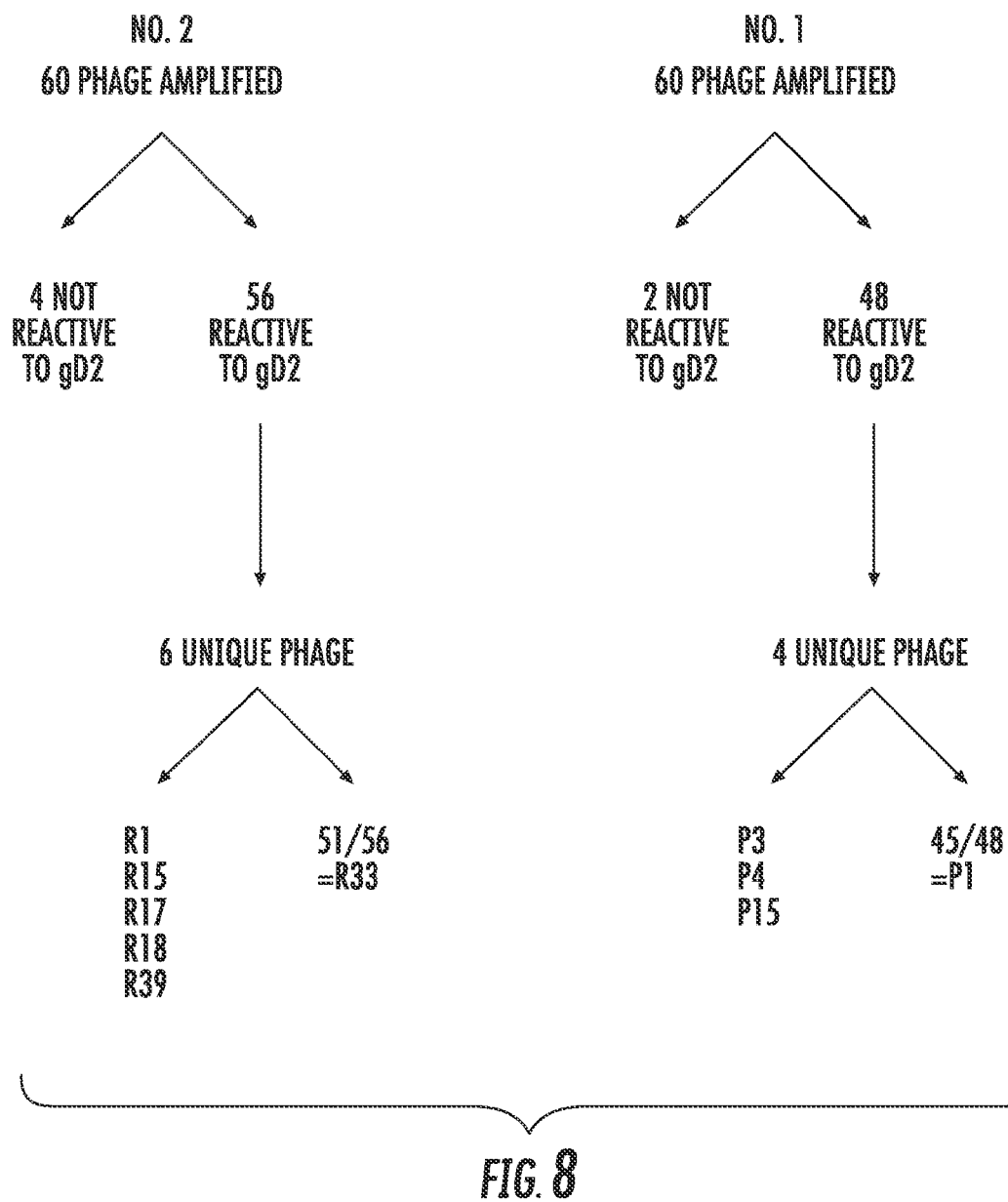
FIG. 8 is a flowchart diagramming the process of identifying unique VHH sequences that bind to gD2. Individual phage clones were amplified and tested by ELISA to determine if they are reactive to gD2. Those that were reactive were sequenced, and the sequences were compared to determine the number of unique VHH sequences.
Figure 10A:
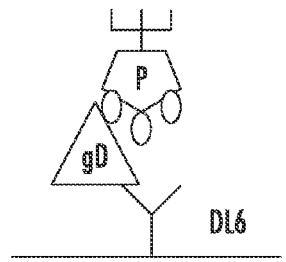
FIG. 10 illustrates antibody capture biopanning. A) Conceptual diagram of how capture biopanning immobilizes gD2 through binding to a particular epitope, thereby promoting selection of sVHH-phage that bind to other sites of gD2. B) The eluted phage after each round of biopanning were titered to monitor the concentration of phage during the biopanning process.
Figure 10B:
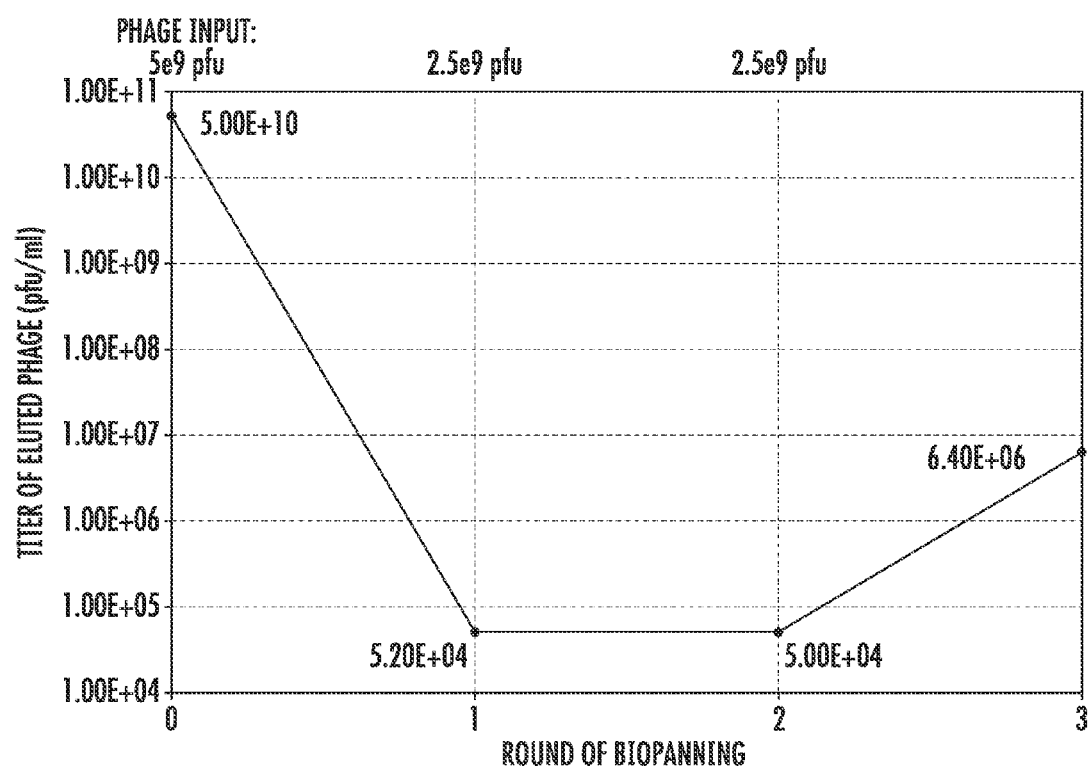
Figure 11:
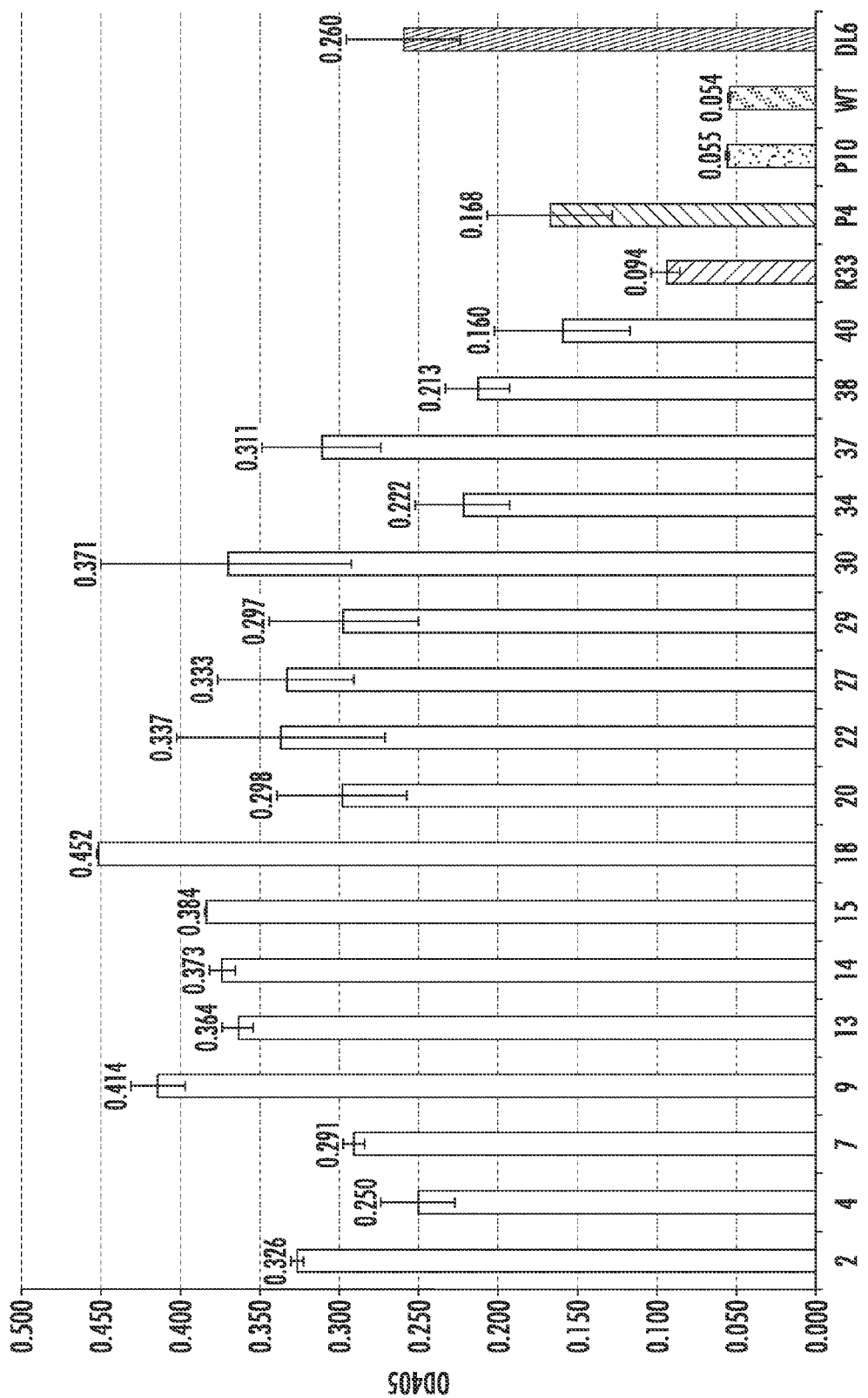
FIG. 11 shows the results of antibody capture biopanning VHH-Phage ELISA. VHH-phage clones after three rounds of capture biopanning were individually amplified and tested for reactivity to gD2 by ELISA. Wells were coated with gD2 and VHH-phage clones were added and then detected with an anti-phage antibody. Previously identified VHH-phage were used as positive (R33 and P4) and negative (P10) controls. The anti-gD2 antibody DL6 was also used as a positive control. Each VHH-phage was assayed in duplicate and error bars represent maximum and minimum values.

The extracellular domain of gD2 was amplified from the HSV-2 186 genome (FIG. 2A) and cloned in to the *Pichia pastoris* expression vector pPIC9 for expression and purification (*Protein Expression and Purification* 25, 400-408 (2002)). The size and purity of the purified gD2 was verified by separation with SDS-PAGE and staining with Coomassie (FIG. 2B), as well as by Western blot using a polyclonal anti-gD antibody (FIG. 2C). A band approximately 48 kDa was detected with both methods, somewhat smeared due to the variable glycosylation pattern from *P. pastoris*, as has been reported previously. gD2 was successfully detected by ELISA using a panel of conformation and non-conformational anti-gD2 antibodies (FIG. 3), indicating that gD2 was successfully purified and suggests that it is folded correctly.

Example 2

Monitoring Antibody Response of gD2 Immunized Llamas

Two llamas, Llama No: 1 and Llama No: 2, were immunized five times with gD2, and after each immunization the animals were bled to obtain serum samples. The induction of anti-gD2 antibodies was determined using an ELISA. As shown in FIG. 4, serum from both llamas demonstrated reactivity to gD2 following the second immunization compared to serum collected prior to immunization and after the first immunization. The highest reactivity to gD2 in serum collected from Llama No: 2 occurred after the fourth immunization. Serum from Llama No: 1 had similar reactivity to gD2 as Llama No: 2, except there was a dramatic increase in gD2-reactivity following the last immunization (FIG. 4). In addition to the ability to bind gD2, the serum was also tested for the ability to neutralize HSV-2. While serum from Llama No: 2 had no significant neutralizing capability, Llama No: 1's serum obtained after the fourth and fifth immunizations generated $IC_{50}$ values of approximately 1:8 and 1:256, respectively (FIG. 5). Taken together, these results indicate while both llamas did mount an antibody response against the gD2 immunogen as measured by ELISA, only Llama No: 1 developed a neutralizing antibody response. This neutralizing response, however, does not guarantee that neutralizing VHH were induced, just that a neutralizing antibody response was generated.

Example 3

Construction of VHH/T7 Phage Display Library and Biopanning Against gD2

Based on the ELISA reactivity and neutralizing capability of the serum, VHH genes were amplified from cDNA generated from the PBMCs isolated after Llama No: 2's fourth immunization and Llama No: 1's fifth immunization (FIG. 6). The amplified VHH genes were ligated into T7 phage vector to generate libraries with initial diversities of $3.9\times10^7$ pfu for Llama No: 2 and $1.98\times10^7$ pfu for Llama No: 1. For Llama No: 2, after the first round of biopanning, the titer of eluted phage increased stepwise following each round of biopanning, indicating a gradual enrichment for VHH-phage binding to gD2 (FIG. 7). Titers of eluted phage from Llama No: 1's library, however, reached saturation after only two rounds of biopanning (FIG. 7), a pattern that was consistent despite repeated attempts with different conditions (data not shown). This meant that Llama No: 1's library was already dominated by a population of phage reactive to gD2, and that further rounds of biopanning would not select for additional unique VHH sequences.

Example 4

VHH-Phage Binding to gD2

Individual plaques from the phage elution after the second round of biopanning for Llama No: 1 and the sixth round of biopanning for Llama No: 2 were picked and amplified for analysis. Sixty VHH-phage clones were amplified from each llama and tested in an ELISA to determine if they can bind to gD2. For Llama No: 2, of the 60 VHH-phage tested, 56 reacted to gD2 by ELISA (data not shown). After sequencing it was determined that 91% of these sequences were identical (R33), and that overall there were 6 unique VHH sequences (FIG. 8). For Llama No: 1, of the 60 VHH-phage tested, there were 48 VHH-phage that reacted to gD2 by ELISA (data not shown). Sequencing revealed that 94% of the VHH sequences were identical (P1), and that overall there were 4 unique VHH sequences (FIG. 8). A VHH-phage clone, called P10, that was amplified from Llama No: 1's library prior to any biopanning was also tested and sequenced for use as a negative control VHH-phage that did not bind to gD2. A standardized VHH-phage ELISA with $10^9$ pfu per well was performed to determine relative reactivity to gD2 among the unique VHH isolated. All four of Llama No: 1's unique VHH-phage had higher reactivity to gD2 than any of Llama No: 2's VHH-phage, although all of them were higher than the negative control VHH-phage, P10 (FIG. 9).

Example 5

Antibody Capture Biopanning

Based on the antibody capture biopanning method described by Sanna et al., ELISA wells were coated with the non-neutralizing antibody DL6 in order to capture gD2 by binding to one of its non-neutralizing epitopes (FIG. 10A). After the first round of biopanning (Llama No: 1's library only), the titer of eluted phage increased over the next two rounds of biopanning (FIG. 10B), and plaques were picked after the third round to monitor the VHH sequences. 40 VHH-phage plaques were picked and tested for reactivity to gD2 by ELISA. Seventeen of these phage were able to bind gD2, and each of these phage were titered to perform a standardized phage ELISA with $10^9$ pfu/well. As shown in FIG. 11, their reactivity to gD2 was variable, but appeared to be higher than both R33/phage and P4/phage, which were run as positive controls. When the VHH genes were sequenced, however, all VHH sequences were identical to one of the 4 previously identified phage from Llama No: 1.

Example 6

VHH Sequence Analysis

An alignment of all 10 unique sequences that bind to gD2, plus P10, reveals that they are indeed VHH sequences and that the hallmark VHH residues are present (FIG. 12). Comparing the sequences from each individual llama however, reveals limited variation in the sequences. For example, there are only 11 amino acid differences among the six unique VHH sequences for Llama No: 2, and only five of those amino acid differences occur in variable regions of the VHH that determine antigen specificity (called CDR). Many of the amino acid differences are conserved within the same class of amino acids and therefore unlikely to affect antigen binding. As a result, after determining that Llama No: 2's VHH bind to gD2 at similar levels by ELISA (FIG. 14), we decided to focus on R33, the majority sequence selected from biopanning.

Figure 9:
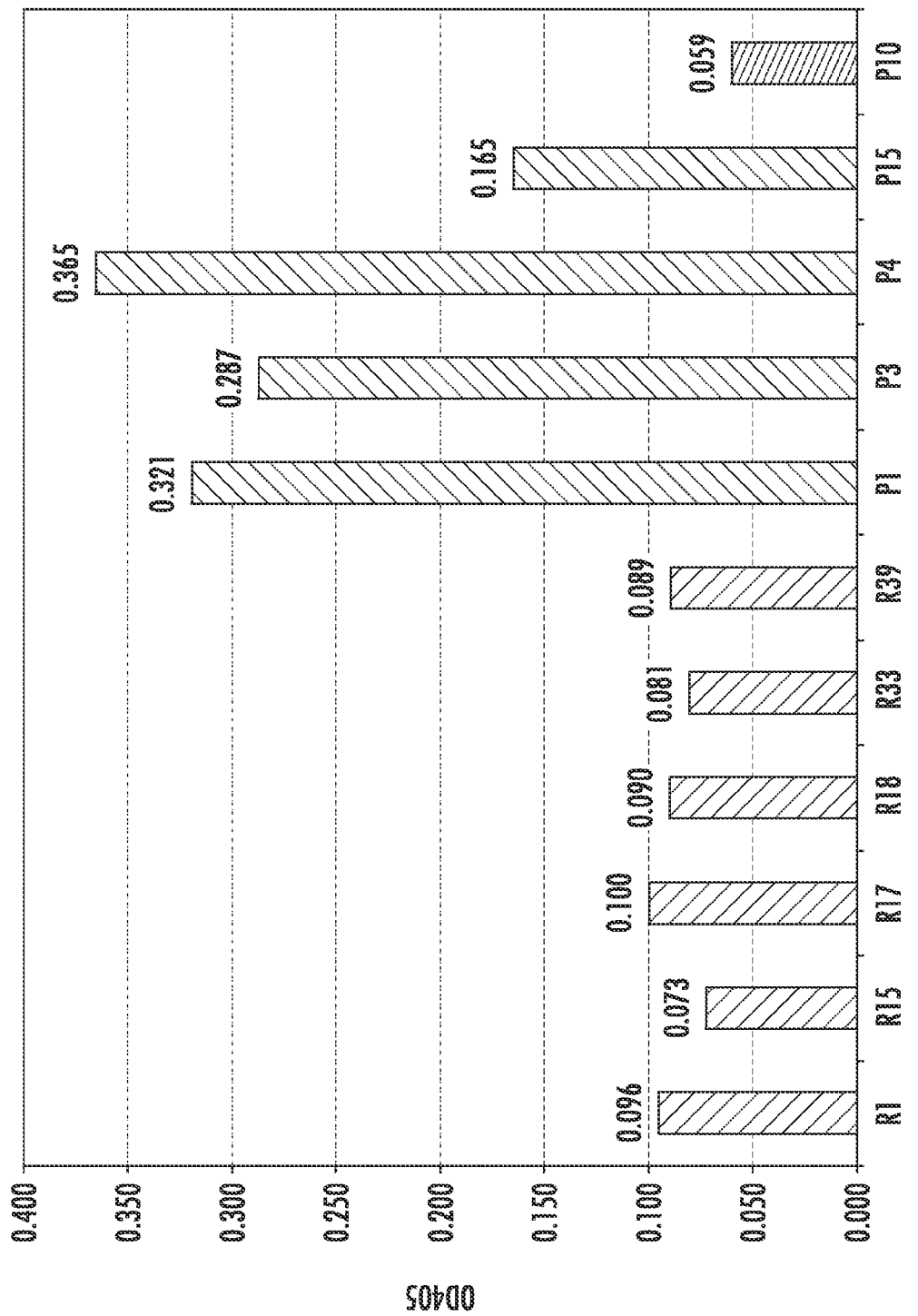
FIG. 9 shows VHH-Phage Binding to gD2. VHH-phage clones after multiple rounds of biopanning were individually amplified and tested for reactivity to gD2 by ELISA. Wells were coated with gD2, VHH-phage clones were added and then detected with an anti-phage antibody. The six unique VHH from Llama No: 2 (R1, R15, R17, R18, R33, and R39), four unique VHH from Llama No: 1 (P1, P3, P4, and P15), and one non-gD2 binding VHH-phage (P10) were tested.

Similarly, Llama No: 1's VHHs exhibit only five amino acid differences, several of which are conserved within the same class of amino acids. Based on the VHH-phage ELISA, we decided to proceed with P4, the VHH with the highest reactivity to gD2 in the VHH-phage ELISA (FIG. 9). Llama No: 1's sequences, while certainly VHH sequences, are missing several canonical amino acid residues (F37, E44, R45, G47), particularly in the very important framework 2 region (FR2). The FR2 region is critical for VHH folding and solubility because this is the region where the light chain would normally be interacting with the heavy chain, and is typically a very hydrophobic region in full-length antibodies. Camelid VHH antibodies, however, have evolved to accumulate amino acid changes that make the region more hydrophilic, allowing for the VHH to be soluble. Interestingly, even though P10 was derived from Llama No: 1, its framework sequences looks more like Llama No: 2's, indicating that there were VHH sequences present in Llama No: 1's original library with the correct framework regions, but biopanning did not favor selection of those sequences.

Example 7

Purification of Monovalent and Bivalent VHH

Figure 13A:
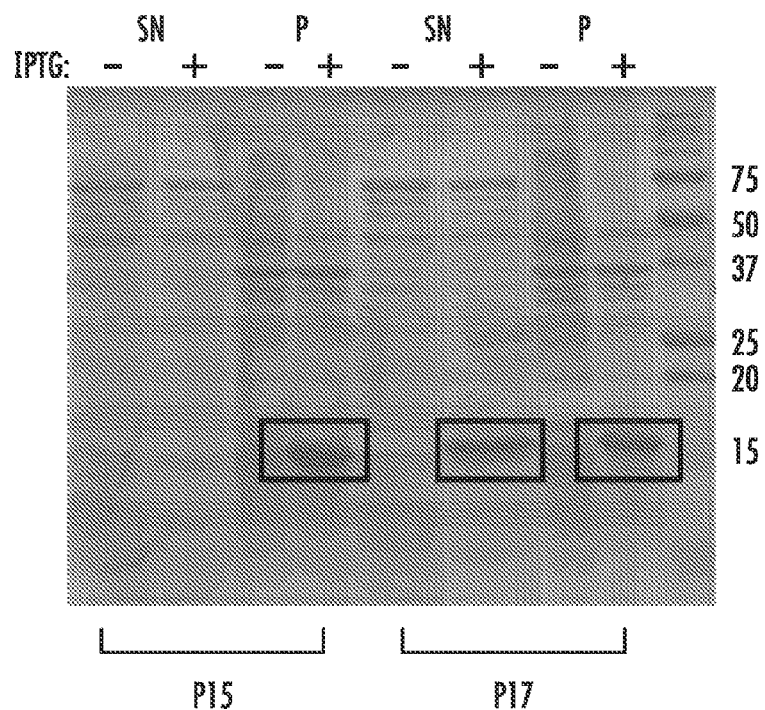
FIG. 13 depicts expression and purification of VHH from E. coli. A) E. coli were transformed with VHH/pET plasmids and small scale cultures were grown and induced to determine solubility of VHH proteins. A representative gel demonstrating that VHH derived from one llama are located in the pellet (P), while VHH derived from a second llama are located in both the supernatant (SN) and the pellet. B) A representative gel demonstrated the size and purity of purified R33 and bvR33.
Figure 13B:
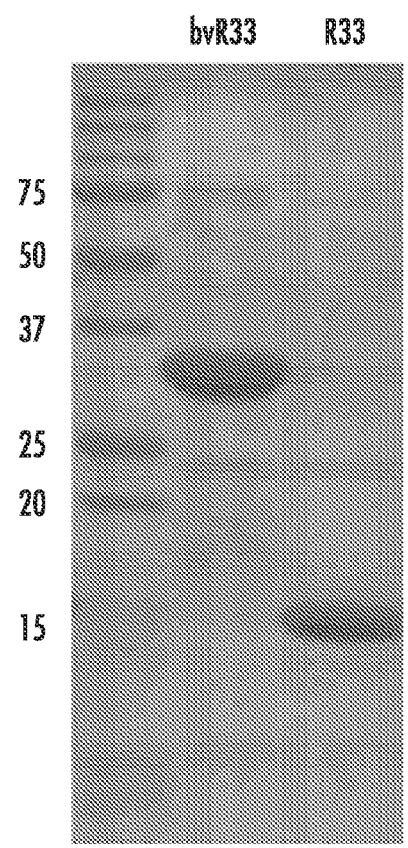

VHH sequences were amplified from T7 phage as monovalent or bivalent (R33 only) VHH and cloned in to pET-47b for expression in *E. coli*. The purified VHH proteins were separated by SDS-PAGE for Coomassie staining to determine size and purity. All VHH derived from Llama No: 2 were located in the soluble fraction after induction, while all of Llama No: 1's VHH were located in the pellet, as demonstrated in the representative gel in FIG. 13A. This observation is consistent with the sequence analysis that suggested the lack of conserved VHH residues in the FR2 region of Llama No: 1's sequences might impact solubility. Proteins of approximately 15 kDa for monovalent VHH and approximately 30 kDa for bivalent VHH were detected (FIG. 13B).

Example 8

Binding of Monovalent and Bivalent VHH to gD2

Figure 14A:
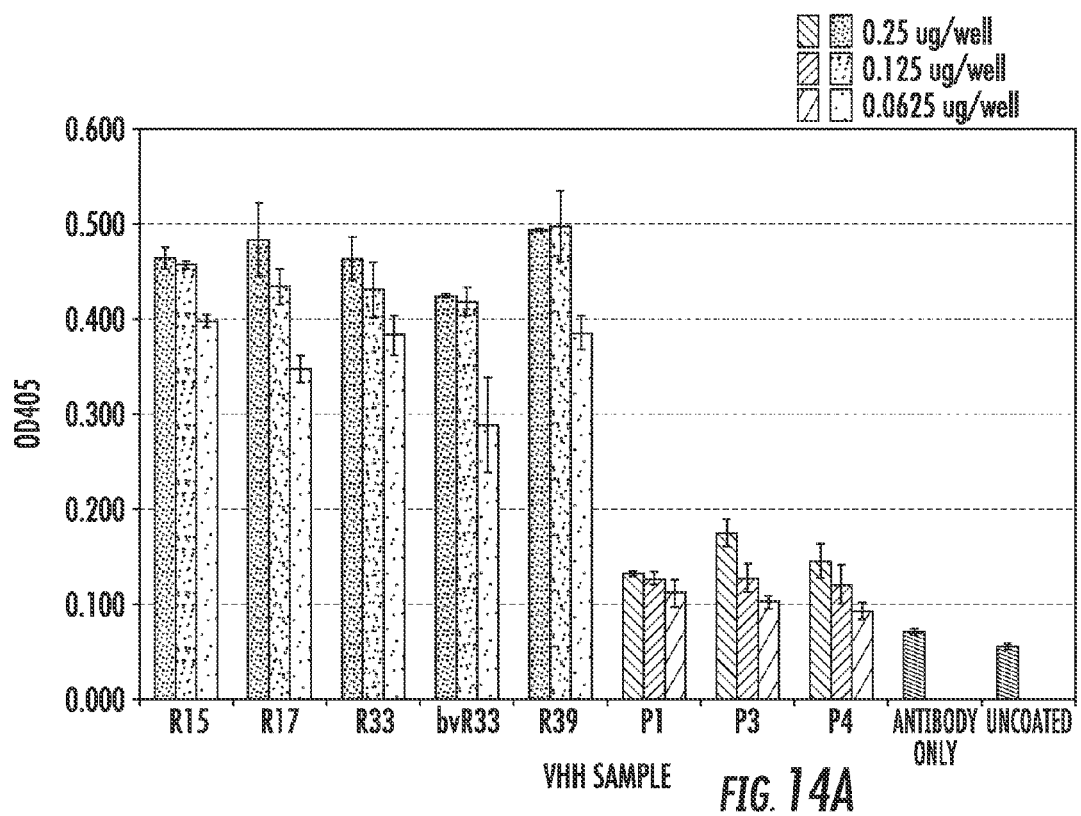
FIG. 14 shows that purified VHH bind to gD2. ELISAs were performed in which wells were coated with VHH and gD2 was added to assay for their ability to bind gD2. Each dilution was assayed in duplicate and error bars represent maximum and minimum values.

The ability of the purified VHH to bind to gD2 was tested by ELISA (FIG. 14 14). Surprisingly, despite the high binding of Llama No: 1's VHH to gD2 when expressed as a fusion protein on the surface of the phage, purified VHH from Llama No: 1 show minimal binding to gD2. Conversely, while VHH-phage from Llama No: 2 bound poorly to gD2, when expressed and purified, R33 exhibits superior binding ability. There does not appear to be enhanced binding with bivalent R33 compared to monovalent R33 when added in equimolar amounts. It is possible that expression of Llama No: 1's VHH as a fusion protein with phage proteins forces the VHH to fold in a way that promotes binding, but when these same VHH sequences are expressed by *E. coli* as a monomeric proteins, they are no longer constrained by flanking phage protein and are unable to fold and bind to gD2.

The same pattern of gD2 binding was also demonstrated by flow cytometry. We used FACS analysis with z4/6 cells that express gD2 on their surface as a way to measure native gD2 expressed at the cell surface. All VHH derived from Llama No: 2, including the bivalent R33, were again able to bind z4/6 cells, while P4 was unable to bind (FIG. 15).

Example 9

Pentavalent VHH

Figure 14B:
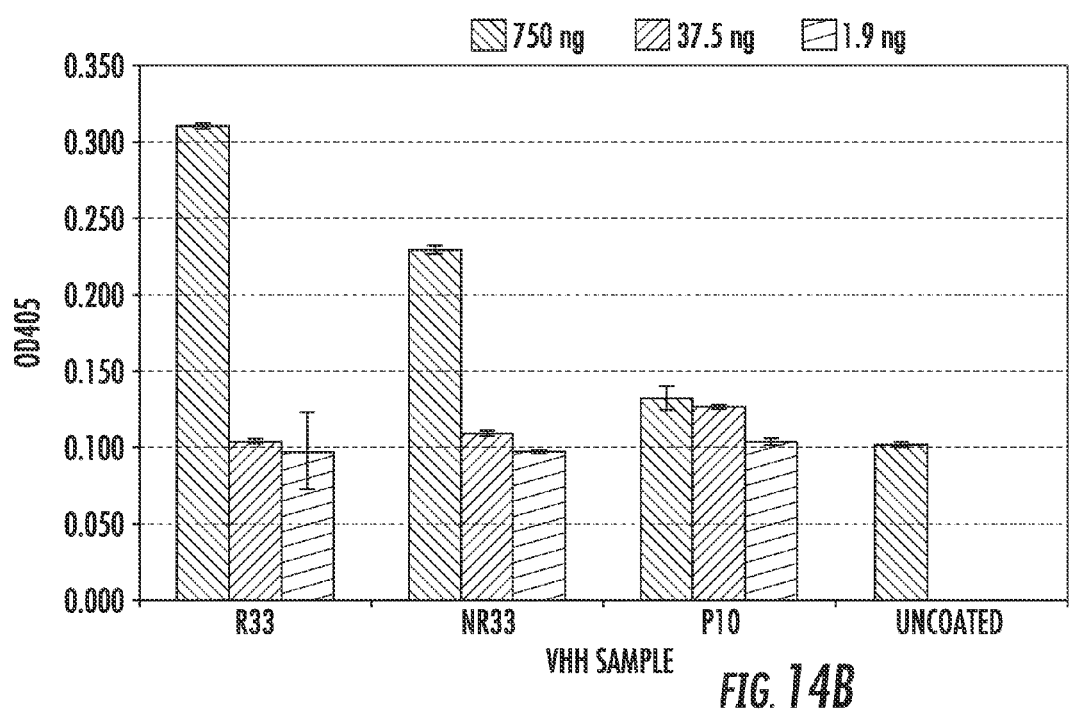
Figure 15A:
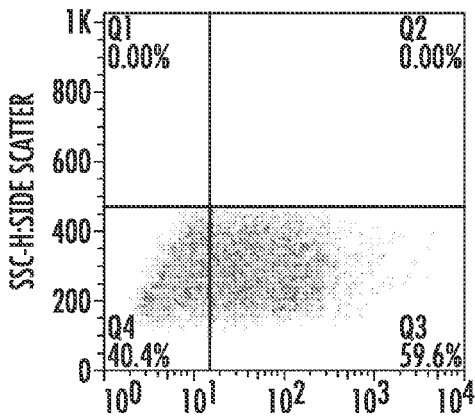
FIG. 15 depicts VHH binding to gD2-expressing cell line. To determine if VHH could bind to gD2 expressed at the cell surface, z4/6 cells (surface expression of gD2) were stained with various VHH (C: R33, D: P4, E: bvR33, F: R15) and detected by a FITC-conjugated secondary antibody. DL6 was used as a positive control to verify that gD2 was expressed (A), and a secondary antibody control with no VHH or primary antibody was also used as a negative control (B).
Figure 15B:
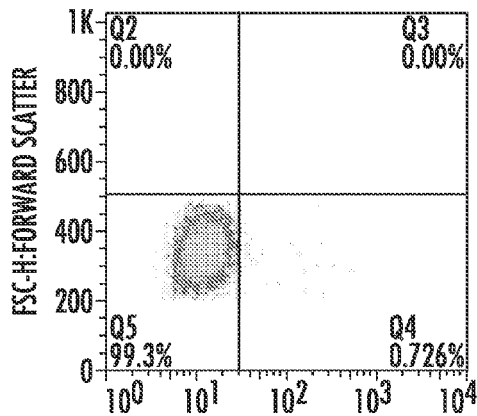
Figure 15C:
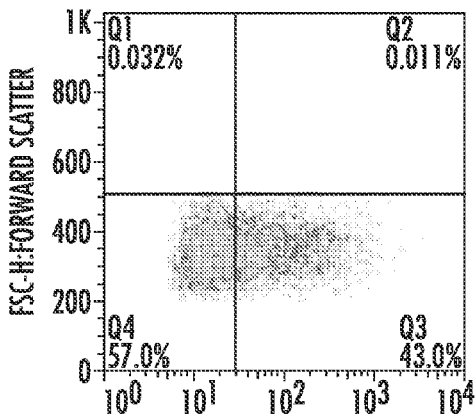
Figure 15D:
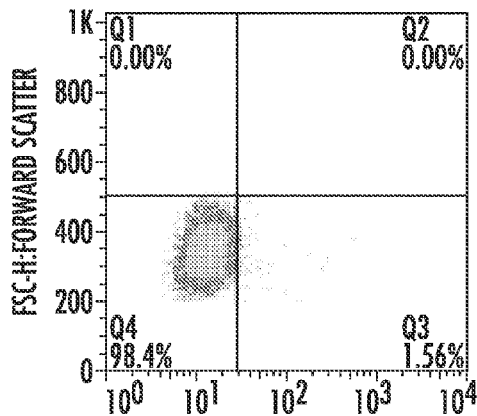
Figure 15E:
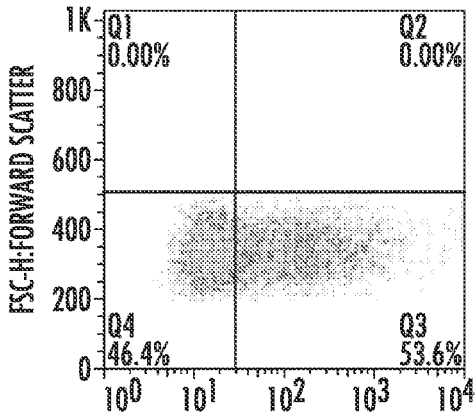
Figure 15F:
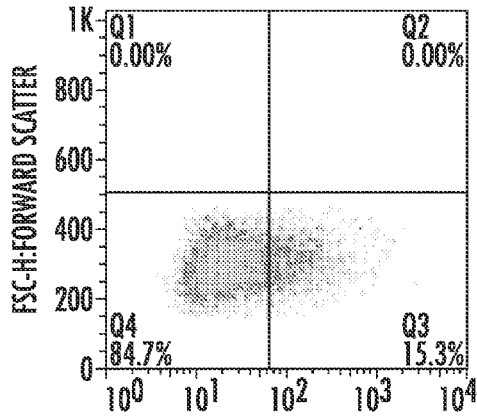
Figure 16:
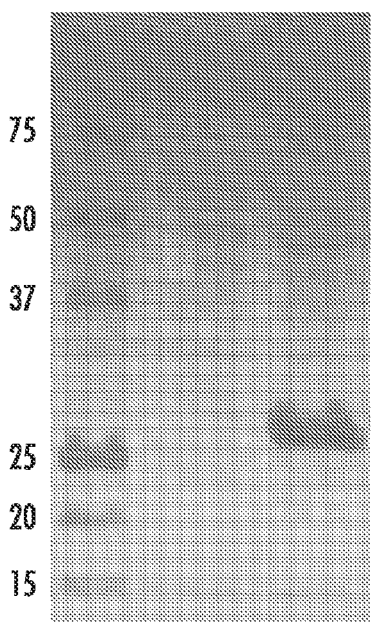
FIG. 16 depicts the purification of pentavalent VHH. R33 expressed as a fusion protein with the verotoxin B subunit (NR33), allowing for pentamerization, were purified from transformed E. coli and separated by SDS-PAGE for staining with Coomassie to determine size and purity. Upon dialysis, the monomers self-assemble in to a pentamer.

Based on increasing evidence that VHH have enhanced activity when expressed in multivalent context, we expressed R33 as a fusion protein with the verotoxin B subunit, which allows for self-assembly into a pentamer. The verotoxin B subunit was fused to the N-terminus of R33 (NR33) and purified (FIG. 16A). To verify that the NR33 did self-assemble, a sample of the purified NR33 was run through a Superdex200 column and it was found that they eluted at a peak of about 100 kDa, roughly the size of the expected protein (data not shown). When corrected for valency, NR33 was able to bind to gD2 as measured by ELISA at similar levels compared to monovalent R33 (FIG. 14B).

Example 10

VHH Neutralization Assay

Figure 17A:
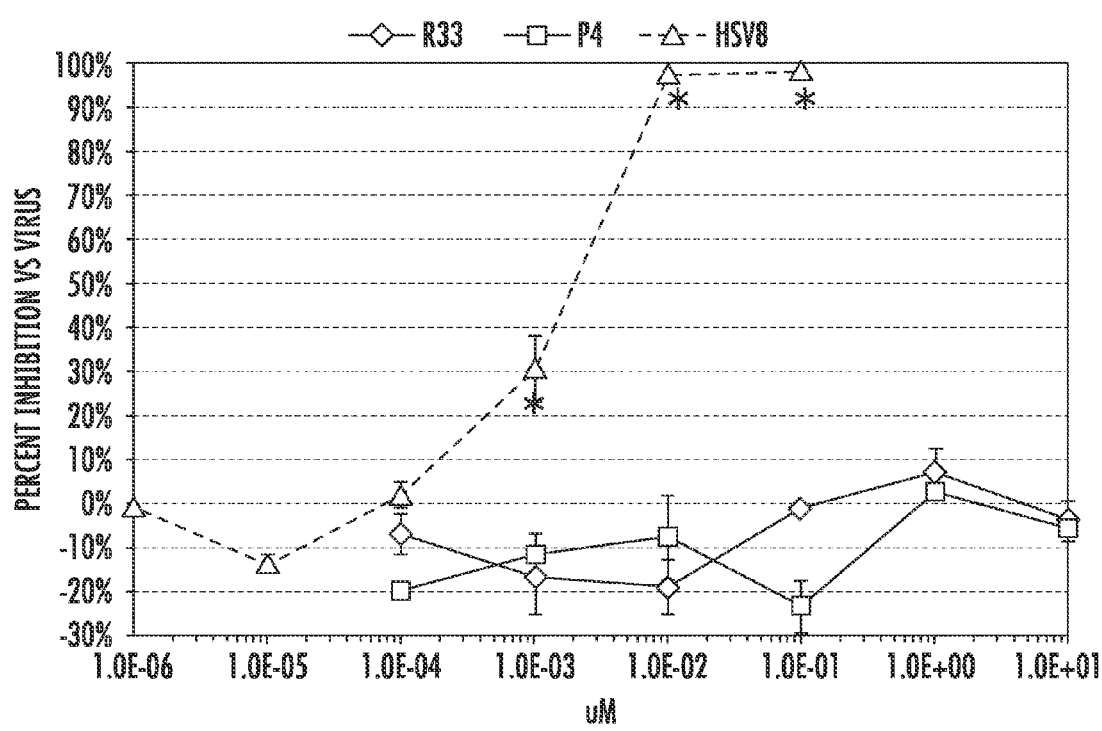
FIG. 17 shows the VHH neutralization of HSV-2 using the present invention. Virus was incubated with dilutions of VHH for 1 hour at 37° C. and then plated on Vero cells to assay for VHH neutralizing activity. Each dilution was assayed in duplicate and error bars represent maximum and minimum plaque numbers. Results are expressed as percent inhibition compared to plaque numbers from untreated virus. Statistical significance compared to untreated virus was calculated by ANOVA and is indicated by asterisks ($P<0.05$). The known neutralizing antibody HSV8 was used in graph A as a positive control.
Figure 17B:
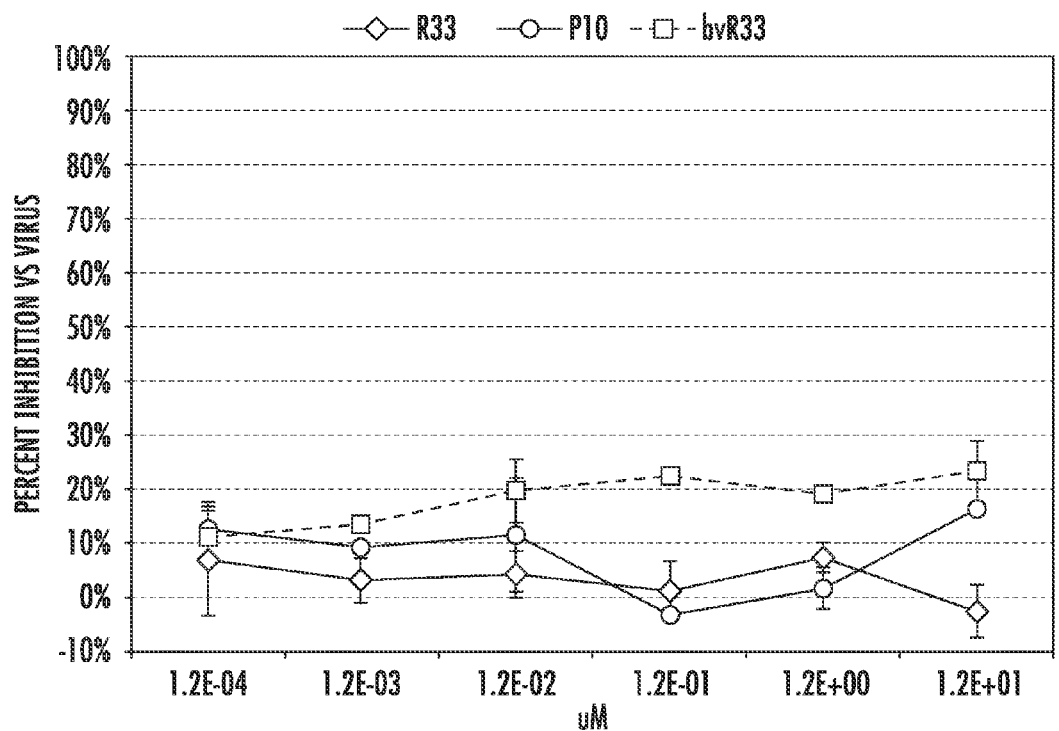
Figure 17C:
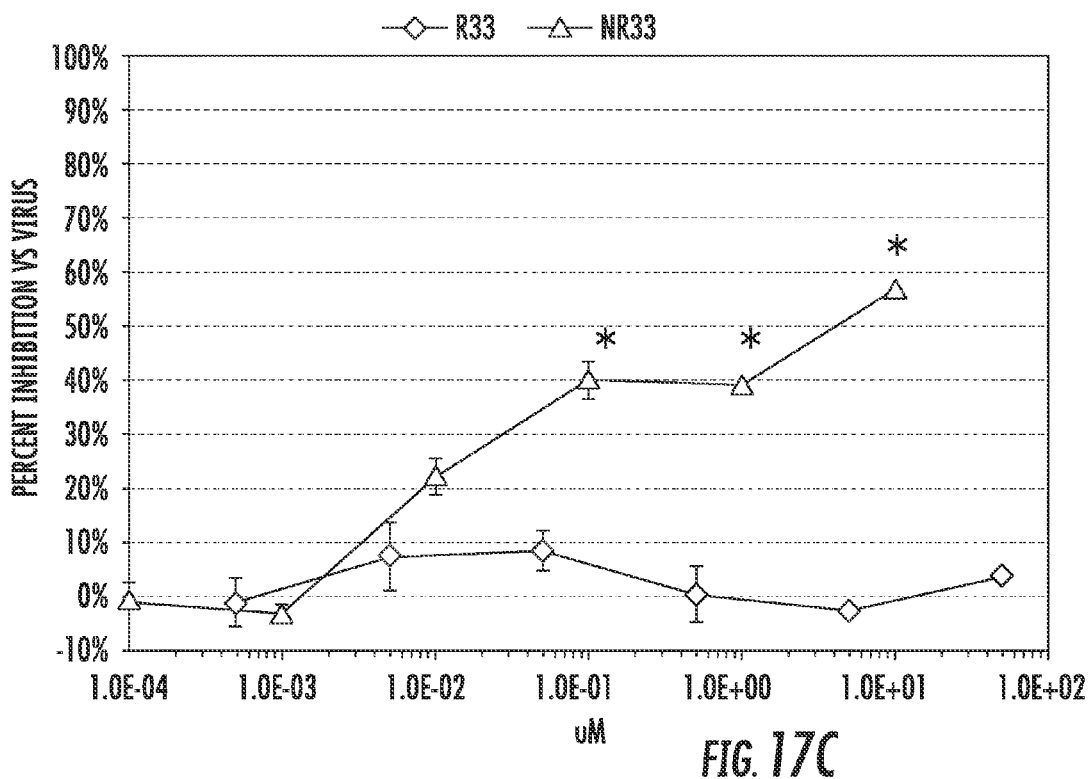
Figure 18:
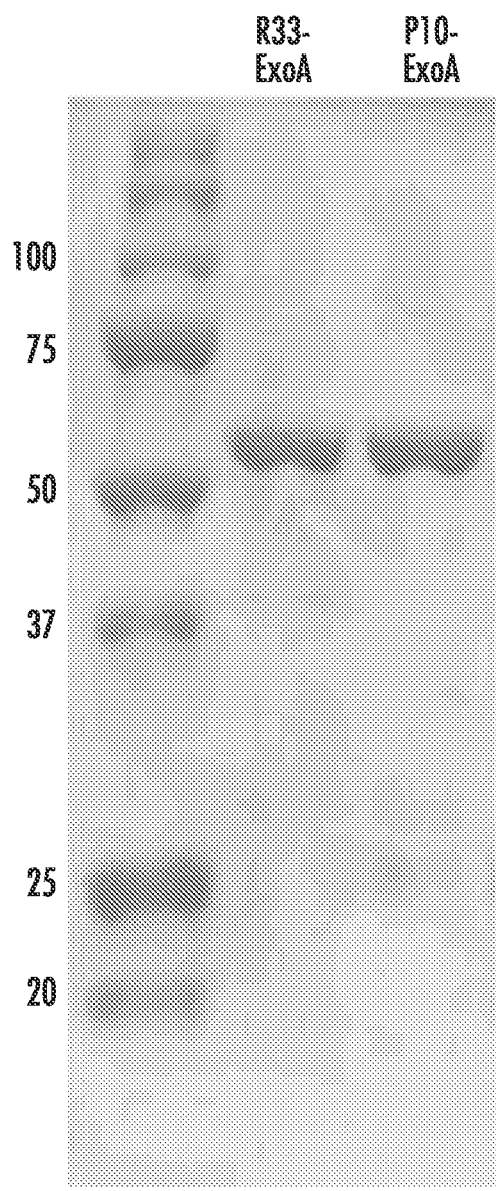
FIG. 18 shows that VHHExoA were purified from the insoluble fraction of induced E. coli cells and refolded according to previously published protocols.

All forms of the VHH (monovalent, bivalent, pentavalent, were tested in an HSV-2 neutralization assay. R33, bvR33, P4 were unable to neutralize the virus at the concentrations tested (FIGS. 17A and B). Neutralization assays with pentameric R33 showed that NR33 does have neutralizing activity, and that the inhibition compared to untreated virus is statistically significant at several of the dilutions tested (FIG. 17C). At the highest amount tested (10 µM), NR33 neutralized the virus at 57% and the inhibition remained statistically significant until 0.1 µM. Protein precipitation at higher concentrations prevented testing neutralization activity at higher levels of pentavalent VHH from being tested, so it is not possible to calculate an $IC_{50}$ for NR33 from the completed experiments, but it is clear from multiple experiments that the inhibition is consistent and statistically significant. Further protein purification troubleshooting would likely allow for higher concentrations to be evaluated.

Example 11

Testing VHH in Vaginal HSV-2 Animal Challenge Model

As shown in Table 1, CF-1 female mice were treated with Depo-provera, and one week after 10 $ID_{50}$ HSV-2 G was mixed with PBS, P10, R33 and promptly delivered to the mouse vagina. Three days later the vagina was lavaged, and fluid was plated on foreskin cells to assay for the presence of virus. At the time of animal testing, the gD2-binding VHH candidates that were available were R33 and bvR33. P10 was used as the negative control. Equivalent amounts of R33 and P10 were mixed with virus and introduced in to the mouse vagina to determine if the VHH had any HSV-2 in vivo neutralizing capability.

TABLE 1

Testing VHH in Vaginal HSV-2 Animal Challenge Model.

| Sample | Input | # Infected | Total # | % Infected |
|---|---|---|---|---|
| Virus/PBS | 10 $ID_{50}$ | 17 | 24 | 71% |
| P10 | 100 µM | 10 | 17 | 59% |
| R33 | 100 µM | 11 | 18 | 61% |

Example 12

Purified R33ExoA Binds to gD2

Figure 19:
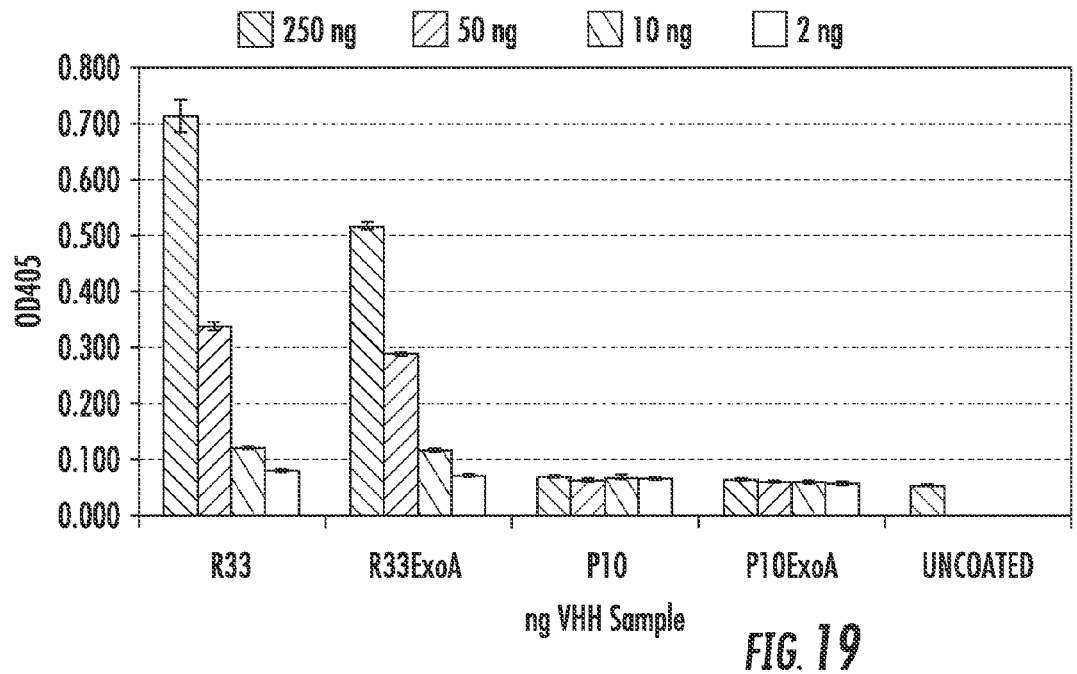
FIG. 19 illustrates that VHH and VHHExoA Bind to gD2. A capture ELISA was performed to determine if the VHH portion of R33ExoA is able to bind gD2 when expressed with a C-terminal exotoxin A. Each dilution was assayed in duplicate and error bars represent maximum and minimum values.
Figure 20A:
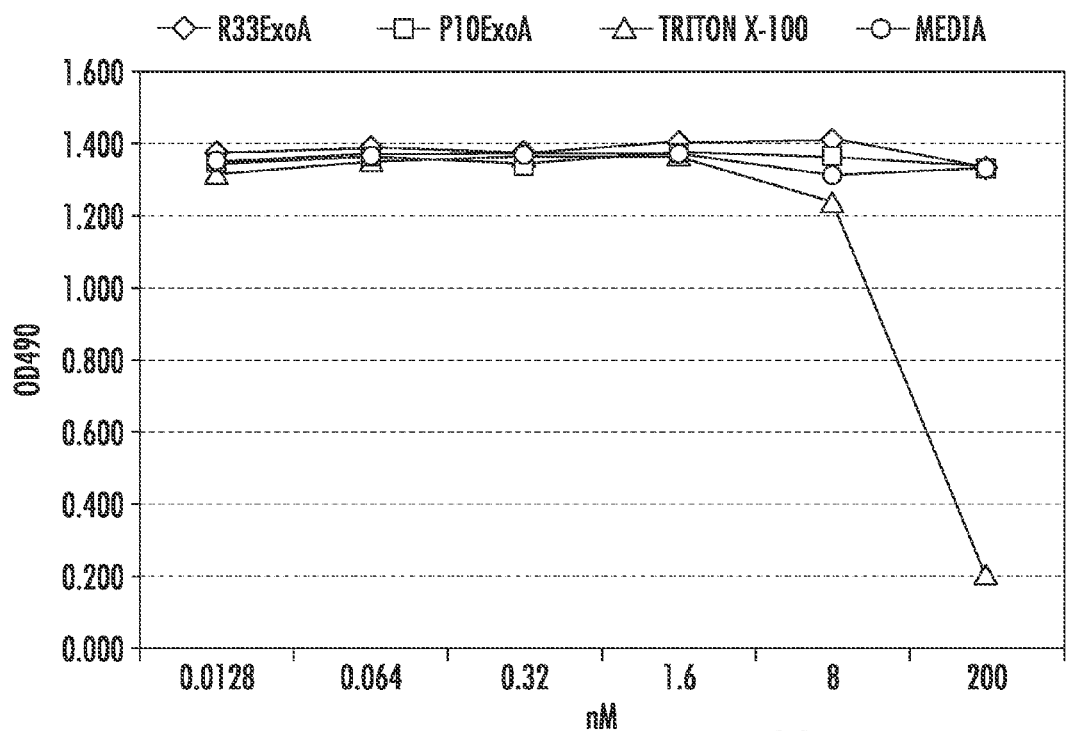
FIG. 20 shows the toxicity of VHHExoA on Vero cells and z4/6 cells. 20A) Dilutions of VHH-ExoA proteins were added to Vero cells (do not express gD2) and their cytotoxicity was measured by addition of MTS reagent (Promega, Madison, Wis.). Triton X-100 was added at 0.05% to the first dilution to serve as a positive control for cytotoxicity, and it diluted as the other samples were. Dilutions of each protein were added to wells in triplicate and error bars represent standard deviation. 20B) Dilutions of VHH-ExoA proteins were added to z4/6 cells (express gD2) and their cytotoxicity was measured by addition of MTS reagent (Promega, Madison, Wis.). Triton X-100 was added at 0.05% to the first dilution to serve as a positive control for cytotoxicity, and it diluted as the other samples were. Dilutions of each protein were added to wells in triplicate and error bars represent standard deviation.
Figure 20B:
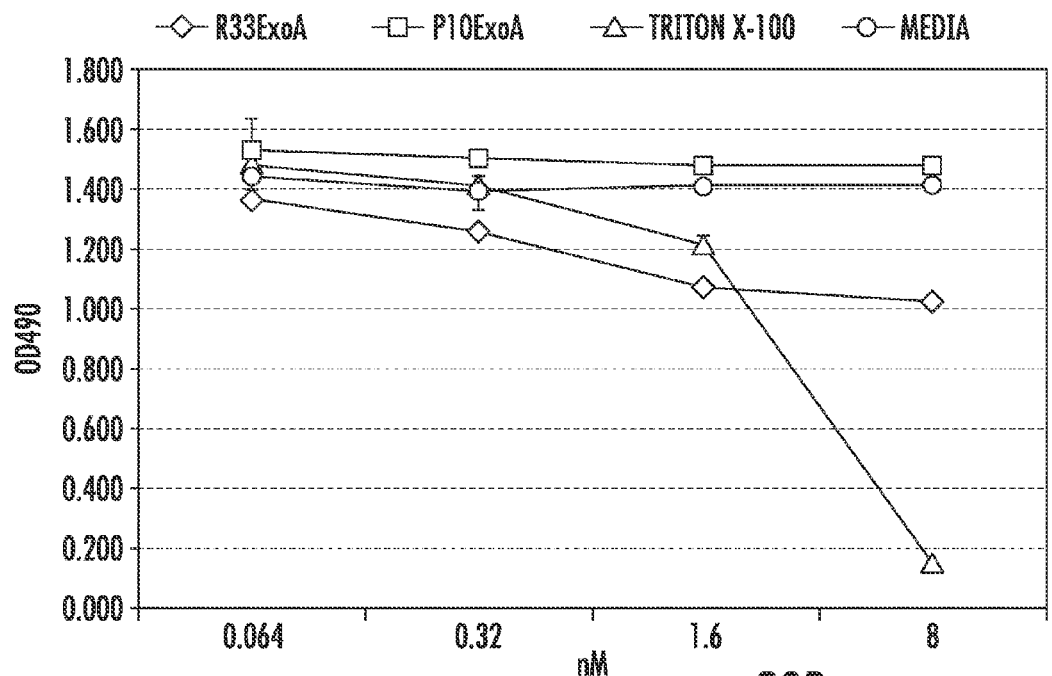
Figure 21:
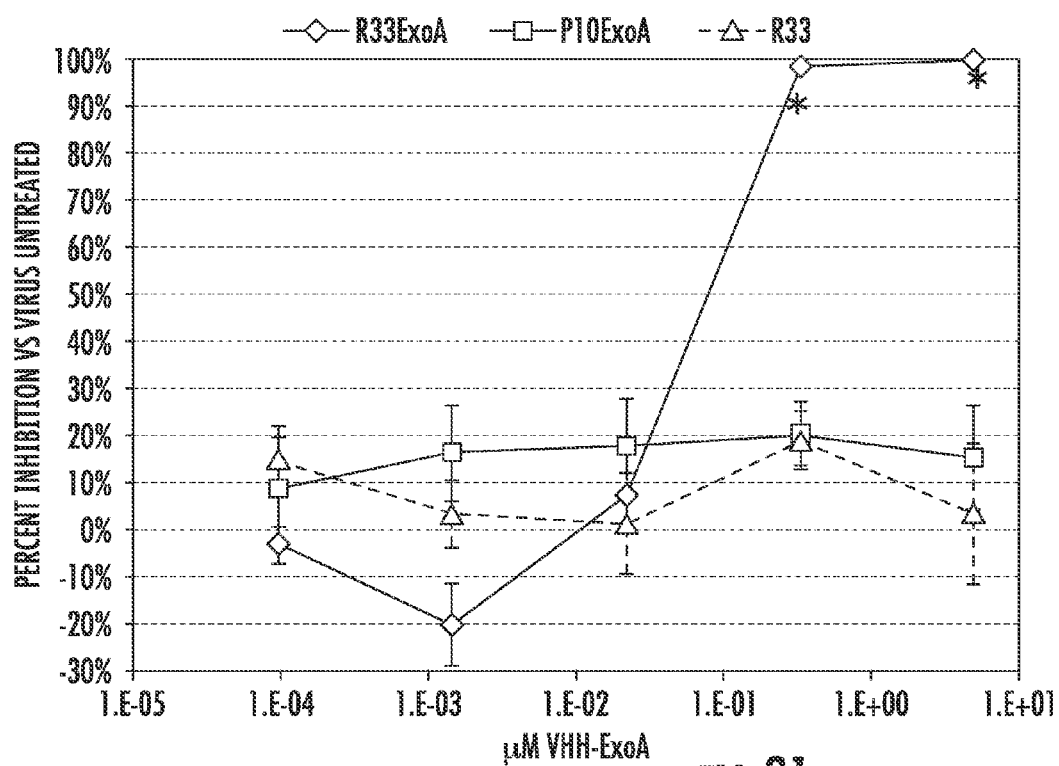
FIG. 21 provides results of a VHHExoA infectious center assay. HSV-2 infected Vero cells were treated with dilutions of VHHExoA, R33, or PBS for about 16 hours. Infected cells were then harvested and diluted in uninfected Vero cells to assay for the number of infectious centers that remain. This is a representative graph from four independent experiments. Error bars represent standard error of the mean.

Purification of immunotoxins is potentially complicated by the need to optimize conditions so that the antibody and exotoxin components of the molecule will each fold correctly and maintain their distinct functions. The VHHExoA immunotoxins were purified from induced BL21 cells (FIG. 21). Based on protocols published by Buchner et al for an scFv immunotoxin, the VHHExoA (R33ExoA and P10ExoA) were refolded and the antibody function was tested by ELISA. R33ExoA was still able to bind gD2 at levels comparable to R33 alone, while P10 and P10ExoA had no gD2 binding activity (FIG. 19).

Example 13

Purified R33ExoA is Functional as an Immunotoxin

To test the exotoxin capability of the immuntoxin, a MTS assay with z46 cells was used that express gD2, and the parental cell line, L cells that do not express gD2. Z46 cells are known to not have uniform expression of gD2, as shown in FIG. 15, through staining with the anti-gD antibody DL6, but levels of gD2 expression should be sufficient to determine if R33ExoA can exert a cytotoxic effect on cells expressing gD2. FIG. 23 demonstrates that R33ExoA only has a cytotoxic effect on z46 cells and not the parental cell line, and that the non-gD2 binding P10ExoA has no cytotoxic effect on either cell line compared to cells treated with media alone.

Example 15

Infectious Center Assay (ICA)

To test the cytotoxic effect of the R33ExoA on HSV-2 infected cells, an infectious center assay was performed (FIG. 21). Cells were infected with HSV-2 in the presence of the VHHExoA, and allowed to proceed for roughly 16 hours. Cells were harvested at this time, mixed with uninfected target cells, and then diluted and plated so that the number of infectious centers can be quantified. R33ExoA consistently demonstrated potent antiviral activity compared to P10ExoA and R33 with no ExoA, which had no antiviral activity. Multiple repetitions of the ICA revealed that the $IC_{50}$ of R33ExoA is between 0.01 and 0.1 µM.

Example 16

R33ExoA Activity as a Microbicide

The VHHExoA immunotoxins were tested in the mouse microbicide model to determine if they have the ability to protect against vaginal HSV-2 infection. Three treatments were used: PBS, R33ExoA, and P10ExoA. The viral inoculum was first mixed with VHHExoA (infection control group was mixed with PBS) before introduction in to the vagina. At three time points post-infection (6, 24, and 48 hours) animals received additional doses of VHHExoA proteins (or PBS) so that the immunotoxins were present in the vagina at times when gD2 would be expressed at the cell surface and to mimic the repeated application that would accompany its use as a microbicide or treatment in humans. As shown in Table 2, the infection control group (received only PBS) was infected at a frequency of 89% (8 out of 9 animals), indicating the virus was properly infectious. Similarly, in the group of animals that received P10ExoA, 7 out of 8, or 88% of animals became infected. Only 3 out of 8, or 38%, of animals treated with R33ExoA became infected, a level that is statistically significant when compared to the infection control group (P=0.048), and approaches but does not reach statistical significance when compared to the P10ExoA group (P=0.119). Nonetheless, this result is promising and indicates that further animal testing exploring the use of R33ExoA as a microbicide or treatment is warranted.

TABLE 2

Testing VHHExoA in Vaginal HSV-2 Animal Challenge Model

| Group | Viral Input | Treatment | # Infected | Total # | % Infected |
|---|---|---|---|---|---|
| Virus | 10 $ID_{50}$ | PBS | 8 | 9 | 89% |
| R33ExoA | 10 $ID_{50}$ | 10 µM | 3 | 8 | 38% |
| P10ExoA | 10 $ID_{50}$ | 10 µM | 7 | 8 | 88% |

(Fisher exact test, two-tailed: Virus Only compared to R33ExoA: p = 0.0498; P10ExoA compared to R33ExoA: p = 0.1189)

Example 17

We next sought to examine whether a similar approach might work for HIV-1. Because a broadly neutralizing VHH had already been identified by the Weiss group (J Exp Med, 2012. 209(6): p. 1091-103), we synthesized the DNA encoding the CDR's of that VHH, termed J3, and inserted it into the VHH backbone DNA from our anti-gD construct, already present in the pET-47b vector. The previously published exotoxin A sequence HA22 (Blood, 2004. 103(7): p. 2718-26) with point mutations to remove immunogenic human B-cell epitopes (Proc Natl Acad Sci USA, 2012. 109(29): p. 11782-7) was synthesized and cloned in frame to the C terminus of the VHH. HA22 encodes a 38-kDa derivative of the 66-kDa *Pseudomonas* exotoxin (PE) in which the cell binding domain of PE (domain Ia, amino acids 1-252) and a portion of domain Ib (amino acids 365-380) are deleted. The amino acid sequence of J3VHH with EcoR1 5' end and Avrll 3' end is shown in FIG. 23 as SEQ ID NO: 7. The *P. aeruginosa* Exotoxin A subunit which is attached to the 3' end of SEQ ID NO: 7 in the full construct, is shown in FIG. 23 as SEQ ID NO: 8. The full protein expression sequences with the start codon and His tag and linkers are shown in FIG. 24 as SEQ ID NOS: X, and Y.

Example 18

Figure 25:
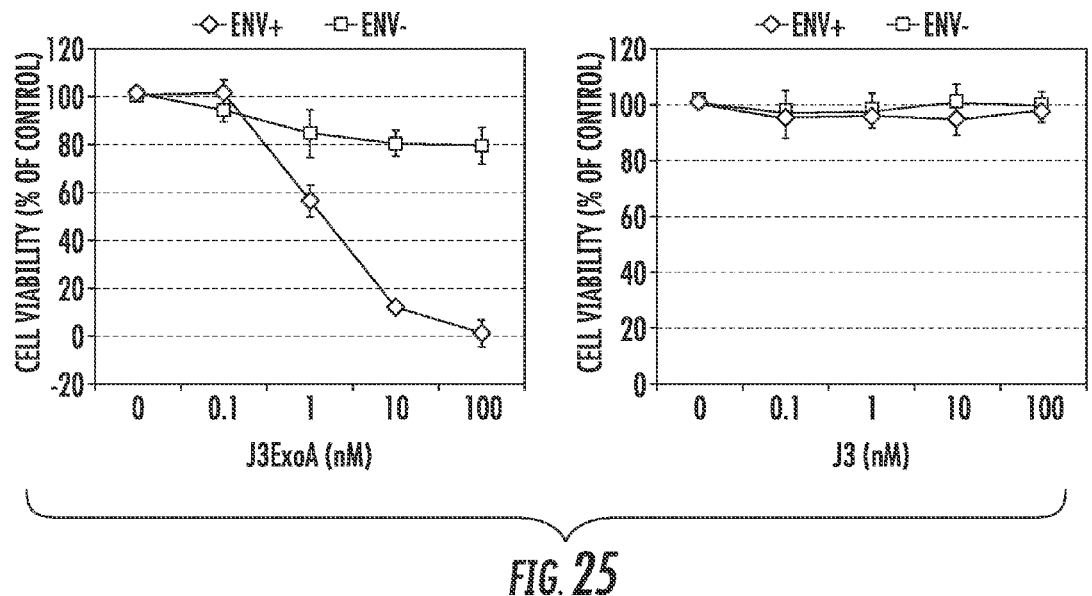
FIG. 25 depicts cell viability graphs showing the viability of CHO cells expressing or not expressing envelope after exposure to either the J3 VHH or J3 VHH fused to exotoxin A.

We next evaluated the ability of this construct to kill cells expressing HIV-1 envelope. For this purpose $1 \times 10^4$ ENV$^+$ and ENV$^-$ CHO cells were incubated with J3ExoA (A), or J3 (B) for 40 h. Cell viability was determined by MTS assay and normalized to 100% for no added protein. As seen in FIG. 25, only J3ExoA specifically killed envelope expressing cells ($p<0.001$ for 1, 10 and 100 nM concentrations vs. no treatment), while even at the 100 nM concentration of the J3ExoA the viability of the envelope negative cells did not differ significantly from the untreated controls ($p>0.8$).

Example 19

Figure 26:
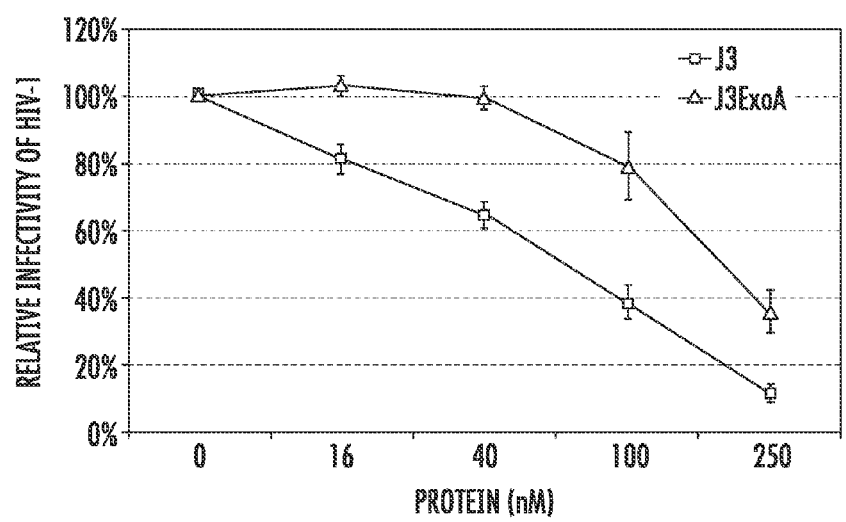
FIG. 26 shows the relative neutralizing capability of J3 and J3ExoA. HIV-1 AD8 virus were produced from 293T cells and incubated with indicated concentration of J3 or J3ExoA for 1 h, and then infected MAGI-CCR-5 cells. Viral infection was determined by MAGI assay. The infectivity of AD8 in absence of any protein was set as 100%.

Because transformed cells expressing envelope might not be representative of expression levels after viral infection, we also tested the ability of J3ExoA to kill HIV-1 infected primary PBMC from normal donors. We first tested the relative neutralizing capability of J3 with and without fused ExoA. In this study virus was incubated for one hour with the two VHH constructs, placed on Magi-CCR5 cells for one hour and assayed for establishment of infection. As seen in FIG. 26, both constructs retained neutralizing capability, but J3 without ExoA was clearly more potent ($p<0.01$ at all concentrations ≥16 nM.

Example 20

Figure 27:
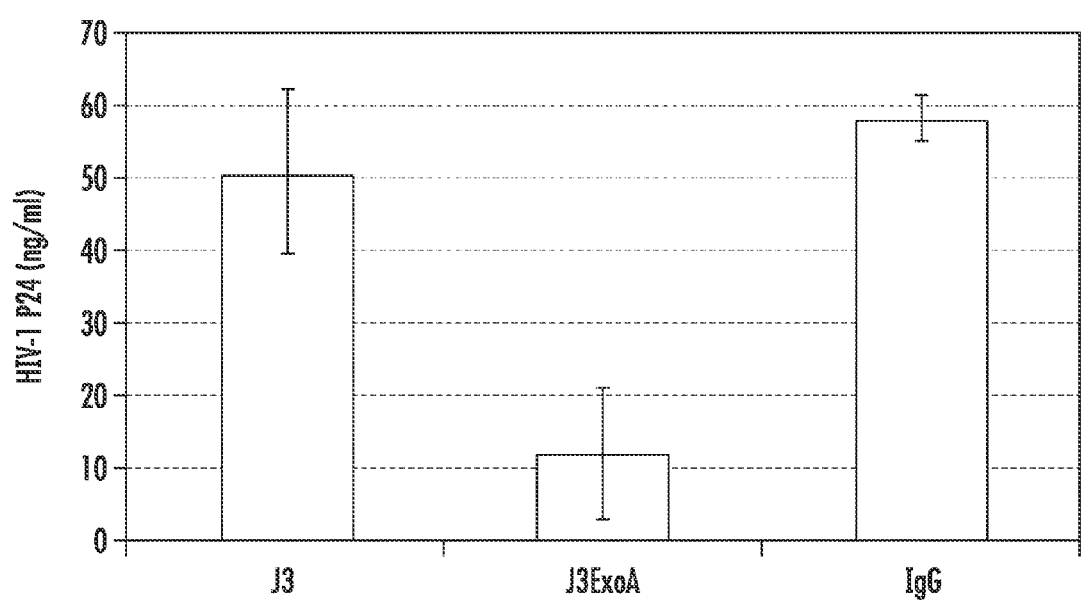
FIG. 27 shows Relative ability of 50 nM J3 and J3ExoA to reduce viral load in PBMC culture when exposed to cells pre-infected with $HIV_{BaL}$.

We then tested the relative ability of the two constructs to kill HIV-1 infected PBMC. For this study PBMC were infected with HIV-1$_{BaL}$ for 24 hours and then washed with medium twice and incubated in the presence of 50 nM of J3ExoA or J3 for 4 days. Viral persistence was assayed by ELISA of p24 in the culture fluid. IgG was used as the negative control. The results (FIG. 27) indicate that despite inferior neutralizing capability J3ExoA significantly reduced p24 levels compared to J3 alone, supporting the interpretation that, even in the absence of antiretroviral therapy, this VHH is highly effective at killing naturally infected PBMC.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A heavy chain immunoglobulin of the VHH type or fragment thereof comprising an amino acid sequence of at least 85% identity to SEQ ID NO: 7, and having affinity for envelope proteins of HIV-1.

2. A heavy chain immunoglobulin of the VHH type or fragment thereof comprising an amino acid sequence of at least 85% identity to SEQ ID NO: 8, and having affinity for envelope proteins of HIV-1, which is covalently linked to the *P. aeruginosa* Exotoxin A subunit.

3. The heavy chain immunoglobulin of the VHH type or fragment thereof of claim 2, having an amino acid sequence of at least 90% identity to SEQ ID NO: 8.

4. A multimeric molecule comprising a heavy chain immunoglobulin fragment of the VHH type according to claim 2, in which VHH sequences are fused to yield multimeric units of 2 or more VHH units optionally linked via a spacer molecule.

5. A multimeric molecule comprising two or more VHH sequences according to claim 2, which are fused to yield 2, 3, 4 or 5 or more VHH units optionally linked via a spacer molecule.

6. A nucleic acid encoding a heavy chain immunoglobulin fragment of the VHH type according to claim 1.

7. An expression vector comprising the nucleic acid encoding a heavy chain immunoglobulin fragment of the VHH type according to claim 1.

8. The expression vector of claim 6 comprising the nucleic acid sequence of SEQ ID NO: 6.

9. A micro-organism transformed with the expression vector of claim 8.

10. A micro-organism according to claim 9, wherein the micro-organism is *Lactobacillus*.

11. The micro-organism according to claim 10, selected from the group consisting of *L. jensenii, L. reuteri, L. gasseri, L. crispatus,* and *L. iners*.

12. A method for treatment of an HIV-1 infection in a subject, comprising administering to the subject a heavy chain immunoglobulin or fragment thereof of claim 1.

13. A method for treatment of an HIV-1 infection in a subject, comprising administering to subject a micro-organism of claim 9 expressing the heavy chain immunoglobulin or fragment of claim 1.

14. A heavy chain immunoglobulin of the VHH type or fragment thereof comprising an amino acid sequence of at least 85% identity to SEQ ID NO: 11, and having affinity for envelope proteins of HIV-1.

15. A heavy chain immunoglobulin of the VHH type or fragment thereof comprising an amino acid sequence of at least 85% identity to SEQ ID NO: 12, and having affinity for envelope proteins of HIV-1, which is covalently linked to the *P. aeruginosa* Exotoxin A subunit.

16. The heavy chain immunoglobulin of the VHH type or fragment thereof of claim 15, having an amino acid sequence of at least 90% identity to SEQ ID NO: 12.

17. A method for treatment of an HIV-1 infection in a subject, comprising administering to the subject the multimeric molecule of claim 4.

18. A method for treatment of an HIV-1 infection in a subject, comprising administering to subject a micro-organism of claim 11 expressing the multimeric molecule of claim 5.

* * * * *